(12) United States Patent
Dong et al.

(10) Patent No.: US 10,470,379 B1
(45) Date of Patent: Nov. 12, 2019

(54) HIGH-THROUGHPUT LARGE-SCALE PLANT PHENOTYPING INSTRUMENTATION

(71) Applicant: IOWA STATE UNIVERSITY RESEARCH FOUNDATION, INC., Ames, IA (US)

(72) Inventors: Liang Dong, Ames, IA (US); Huawei Jiang, Ames, IA (US); Maneesha Aluru, Atlanta, GA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 1116 days.

(21) Appl. No.: 14/738,406

(22) Filed: Jun. 12, 2015

Related U.S. Application Data

(60) Provisional application No. 62/011,395, filed on Jun. 12, 2014.

(51) Int. Cl.
*A01G 9/14* (2006.01)
*A01G 9/26* (2006.01)
(Continued)

(52) U.S. Cl.
CPC .................. *A01G 9/26* (2013.01); *A01C 1/02* (2013.01); *A01G 9/14* (2013.01); *G06T 7/0016* (2013.01)

(58) Field of Classification Search
CPC .... A01G 9/14; A01G 9/26; A01C 1/02; G06T 7/0016
See application file for complete search history.

(56) References Cited

U.S. PATENT DOCUMENTS 5,009,029 A * 4/1991 Wittlin .................. A01G 31/02
47/18
5,764,819 A * 6/1998 Orr .......................... A01G 7/00
348/144
(Continued)

FOREIGN PATENT DOCUMENTS

EP          2875723 A1 * 5/2015 ........... A01G 9/0297
WO   WO-2012042084 A1 * 4/2012 ............... A01G 7/00

OTHER PUBLICATIONS

Jiang, Huawei, et al., "Plant Chip for High-Throughput Phenotyping of *Arabidopsis*", Lab on a Chip, 2014, 14, pp. 1281-1293; DOI:10.1039/C3LC51326B.
(Continued)

*Primary Examiner* — Monica L Williams
*Assistant Examiner* — Michael A. Fabula
(74) *Attorney, Agent, or Firm* — McKee, Voorhees & Sease, PLC

(57) ABSTRACT

Systems, methods, and apparatus for large scale, high throughput phenotyping of items including plants to derive environment/genetics correlations based on controlled variation of environment. Spatial and temporal resolution is improved by an integrated system that can use space efficiently yet concurrently process a large number of replicates but in varying environments. This is accomplished by using an array of miniature greenhouses, each in communication with one or more generators or regulators of an environmental factor that can be independently supplied and controlled to each miniature greenhouse. The controller also controls acquisition of data from each greenhouse as well as processing of that data into phenomic/genomic correlations.

9 Claims, 49 Drawing Sheets
(37 of 49 Drawing Sheet(s) Filed in Color)

(51) Int. Cl.
*A01C 1/02* (2006.01)
*G06T 7/00* (2017.01)

(56) References Cited

U.S. PATENT DOCUMENTS

| | | | | |
|---|---|---|---|---|
| 6,387,234 | B1* | 5/2002 | Yeung | G01N 27/44782 204/451 |
| 7,099,502 | B2* | 8/2006 | Shams | G06K 9/00 382/129 |
| 2002/0031813 | A1* | 3/2002 | Ozkan | B01J 19/0046 435/173.1 |
| 2002/0108857 | A1* | 8/2002 | Paschetto | B01L 3/0244 204/457 |
| 2003/0049862 | A1* | 3/2003 | He | B01L 3/5025 506/16 |
| 2003/0082551 | A1* | 5/2003 | Zarling | C12N 15/1079 435/6.16 |
| 2003/0124505 | A1* | 7/2003 | Jain | C12N 15/102 435/4 |
| 2004/0187515 | A1* | 9/2004 | Shu | B25J 11/00 62/378 |
| 2004/0194371 | A1* | 10/2004 | Kinnis | A01G 9/246 47/17 |
| 2005/0121536 | A1* | 6/2005 | Bavel | A01G 7/00 239/69 |
| 2005/0180608 | A1* | 8/2005 | Tanabata | A01G 7/00 382/110 |
| 2006/0207172 | A1* | 9/2006 | McDonald | A01G 7/00 47/58.1 R |
| 2007/0021929 | A1* | 1/2007 | Lemmo | G01N 35/00613 702/22 |
| 2007/0105214 | A1* | 5/2007 | Micklash, II | C12M 45/02 435/306.1 |
| 2008/0000815 | A1* | 1/2008 | Deppermann | B07C 5/3425 209/552 |
| 2008/0141585 | A1* | 6/2008 | Benfey | A01G 7/00 47/32.7 |
| 2008/0310674 | A1* | 12/2008 | Modiano | B07Q 5/34 382/100 |
| 2009/0000188 | A1* | 1/2009 | Sayers | A01G 7/00 47/58.1 R |
| 2010/0056382 | A1* | 3/2010 | Sussman | C12Q 1/6837 506/7 |
| 2010/0075865 | A1* | 3/2010 | Trau | B01J 19/0046 506/9 |
| 2011/0297589 | A1* | 12/2011 | Becker | A01C 1/00 209/552 |
| 2012/0220022 | A1* | 8/2012 | Ehrlich | G01N 15/14 435/286.2 |
| 2013/0104454 | A1* | 5/2013 | Deppermann | A01G 9/088 47/58.1 R |
| 2014/0173769 | A1* | 6/2014 | Leyns | A01G 7/00 800/260 |
| 2015/0286776 | A1* | 10/2015 | Denney | G06T 7/0016 506/12 |
| 2016/0143228 | A1* | 5/2016 | De Groot | A01G 9/24 700/284 |
| 2018/0242539 | A1* | 8/2018 | Bhattacharya | A01G 7/045 |

OTHER PUBLICATIONS

Jiang, H., et al., "A Microfluidic Whole-Plant Phenotyping Device", Transducers 2013, Barcelona, Spain, Jun. 16-20, 2013, pp. 1539-1542.

Clark et al., "Three-Dimensional Root Phenotyping with a Novel Imaging and Software Platform", Plant Physiology, vol. 156, pp. 455-465, Jun. 2011.

French et al., "High-Throughput Quanitifcation of Root Growth Using a Novel Image-Analysis Tool", Plant Physiology, vol. 150, pp. 1784-1795, Aug. 2009.

Iyer-Pascuzzi et al., "Imaging and Analysis Platform for Automatic Phenotyping and Trait Ranking of Plant Root Systems", Plant Physiology, vol. 152, pp. 1148-1157, Mar. 2010.

"KeyGene the Digital Phenotype—KeyGene", https://www.keygene.com/technology/2-the-digital-phenotype, 6 pages, accessed by the Applicant Jan. 7, 2019.

"LemnaTec—Digital Phenotyping", https://lemnate.com, 5 pages, accessed by Applicant Jan. 7, 2019.

"How will we ensure future nutrition?", https://www.plantphenomics.org.au, 7 pages, accessed by Applicant Jan. 7, 2019.

* cited by examiner

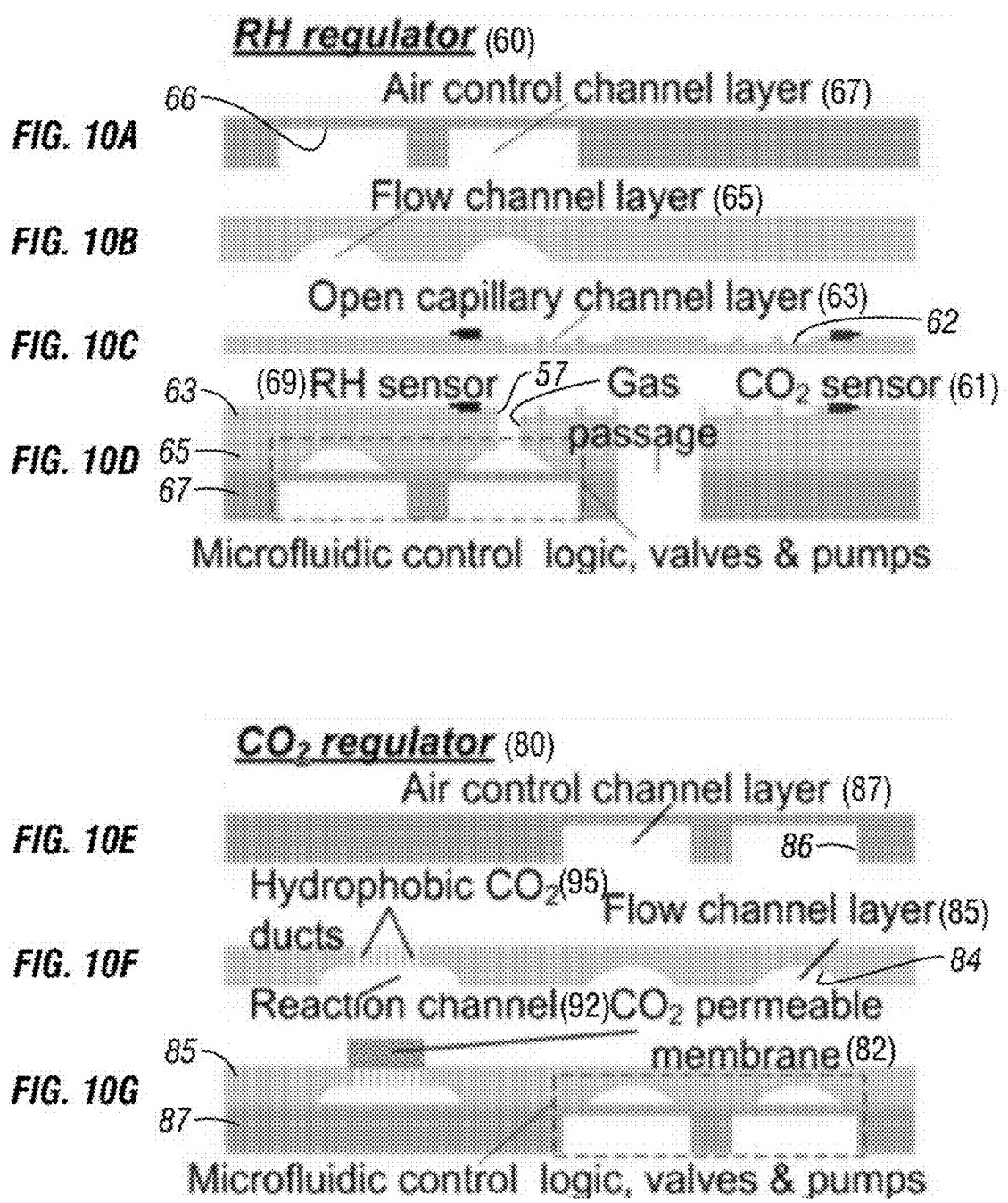

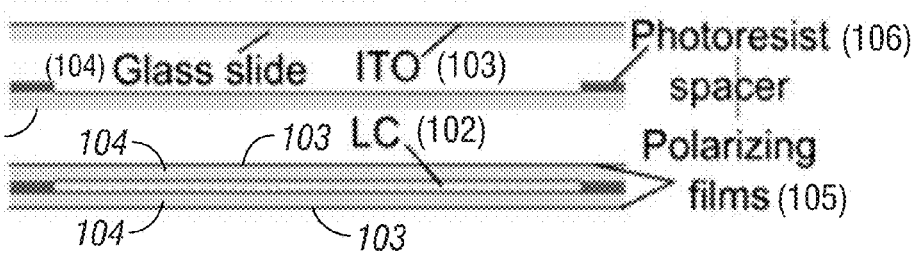
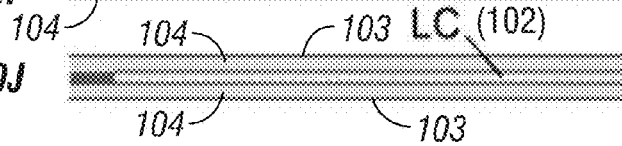
FIG. 10H, FIG. 10I, FIG. 10J
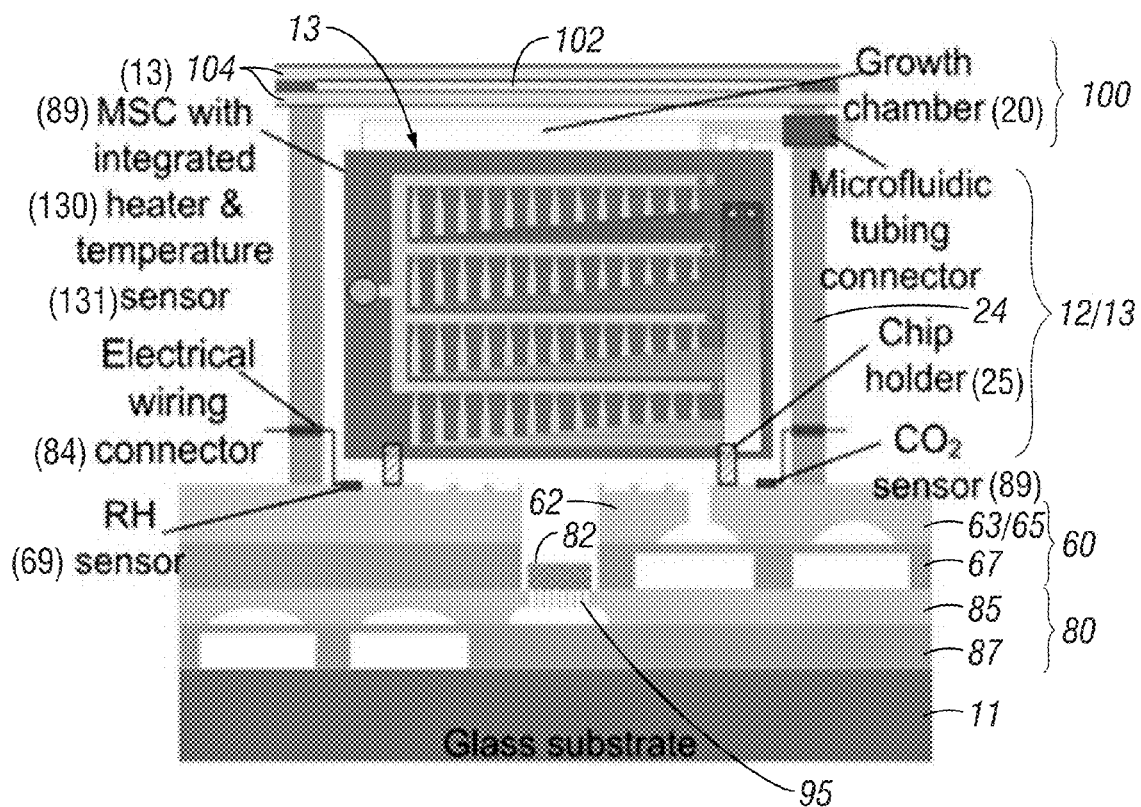
FIG. 10K

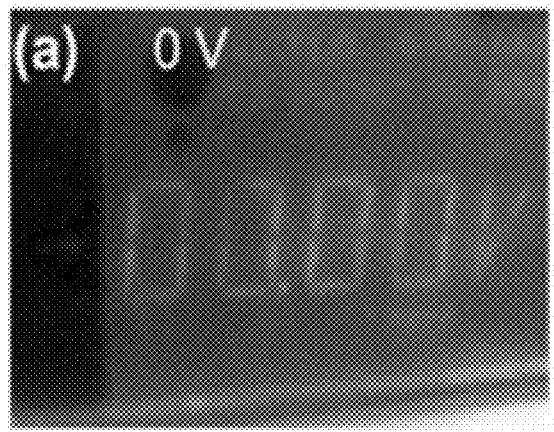
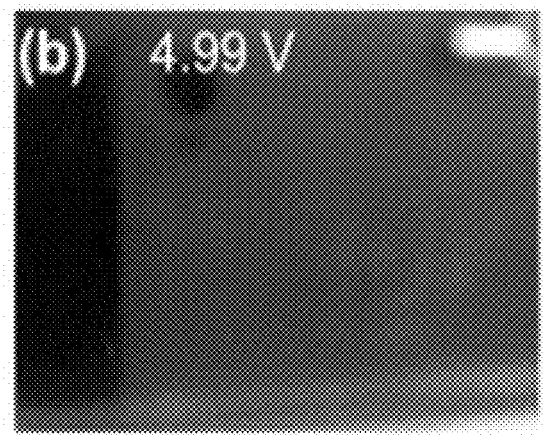
FIG. 13A
FIG. 13B
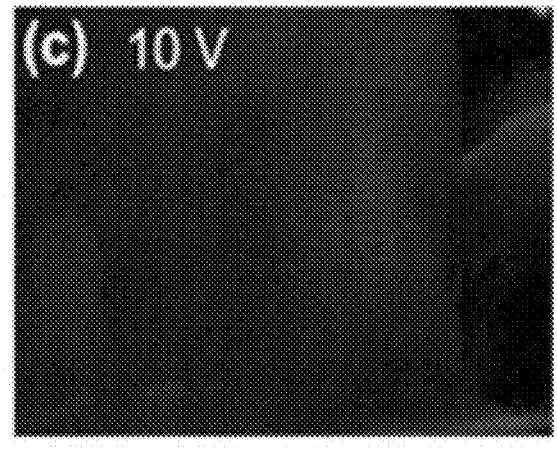
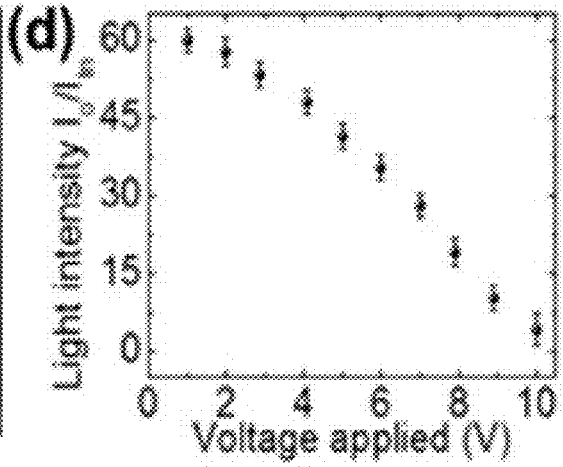
FIG. 13C
FIG. 13D

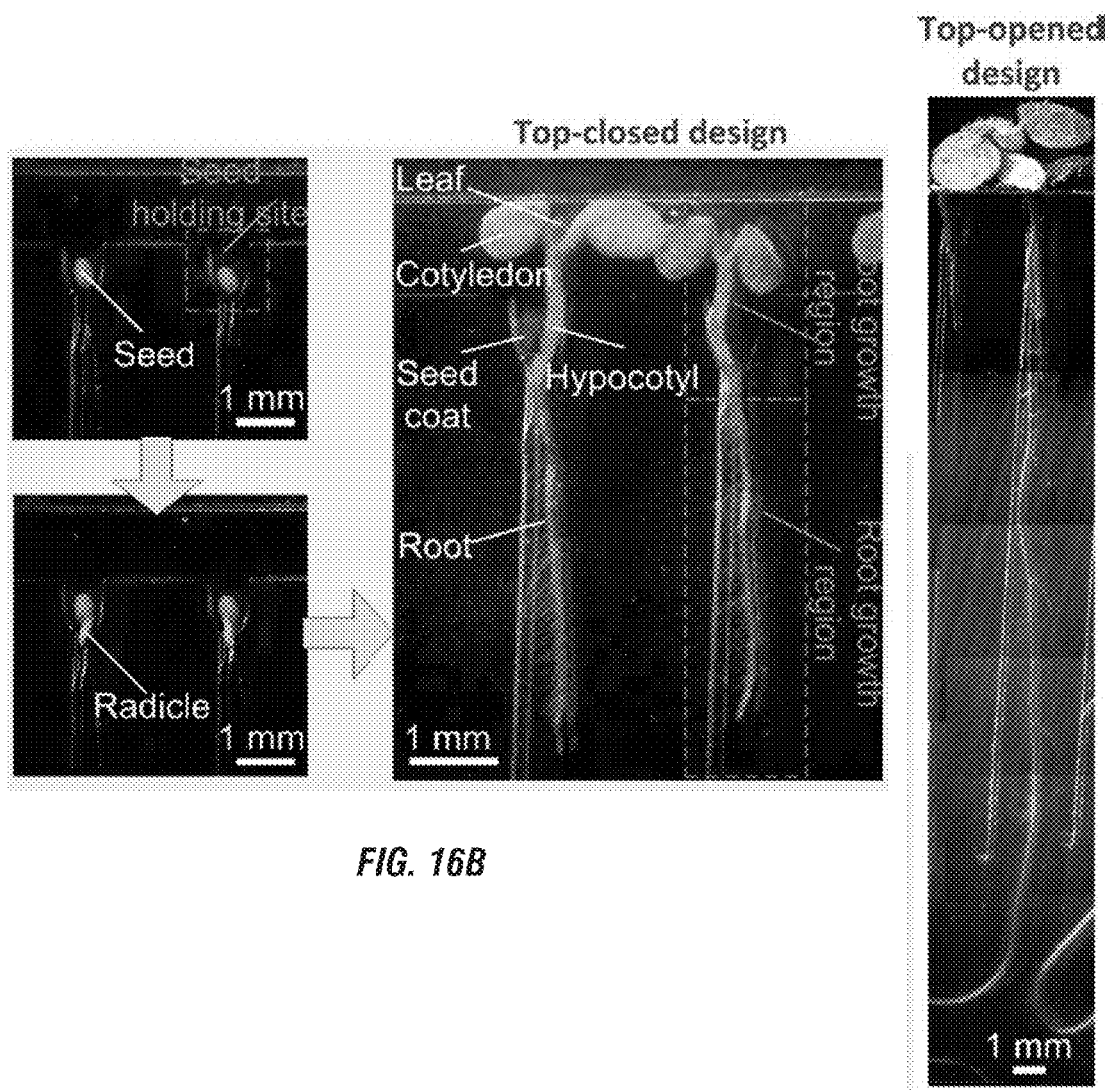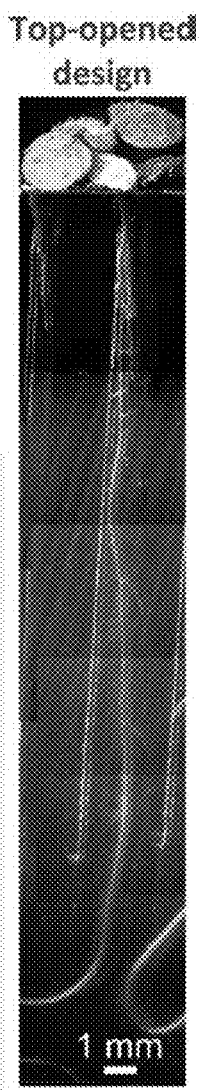
*FIG. 16B*
*FIG. 16C*

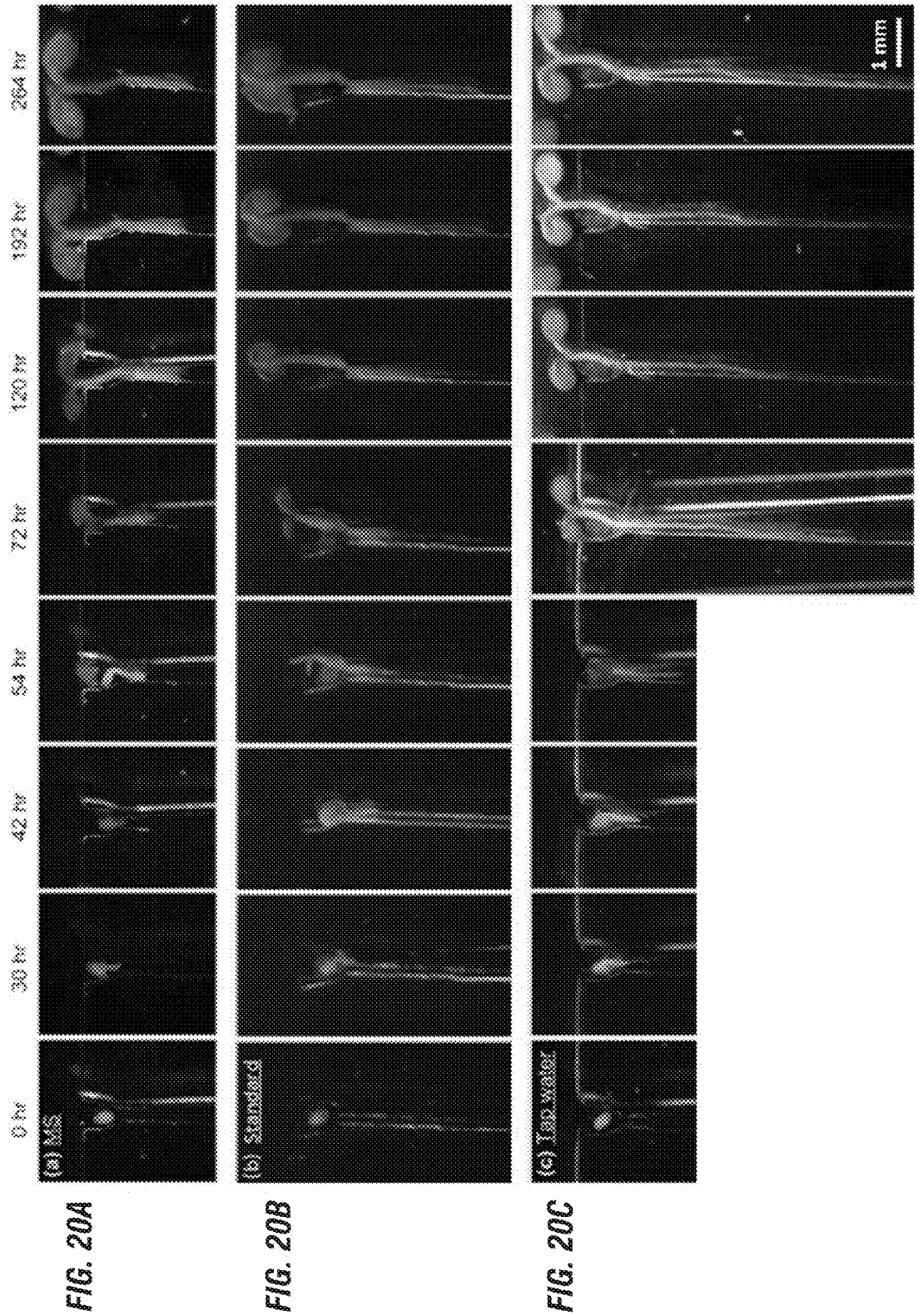

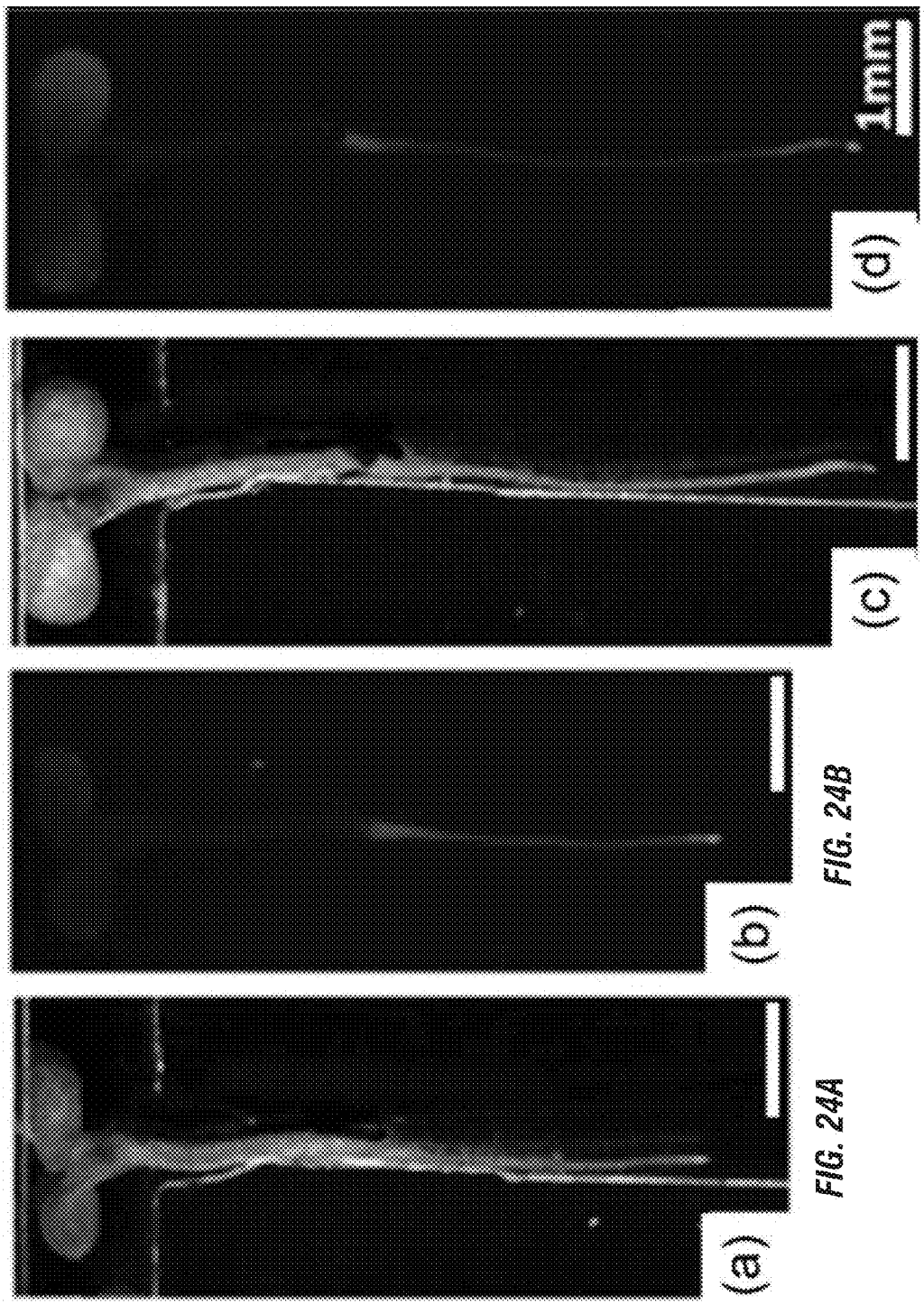

200 μm

HIGH-THROUGHPUT LARGE-SCALE PLANT PHENOTYPING INSTRUMENTATION

CROSS-REFERENCE TO RELATED APPLICATIONS

This application claims the benefit under 35 U.S.C. § 119 to provisional U.S. Application Ser. No. 62/011,395 filed Jun. 12, 2014, hereby incorporated by reference in its entirety.

GOVERNMENT GRANT CLAUSE

This invention was made with Government support under Grant Number DBI-1353819 awarded by the National Science Foundation. The government has certain rights to this invention.

I. BACKGROUND OF THE INVENTION

A. Field of the Invention

The present invention relates to apparatus and methods for high-throughput, large-scale sample testing instrumentation, systems, and methods and, in particular, for evaluating and screening sample/environment interactions including but not limited to plants for rapid discovery of genotype-to-phenotype correlations at high spatial and temporal resolution.

B. Problems in the Art

Genes in plants respond to environmental conditions (e.g. temperature, light, $CO_2$, salt, humidity, drought, pathogens, etc.). It is of great interest to discover phenotype/genotype relationships or other correlations based on environment conditions. A problem is that it is hard to analyze such things on large scale and in a fast time frame with resolution and precision. One approach is to grow a large number of plants in fields or greenhouses and try to measure phenotypic traits during their growth. This involves large amounts of growing space. It involves expensive labor and equipment to acquire data from the plants. It requires either reliance on nature for different growing conditions (e.g. grow the same plants in widely spaced fields to get different climates) or application of substantial amounts of growing factors (e.g. water, heat, etc.) in more controlled (e.g. greenhouse or plant growth chamber) structures. Both are expensive in terms of supplies, equipment, and labor, as well as energy costs. Both make it difficult to get fast acquisition of phenotype data.

Currently, plant phenomics studies rely mainly on culturing seeds and growing plants in soil pots and agarose plates using culture facilities (e.g., greenhouse and plant growth chamber) with controlled environments, and on using imaging technologies to measure plant characteristics and performance. While progress has been made, insufficient technical capacity imposes a strict limitation to conduct a large number of experiments for studying plant-environment interactions in a cost effective and timely manner. With the model plant *Arabidopsis*, for example, large-scale studies at high spatial/temporal resolution have been difficult for the cost and greenhouse needs, and thus, only few studies with a few thousand mutants have been done under specific environments.

Several high-throughput plant phenotyping facilities, such as the Australian Plant Phenomics Facility, Australian National University. Canberra, AU (see www.apf.an-u.edu.au) and the PhenoFab® system in the Netherlands, (see www.keygene.com), are currently available for phenomics studies. Controlled environments and automated imaging analysis are the two main technologies involved in these plant phenotyping facilities. The controlled growth environmental conditions (e.g., temperature, light, humidity, $CO_2$), provided by LemnaTec GmbH of Aachen, Germany (see, e.g., www.LemnaTec.com), are supported by a conveyor system for greenhouses and growth chambers. Specifically, the pots and plates with plants are moved through a growth compartment and scanned at preset time points from various angles to capture digital images. However, there are several concerns worth noting. First, screening of plant phenotypes using greenhouses or growth chambers is costly and the number of experiments is limited. Changing climate conditions of a greenhouse or plant growth chamber requires accessories such as a water spray system, heater, and air ventilation system. The flexibility, accuracy, and speed of changing environments are limited. These issues become exacerbated when multiple climate-controlled chambers are needed for growing plants in parallel under various environments (with each chamber providing a specific set of growth conditions). Second, due to the use of pots and plates, a relatively large amount of chemicals and biological species is needed. Energy consumption is another concern for using multiple growth chambers. Third, since current practices for monitoring root growth behaviors in laboratory are often limited to non-transparent soil pots and agarose plates, the resultant spatial resolution of morphological measurements for seed, root, and shoot phenotypes is on the millimeter scale. Microscopic real-time observation of cellular behaviors (e.g., cell division, elongation, host-pathogen interactions) on the micrometer resolution is not easy. Lastly, the low temporal resolution may lead to missing information about progressive and subtle changes in plant phenotypes during plant growth.

An example of issues with current methods is as follows.

Assume plant scientists want to develop new lines of corn that will better tolerate long stretches of hot, dry weather. How can they precisely assess the performance of those new plants in different environmental conditions? Field tests can provide some answers. Greenhouse tests can provide some more. But how can plant scientists get a true picture of a plant's growth and traits under a wide variety of controlled environmental conditions?

That has been too big and too precise for most laboratories. There are a few labs around the world that can do the work, but the studies are expensive, limited, and require time and labor. There has not been an accessible test instrument with enough scale, flexibility, and resolution to produce all the data scientists need.

II. SUMMARY OF THE INVENTION

The present invention includes what will sometimes be called a greenhouse on a chip—an instrument, and related method, that incorporate miniature greenhouses, microfluidic technologies that precisely control growing conditions, and robust data acquisition tools that help analyze plant information.

The instrument can be beneficially applied in the study of plant phenotypes—e.g. the look, size, color, development and other observable traits of plants. The instrumentation can be used for solving challenging, large-scale problems in the field of phenomics. It will benefit plant biology researchers and place powerful data analysis capability in the hands of researchers.

In one aspect of the invention, a system for high-throughput, large-scale plant phenotyping for screening of plant/ environment interactions comprises a plant growth platform sub-system which includes a plurality of small greenhouse structures for enclosing a controlled environment, each micro or miniature greenhouse including at least one substantially transparent window. A plurality of independently controllable generators provide environmental and plant growing factors to each miniature greenhouse. A control system is operatively connected to the generators and is capable of independent control of environment at each miniature greenhouse. A plant imaging sub-system comprises a high resolution digital imager and a robotic actuator to provide adjustable position and attitude of the imager relative each of the micro greenhouses for automated image acquisition of plants within each micro greenhouse through its window(s) with high resolution spatially and temporally. A processor with software algorithms receives the acquired images and can be used to evaluate them. One example is to quantify or determines phenotypic differences based on the acquired images. The quantified differences can be used for such things as correlation of differences in environment with phenotypic traits for a species or genotype-to-phenotype interactions for such purposes as plant phenomics, functional genomics, and systems biology. The system can be applied in analogous ways to animals, insects, or other living things.

In one aspect of the invention, the generators can either be on the micro greenhouse or off the micro greenhouse and generate in the micro greenhouses one or more highly controllable factors such as relative humidity; light intensity; $CO_2$ level; temperature; and growing medium, including but not limited to water; chemicals; hormones; pathogens; or combinations of two or more of the foregoing.

In another aspect of the invention the system can include sensors to sense or adjust the plant growing factor associated with a correlated generator and the imaging sub-system includes storage for still or video images at adjustable spaced apart times correlated to each and any of the micro greenhouses, and the images can be of whole plants or portions of plants including magnified or other than visible light images. Further, the imaging can be combined with other imaging or microscopy techniques. Examples are limited spectrum images; hyper spectral images; multi-spectral images; fluorescence images; infrared images; and x-ray images.

Another aspect of the invention relates to a method for assaying multiple biological items of interest for phenotype correlations comprising: creating an independently adjustable local environment for sets of one or more of the biological items; automatically controlling at least one controllable environmental factor to each set; automatically varying the controllable environmental factor between at least two sets; automatically acquiring data from each set relating to at least one phenotypic reaction to its environment for at least two separated times; comparing data between sets and times; and evaluating the comparisons to derive correlations between phenotypic trait and the local environments between sets of the biological items.

In one example the miniature greenhouse comprises an enclosure having at least one portion transparent to allow imaging of its interior, and at least one plate or chip having a perimeter, opposite sides having a height and width along a plane, and a relatively small thickness between opposite sides; a plurality of spaced-apart receivers having a larger opening on one side and a smaller opening on an opposite side, the receivers generally aligned across the width and formed internally in the plate, the larger opening allowing passage of at least an average-sized biological item of interest into a receiver, the smaller opening preventing an average-sized biological item of interest from passing out of the receiver so that the receiver is adapted to receive and seat a plant seed of interest at a receiver site within the plate; a channel formed in the plate in communication with the larger opening for each receiver, the channel generally in the plane of the plate; at least one inlet opening in communication between the exterior of the plate and the channel; at least one outlet opening in communication between the channel and the exterior of the plate; the plate being generally transparent at least from one opposite side and relative to the channel. Each plate or chip can be removably installed into the miniature greenhouse and exposed to at least one generator of growth factor either on or off the plate or chip; so that a biological item of interest can be seated in each seed receiver, growing medium supplied, and imaging of each biological item and growth can be taken through the transparent portion of the plate or chip and the miniature greenhouse to acquire spatial and temporal data about biological item/environment interaction.

In one aspect of the plate or chip, an automatic loading method can be used to automatically populate each receiver in the plate or chip with a biological item. First, a plurality of the biological items, typically more than the available number of receivers, are suspended in a flow of fluid through the channel of the chip. Second, the fluid flow is controlled to promote carrying of the biological items along the channel near the receivers and then deposit one biological item into each receiver. In one example, this is accomplished by controlled fluid flow dynamics both past and through the receivers in combination with the size and form factor of the receivers.

In another aspect of the invention, the miniature greenhouses, and any chips if used, can be scaled up or down depending on factors such as the size of the biological item of interest. In the case of some seeds and plants, the scale is on the order of millimeters. But it can be scaled up or, in some cases, down.

An aspect of the invention according to some applications is the use of a microfluidic channel network and microfluidic control logic to deliver environmental factors to each miniature greenhouse and to each biological item in each miniature greenhouse. Such microfluidics can be partially inside and partially outside the miniature greenhouse, and can include microfluidic pumping and valving.

In one example, humidity is regulated by a channel with an open side carrying water to at or near the chip; a sensor to sense relative humidity at or near the chip, and communication between the sensor, a controller and an actuator to regulate supply of water to the channel. In one example, temperature is regulated by an electric heater and temperature sensor at or near the chip; and communication between the temperature sensor, a controller, and an electrical power source to regulate operation of the heater. In one example, light intensity is regulated by a liquid crystal element and a light intensity sensor between the chip and an external light source; and communication between the sensor, a controller, and an actuator to control the liquid crystal element between opaque and transparent.

In another aspect of the invention, chemicals, pathogens, or other substances are delivered at or near the receivers or channel above the receivers by actuators controlling movement of said substances or carriers of said substances through microfluidic channels. When plants are the biological item of interest is delivery of $CO_2$ an example is a $CO_2$ generator comprising one or more channels in communication with supplies of chemicals that when mixed react and produce $CO_2$ and a $CO_2$ sensor in communication with a controller to instruct an actuator to regulate generation of $CO_2$ at or near the chip by mixing the chemicals in the channel and then supplying the $CO_2$ to the receivers through the channels in the chip. Other substances can be delivered to the miniature greenhouse or chip.

The instrument's capabilities are significant to researchers: For example, the system will largely facilitate plant phenotyping experiments that are impossible by current techniques. It can also be used in different applications. For example, it could be used to study germination of pollen at different temperatures, or how fungal pathogens interact with soybean seeds at different moisture levels. It could be used beyond plants. Examples are for studies of insects or even small fish.

The phenotyping system disclosed here can solve problems mentioned above for screening of plant growth-environment interactions. The system can largely facilitate plant phenotyping experiments that are impossible by current techniques, constituting a significant leap in throughput and information content over existing plant phenotype assays. These capabilities are important in providing key insights into the genetic control of plant growth, health, and quality at the organismal level, as well as plant genotypes that produce valuable traits. The system can lead to rapid discovery of various phenotypes and the underlying genes that control the phenotypes under different environments, and thus, can benefit wide range of researchers.

Expected commercial applications include but are not limited to:

Similar to high-throughput biotechnologies such as microarrays and next-generation sequencing that have made it possible to acquire a great wealth of information about the genotypes of plants, the instrumentation disclosed here can help users to obtain information about the phenotype of plants in general.

Plant genetic engineering companies are interested in the disclosed technology.

Seed companies need the disclosed phenotyping instrumentation to rapidly identify test seeds at various environmental conditions.

Research laboratories in plant biology community (e.g., functional genomics, phenomics, etc.) need the disclosed system for scientific studies.

Overall, the system allows for high-throughput screening plant-environment interactions for rapid discovery of a variety of phenotypes and the underlying genes and environments that control these phenotypes at high spatial and temporal resolution.

Large and multi-scale phenotyping of plants, in concert with changeable growth environmental influences, has broad implications in applied and basic plant biology. Characterization of the complete plant phenome poses a difficult challenge due to the large number of genes in the genome(s), and changeable environmental conditions that influence plant phenotypes. Because of this inherent complexity, analyzing plant phenotype(s) on a large and multi-scale level with sufficient throughput and resolution has been difficult and expensive. The large-scale, high-throughput plant phenotyping instrumentation will constitute a significant leap in throughput and information content over existing phenotype assays. The modularized and arrayed design of the instrumentation enables users to not only program desired environmental variables, but also scale up and down the dimensions of the integrated plant growth system, to phenotype different plant species growing to different stages of interest. Thus, the instrumentation contributes to systematic analysis of plant phenotypes with a wide range of applications in gene identification, functional genomics, and genotype-to-phenotype correlations.

III. BRIEF DESCRIPTION OF THE DRAWINGS

In addition to this written description, illustrations in the form of figures and drawings are appended which will be referred to from time to time in this description, and are summarized below.

The patent or application file contains at least one drawing executed in color. Copies of this patent or patent application publication with color drawing(s) will be provided by the Office upon request and payment of the necessary fee.

Figure 7A:
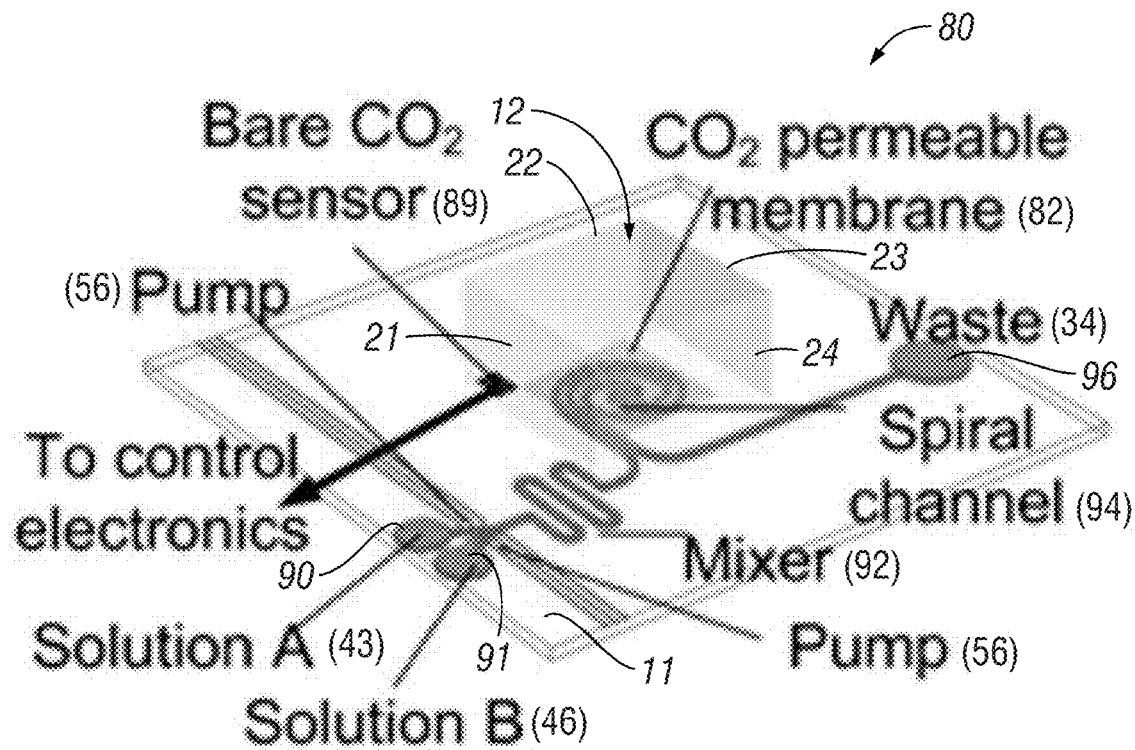
FIG. 7A is a greatly enlarged diagrammatic perspective view depiction of the CO2 generator of the MGH of FIG. 4B.
Figure 7B:
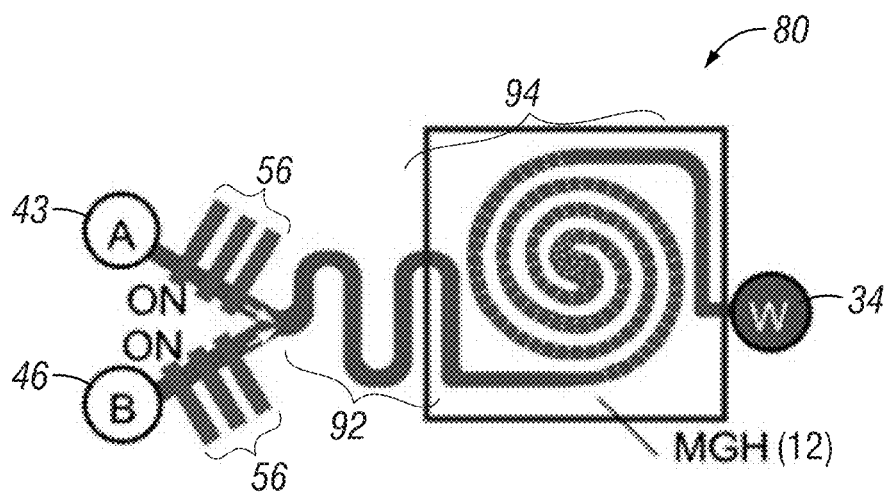
Figure 7C:
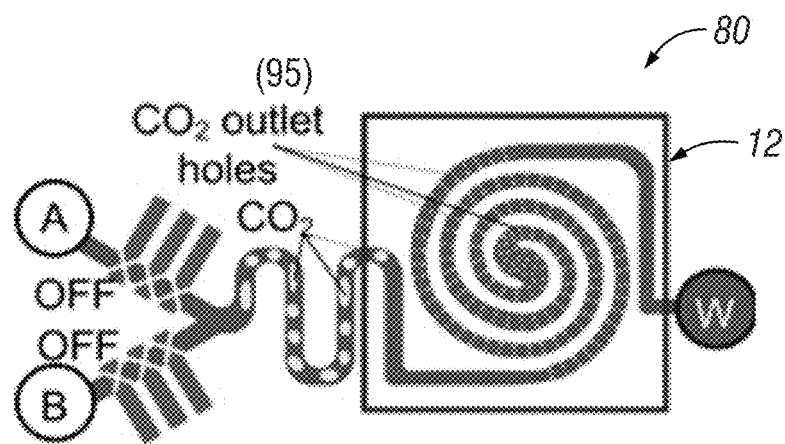
Figure 7D:
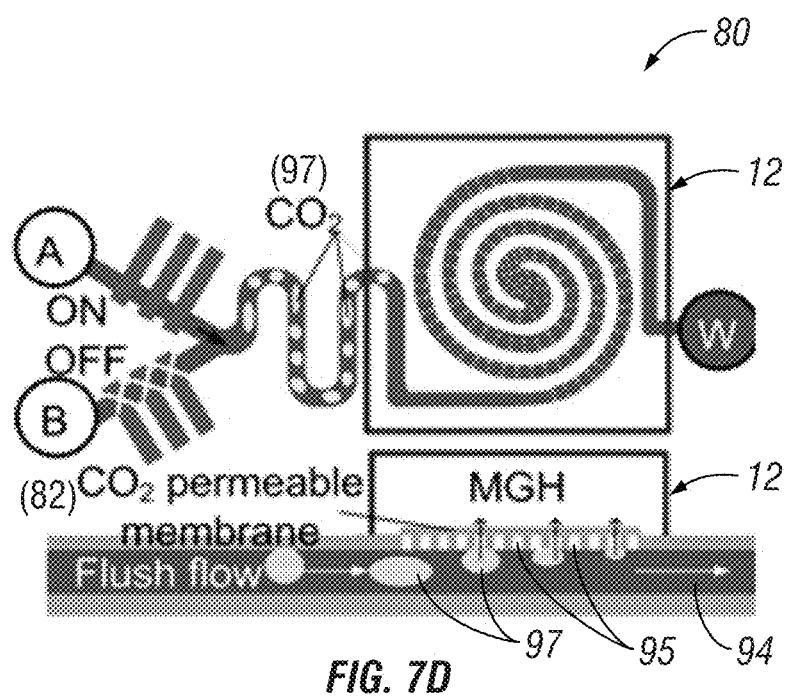

FIGS. 7B-D show various states of the CO2 generator of FIG. 7A. FIG. 7B shows a first state where microfluidic pumps are turned on to pump solutions A and B to a first portion of the generator. FIG. 7C shows the pumps turned off but mixing of the solutions A and B to produce CO2 gas in the first portion. FIG. 7D shows the pump for solution A turned back on to push the CO2 to the second flow portion where it is released through openings to the flow channel and through a hydrophobic membrane to the interior of the MGH.

Figure 4A:
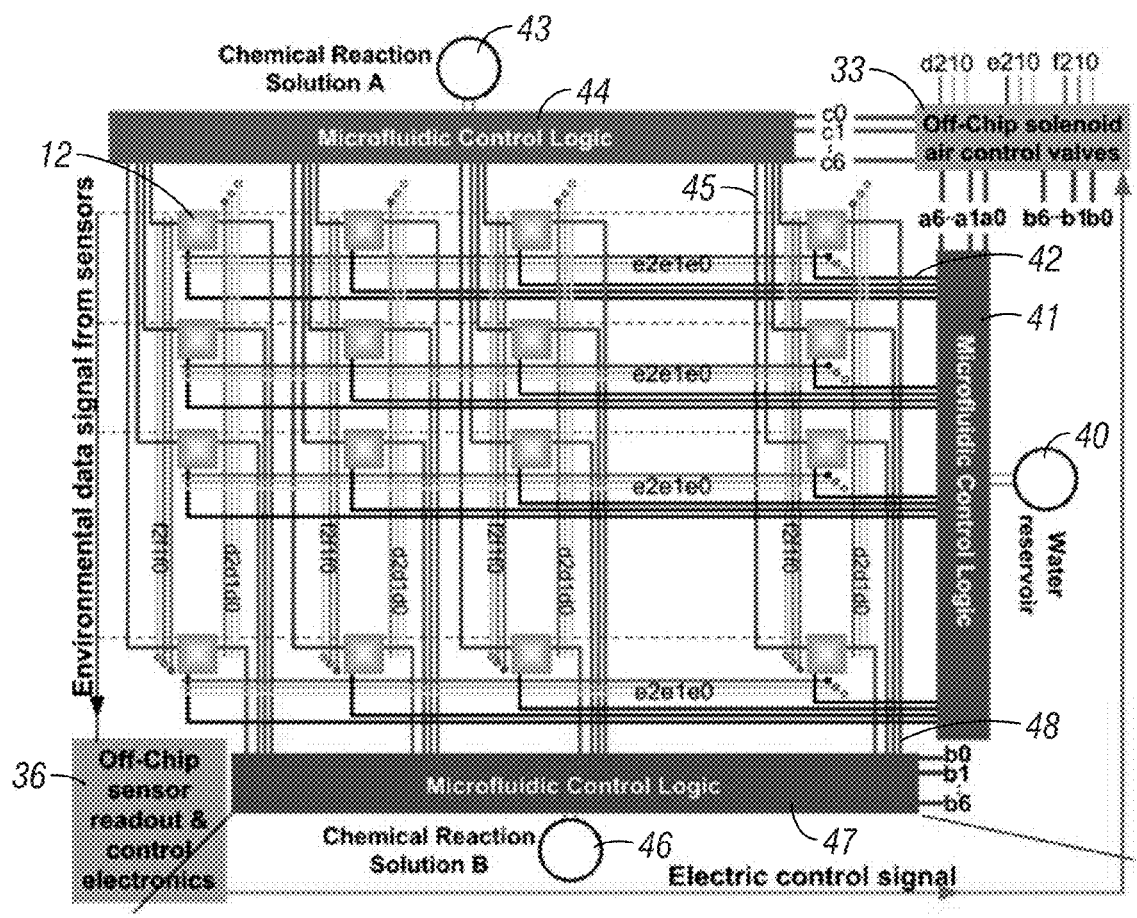
FIG. 4A is a microfluidic control logic diagram for a microfluidic circuit for providing fluids (gas and liquid phases) to the system of FIG. 3.
Figure 4B:
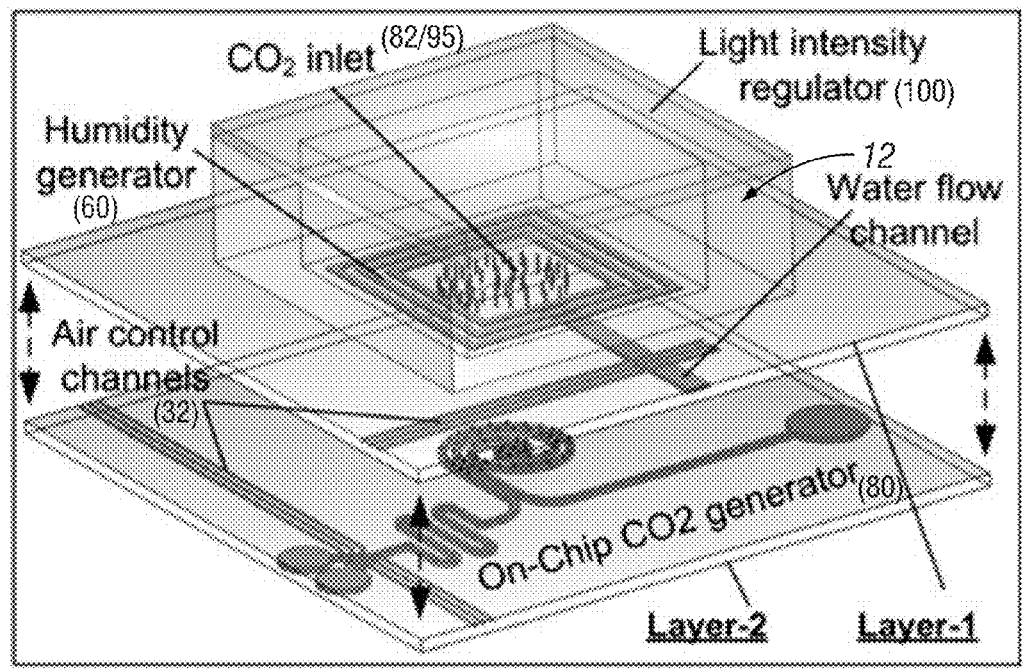
FIG. 4B is an enlarged, partially exploded view of one of the MGHs of FIG. 3.
Figure 8:
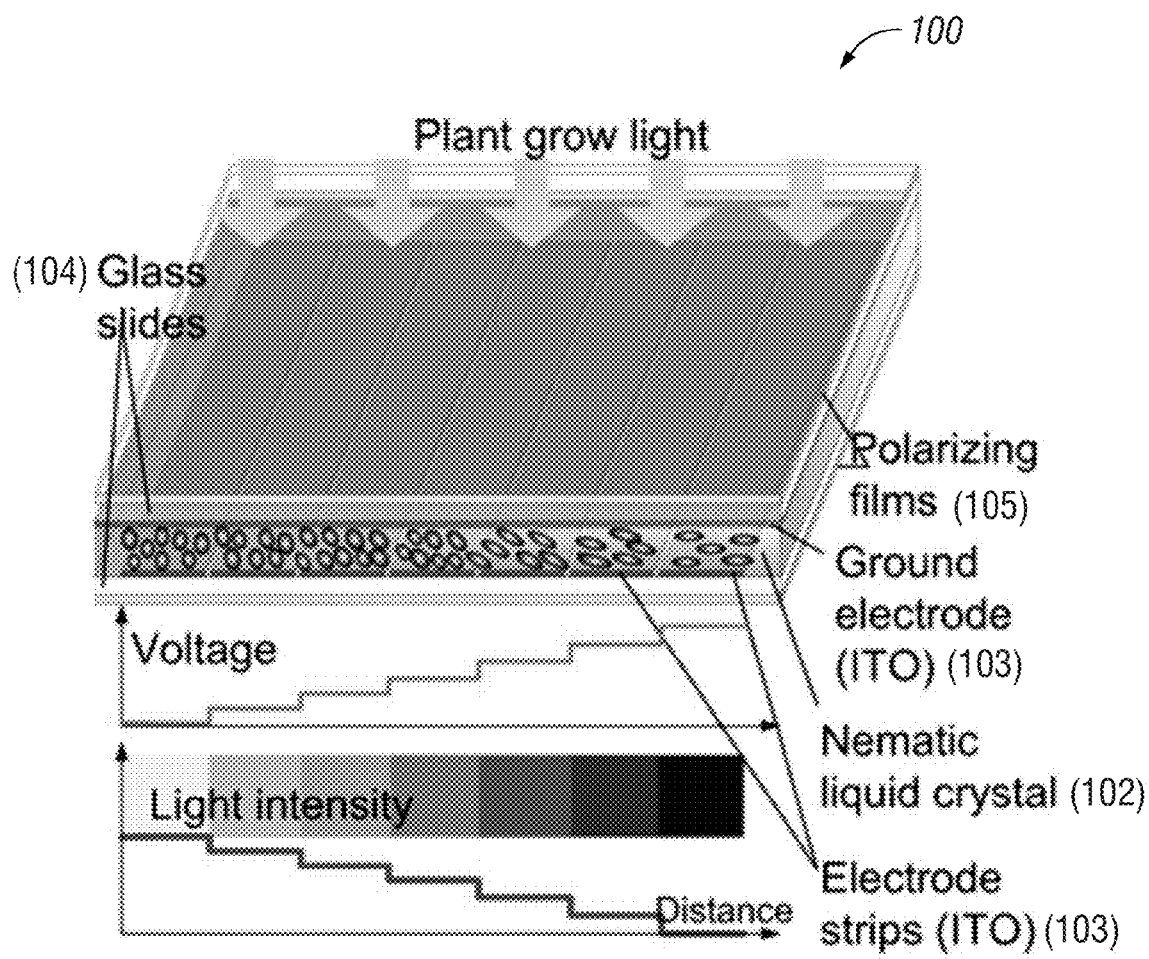

FIG. 8 is a greatly enlarged diagrammatic perspective view depiction of the light intensity regulator of the MGH of FIG. 4B, including a set of graphs showing operation of the regulator.

Figure 9A:
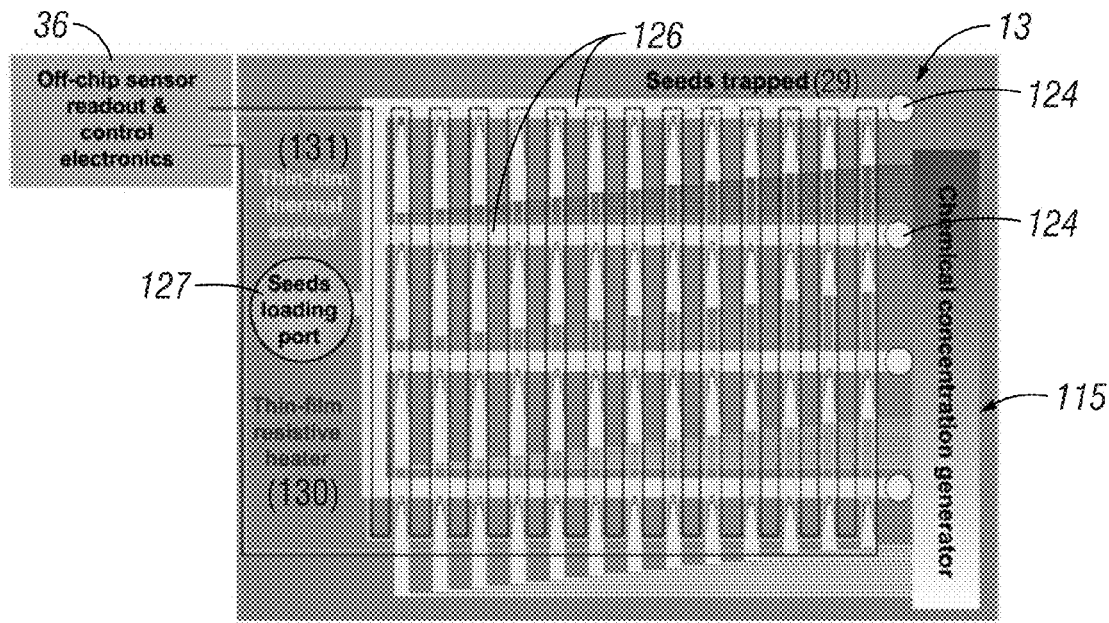

FIG. 9A is a diagrammatic elevation illustration of one MSC and a technique for automatically loading plant seeds into individual seed sites or receivers distributed in the MSC by microfluidics.

Figure 9B:
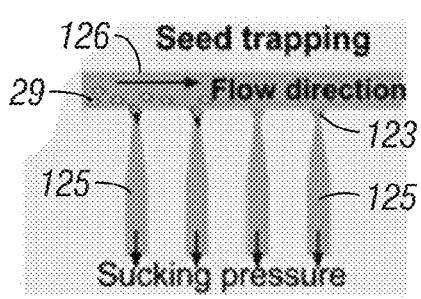

FIG. 9B is a diagrammatic illustration of use of positive and negative pressure in the automatic seed loading technique of FIG. 9A.

Figure 9C:
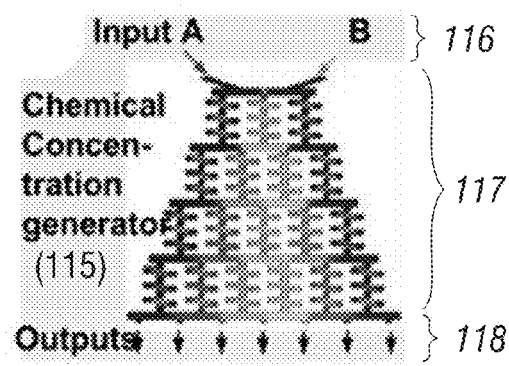

FIG. 9C is a diagram illustrating a chemical concentration generator technique that can be used to regulate chemicals into an MSC with microfluidics.

Figure 9D:

FIG. 9D is a series of temporally-spaced color images of a single seed developing into a plant in an MSC such as FIG. 9A from a front elevation perspective.

Figures 9E, 9F:
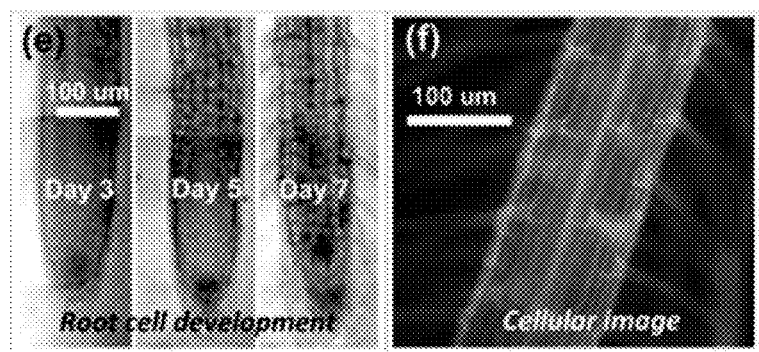

FIG. 9E is series of temporally-spaced enlarged, isolated color images of just the roots of the plant of FIG. 9D from a front elevation perspective.

FIG. 9F is a greatly enlarged color image, at a cellular level, of one of the roots of FIG. 9E from a front elevation perspective.

Figures 9G, 9H:
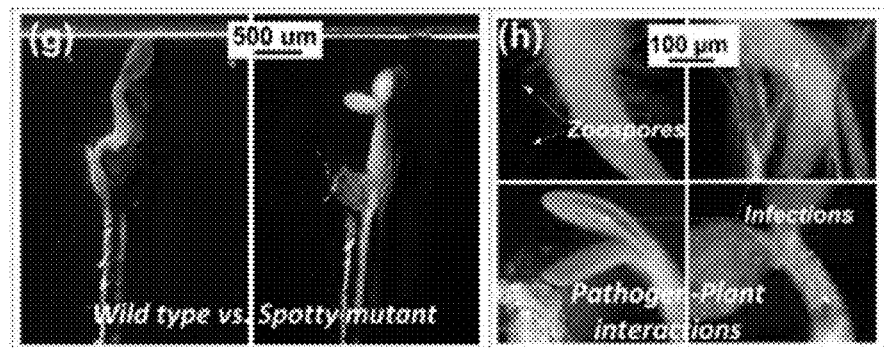

FIG. 9G are side-by-side color images of two different growing plants (e.g. differing in genotype) from different MSCs such as FIG. 9A taken at roughly the same stage of growth to compare how each has reacted to its MGH environment, which can be the same or different from one another, from a front elevation perspective.

FIG. 9H are side-by-side color images to show pathogen-plant interactions, from a front elevation perspective.

Figures 9I, 9J:
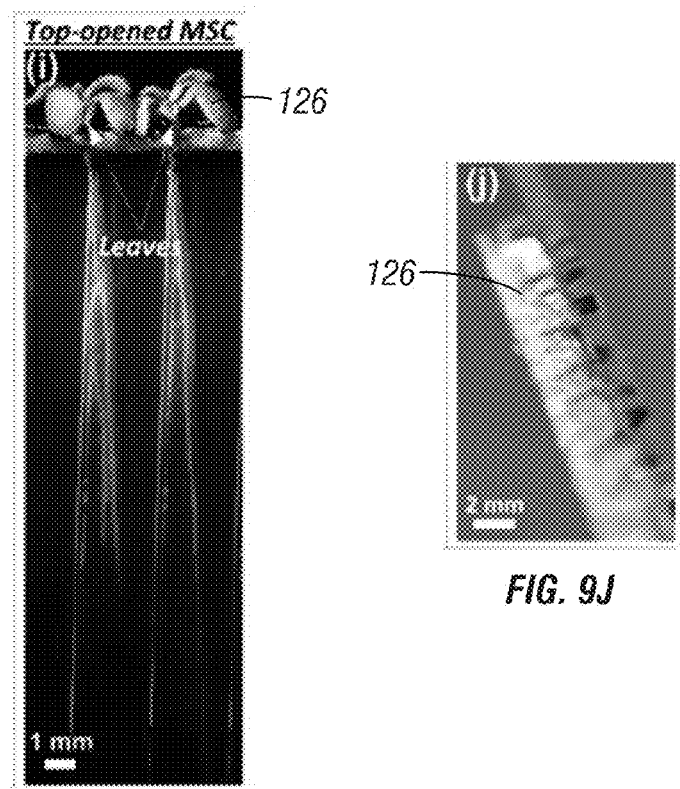

FIG. 9I is a color image showing a modified MSC that has been opened to allow not only root growth but shoot growth, from a front elevation perspective.

FIG. 9J is a color image, enlarged from FIG. 9I from a top edge perspective of the MSC, showing the shoots expanding from the open top of the MSC.

Figure 6A:
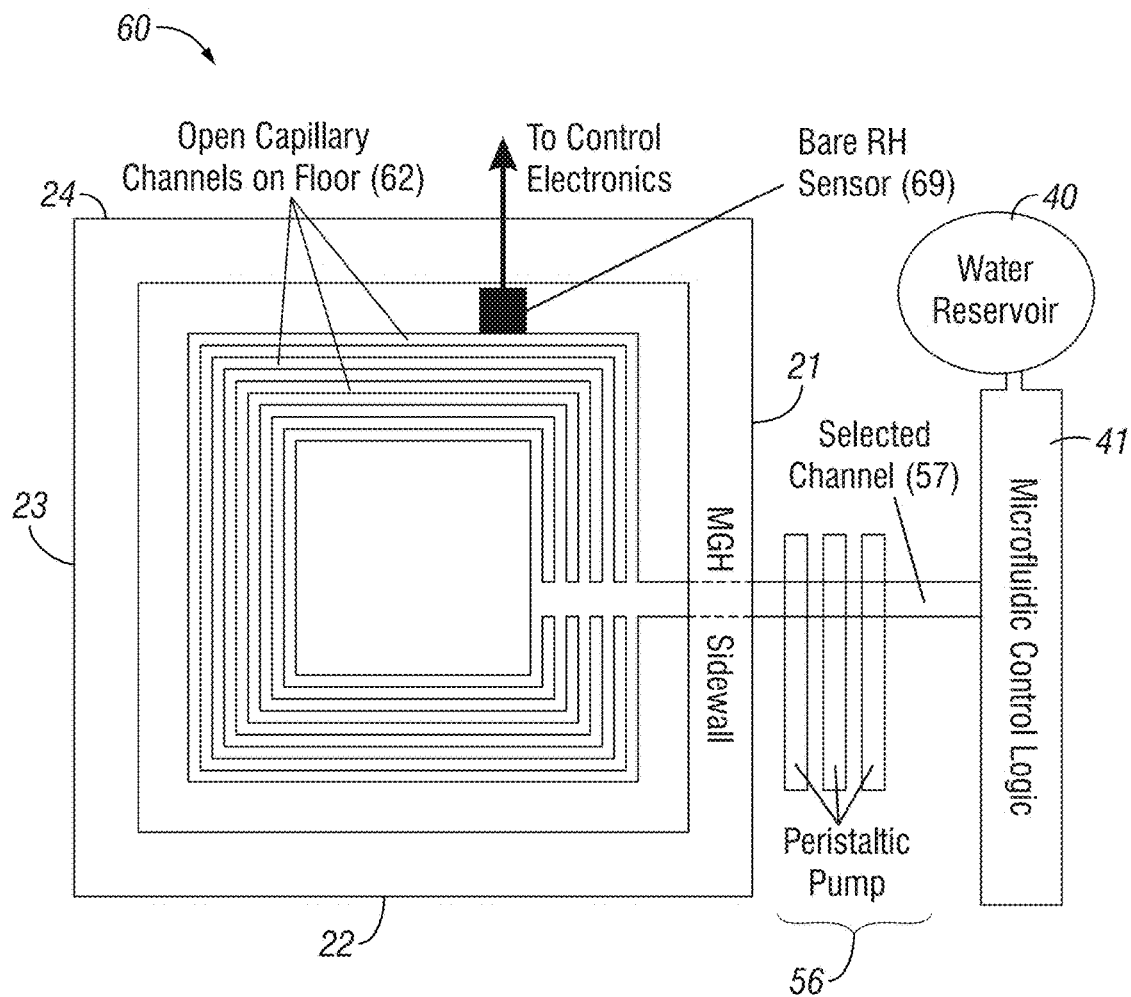
FIG. 6A is a greatly enlarged diagrammatic plan view depiction of the humidity generator of the MGH of FIG. 4B, including microfluidic control logic for a fluid pump.

FIG. 10A-D are vertical sectional views illustrating the layers and construction of the humidity regulator of FIG. 6A. FIGS. 10A-C show the layers in isolation. FIG. 10D shows the layers assembled.

FIG. 10E-G are vertical sectional views illustrating the layers and construction of the $CO_2$ regulator of FIGS. 7A-D. FIGS. 10E-F show the layers in isolation. FIG. 10G shows the layers assembled.

FIG. 10H-I are vertical sectional views illustrating the layers and construction of the light intensity regulator of FIG. 8. FIGS. 10H-I show the layers in isolation. FIG. 10J shows the layers assembled.

FIG. 10K is an assembled view of an entire MGH.

Figure 11A:
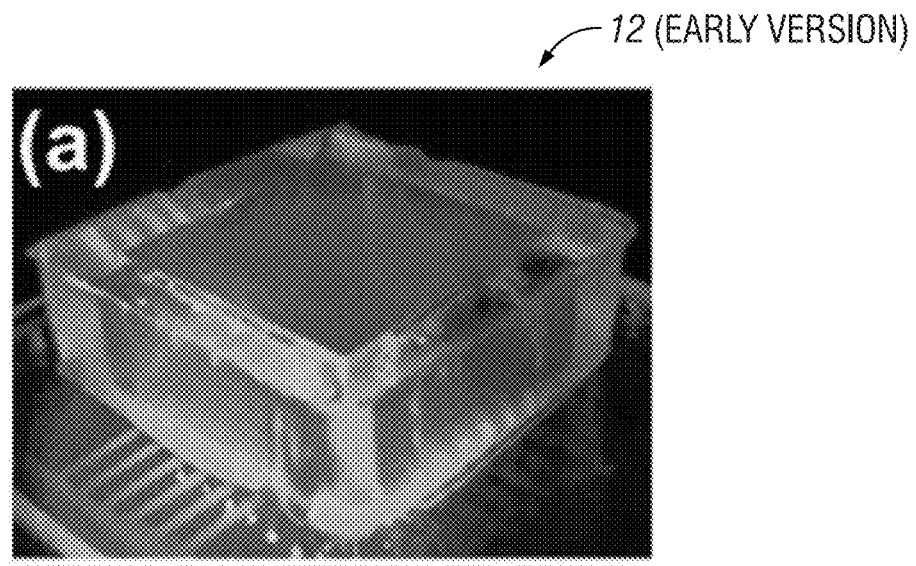

FIG. 11A is a color image of another embodiment of a MGH having a humidity regulator with a feedback sensor.

Figure 11B:
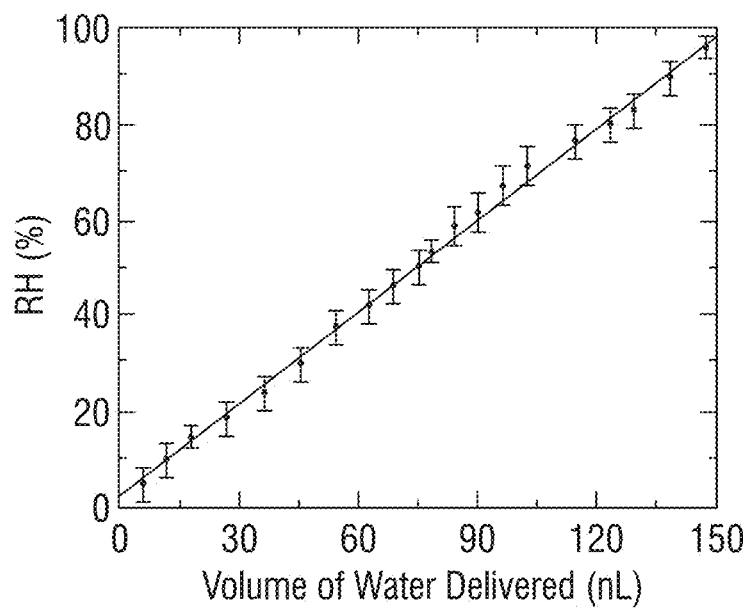
Figure 11C:
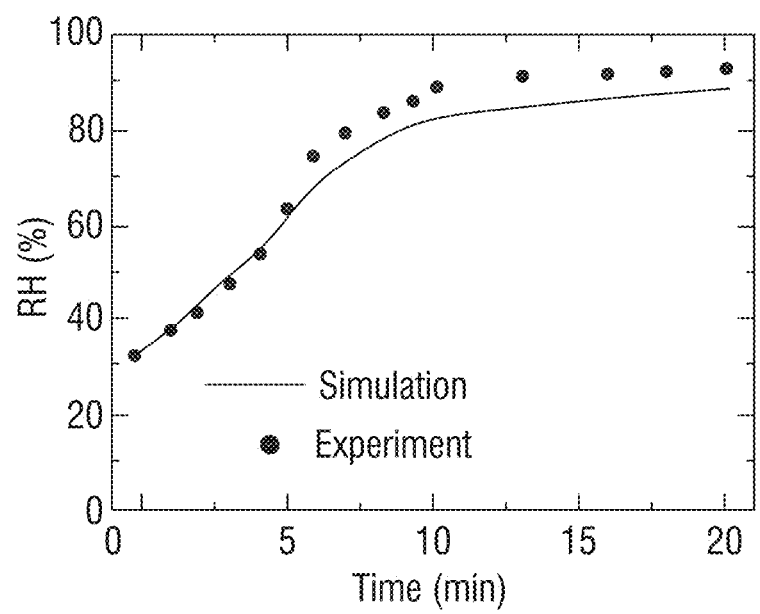
Figure 11D:
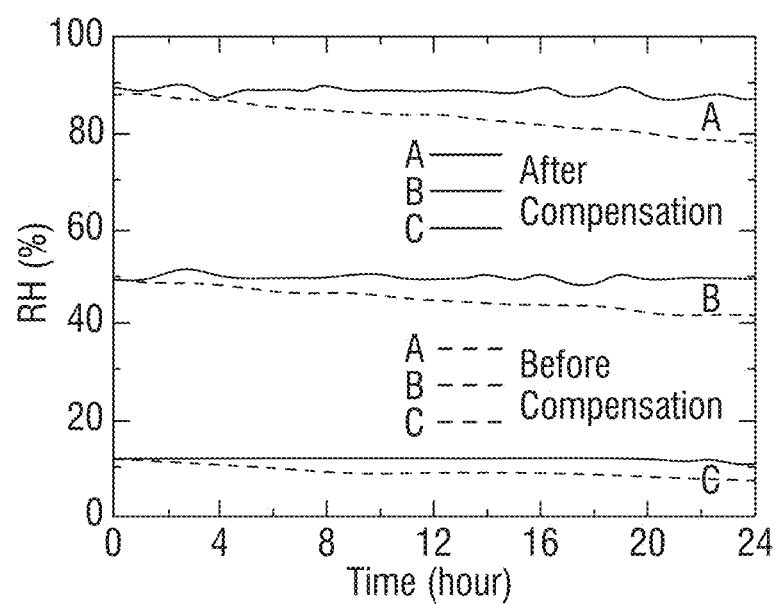

FIGS. 11B-D are measured data regarding performance of the humidity regulator.

Figure 12A:
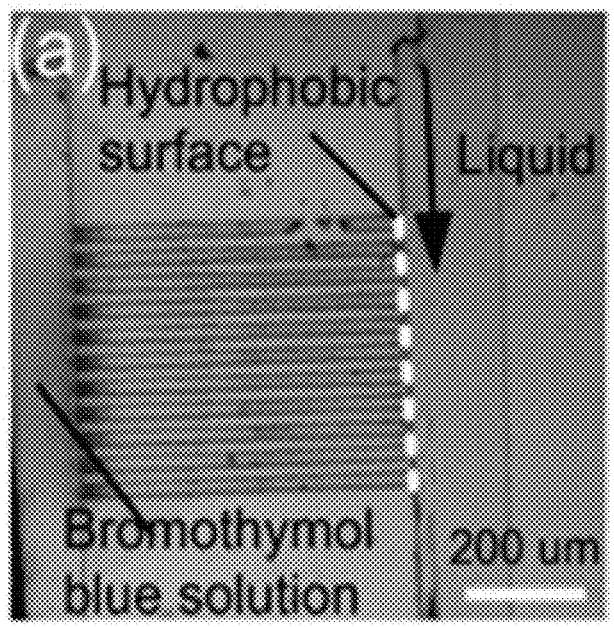
Figure 12B:
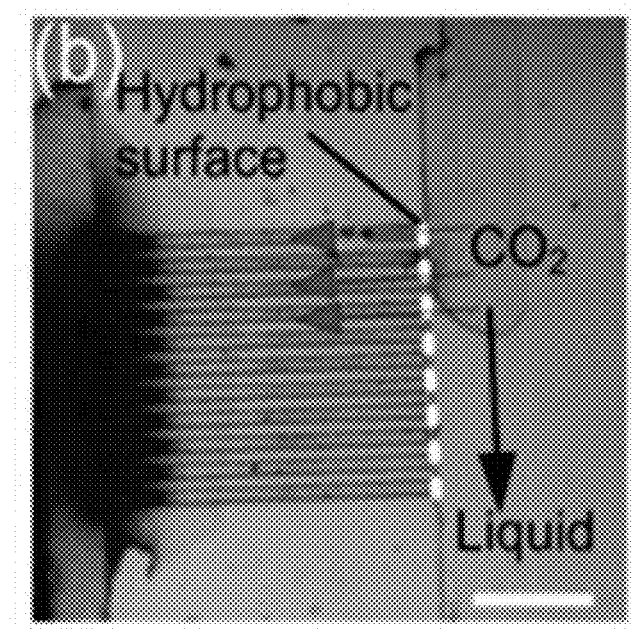
Figure 12C:
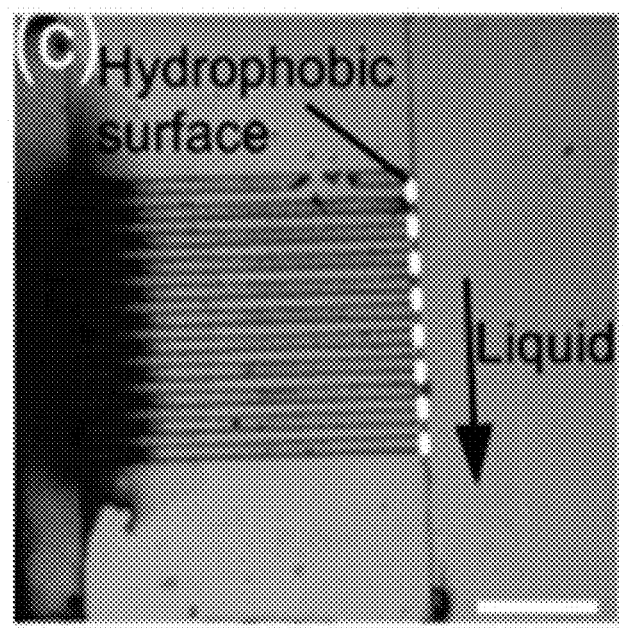

FIGS. 12A-C are color images and annotations illustrating CO2 generation with a generator like FIGS. 7A-D.

Figure 12D:
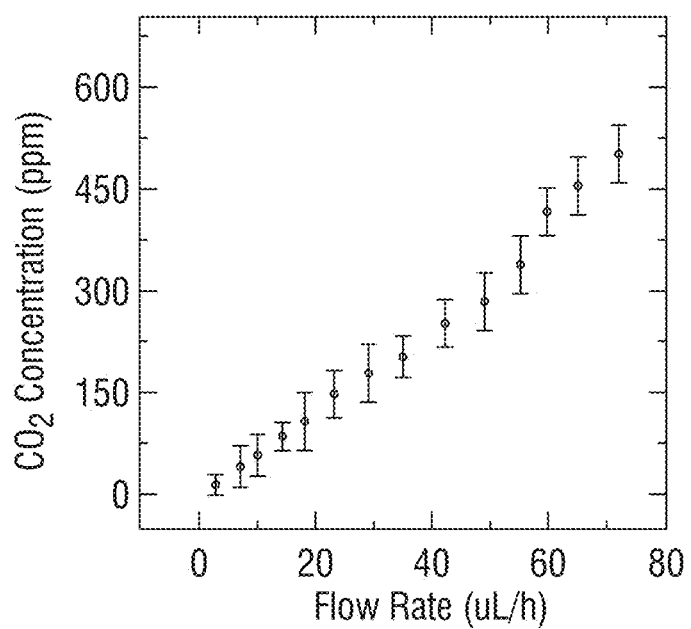

FIG. 12D is a graph showing performance of the generator of FIGS. 12A-C.

FIGS. 13A-C are color images and annotations illustrating light intensity regulation with a regulator like FIG. 8.

FIG. 13D is a graph showing performance of the regulator of FIGS. 13A-C.

Figure 14A:
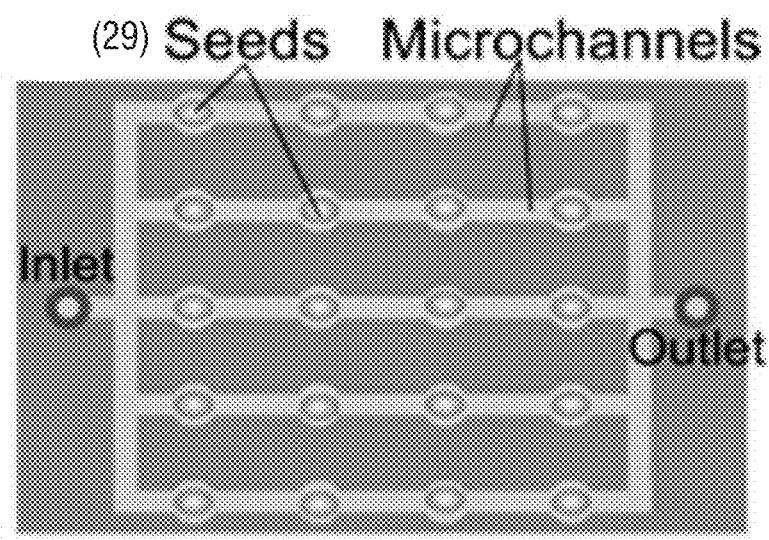

FIG. 14A is a diagrammatic illustration of an alternative embodiment MSC with multiple seed sites but without root or shoot growing chambers and microfluidic channels to and from those sites.

Figure 14B:
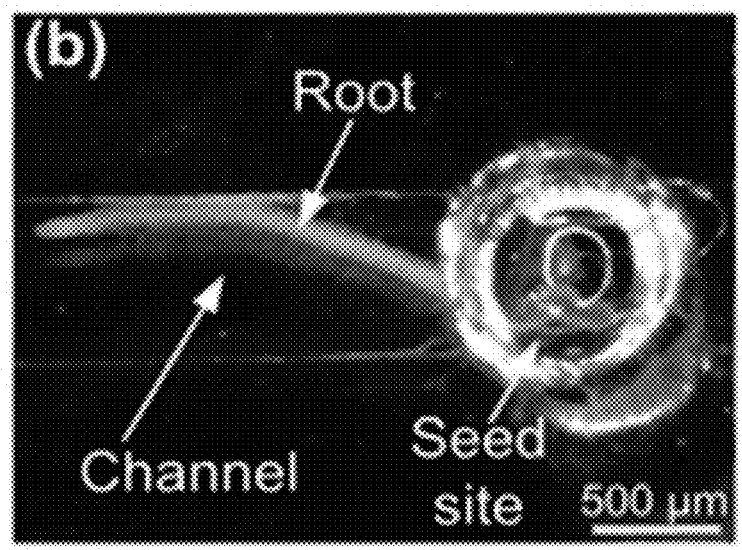

FIG. 14B is a color image of one seed site of the MSC of FIG. 14A showing how the root is growing sideways in the microfluidic channel.

Figure 14C:
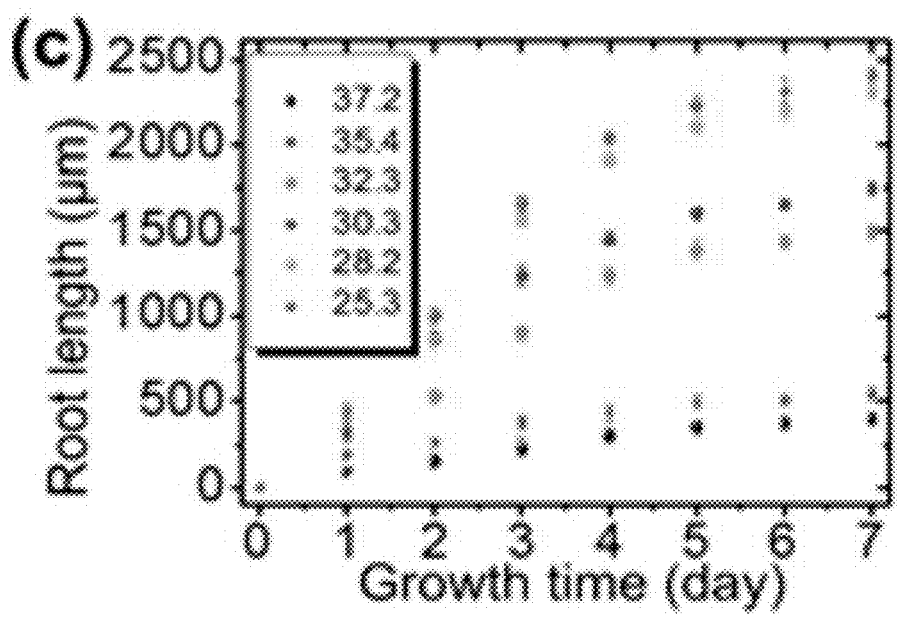
Figure 14D:
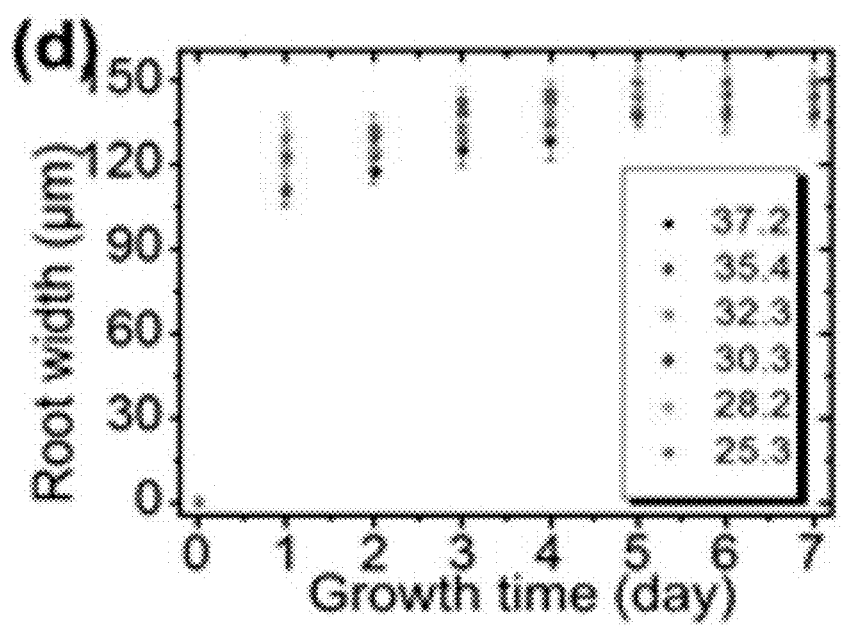

FIGS. 14C and 14D are graphs illustrating root length and width over time in the MSC of FIG. 14A.

Figures 15A, 15B:
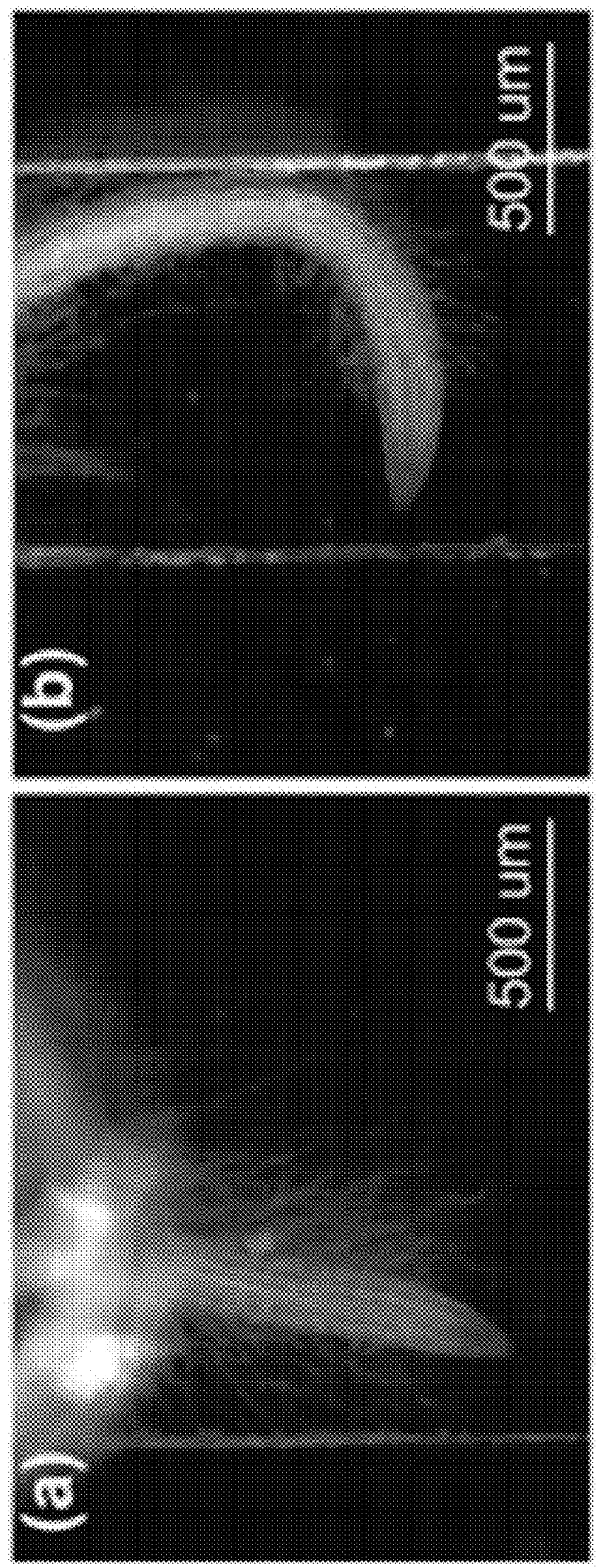

FIGS. 15A and 15B are color images at microscopic scale of the same plant root in situ in a MSC separated in time (two days apart).

Figure 16A:
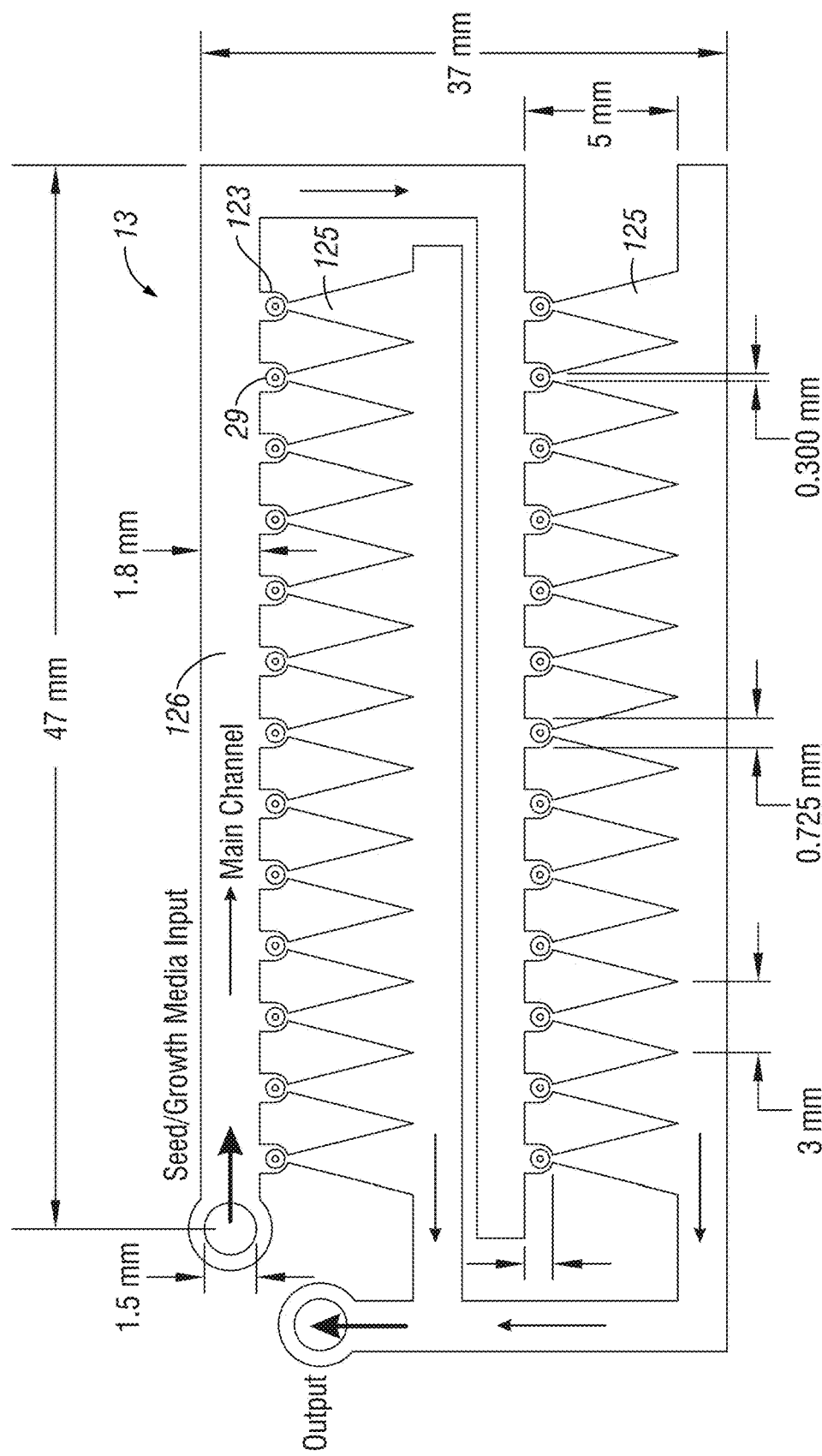

FIG. 16A is a diagrammatic illustration (not to scale) of the basic configuration of a two row MSC closed top design with both root and shoot growth spaces above and below each seed site, as well as the channels to supply growth media to each site.

FIG. 16B are color images of two adjacent seed sites in the MSC of FIG. 16A but showing plant development at three different times (first seed placement at the site, radicle root development, and then further root plus leaf development, respectively.

FIG. 16C is a color image of adjacent plants growing in an open top design chip.

Figure 17A:
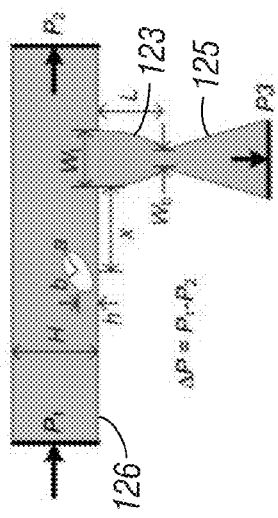

FIG. 17A is a diagrammatic illustration of a single seed site in a MSC like FIG. 16A, with specific annotated dimensions of the main channel, the seed receiver at the site, and a portion of the tapered root growth chamber below.

FIGS. 17B-H are each color images of simulated fluid dynamics during hydrodynamic seed trapping at the site to demonstrate the technique.

Figure 17B:
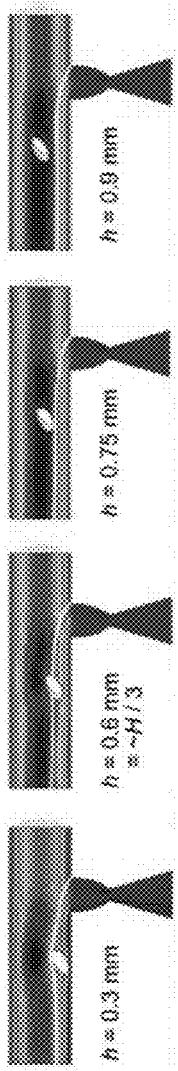
Figure 17C:
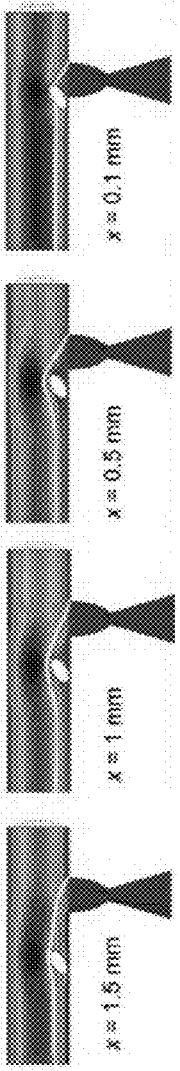
Figure 17D:
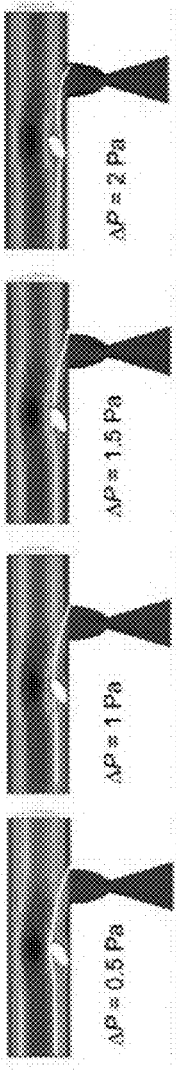
Figure 17E:
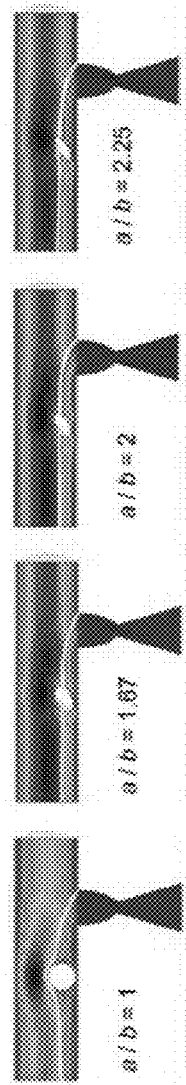
Figure 17F:
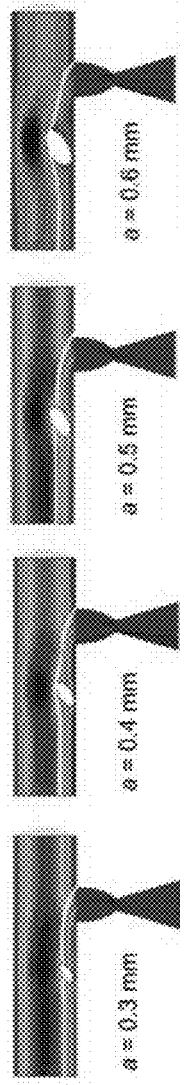
Figure 17G:
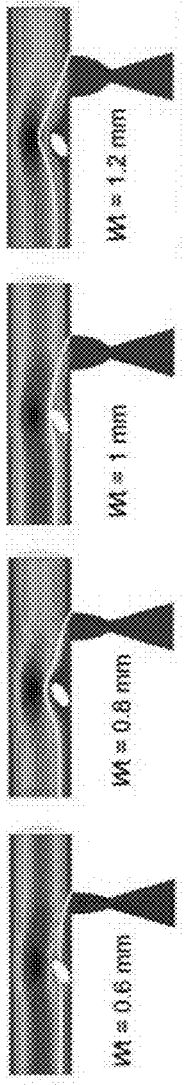
Figure 17H:
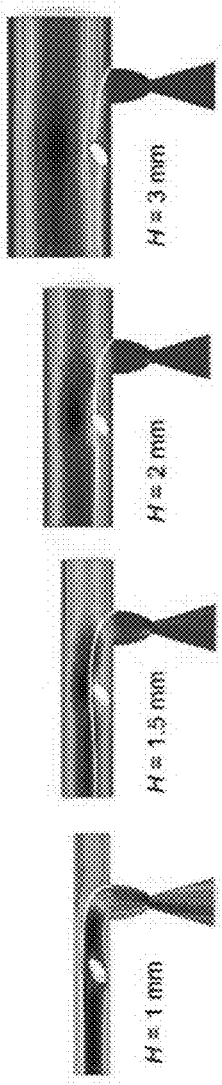
Figure 18A:
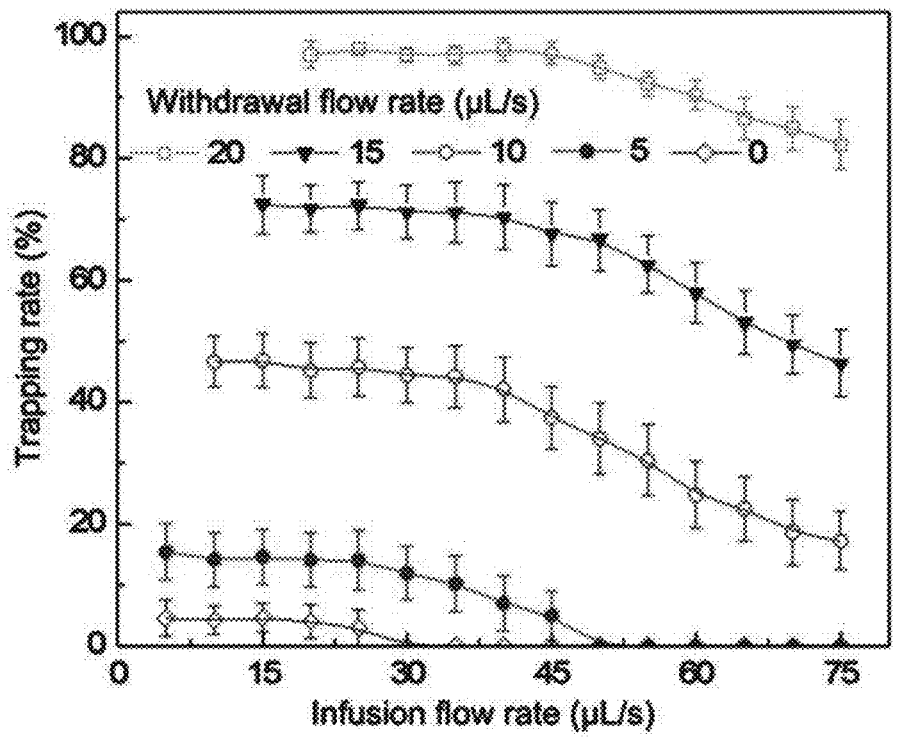
Figure 18B:
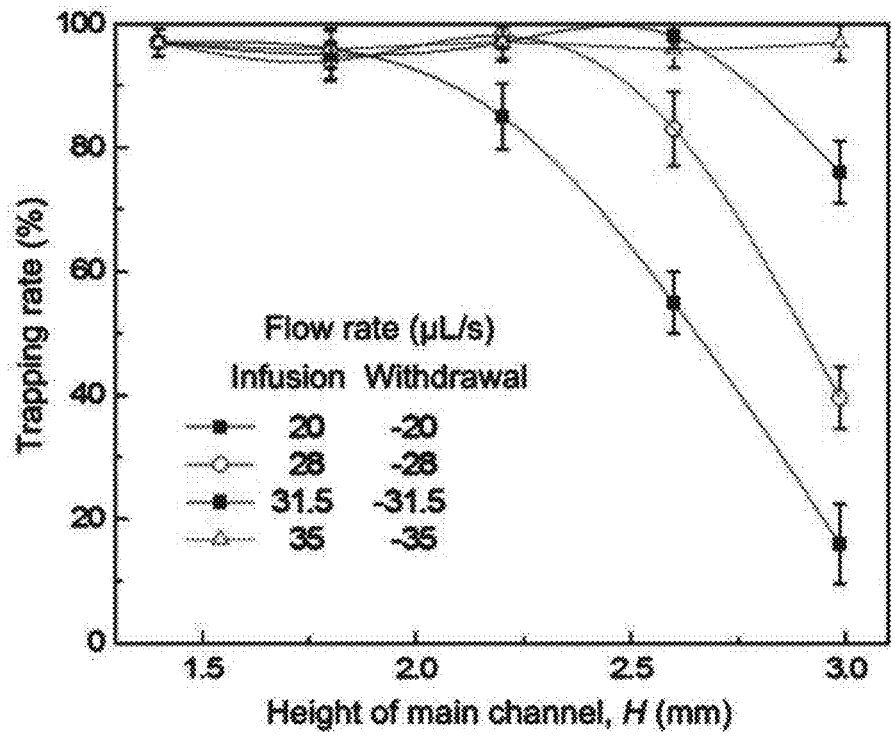

FIGS. 18A-B are graphs demonstrating performance of the seed trapping of FIGS. 17A-H.

Figure 19A:
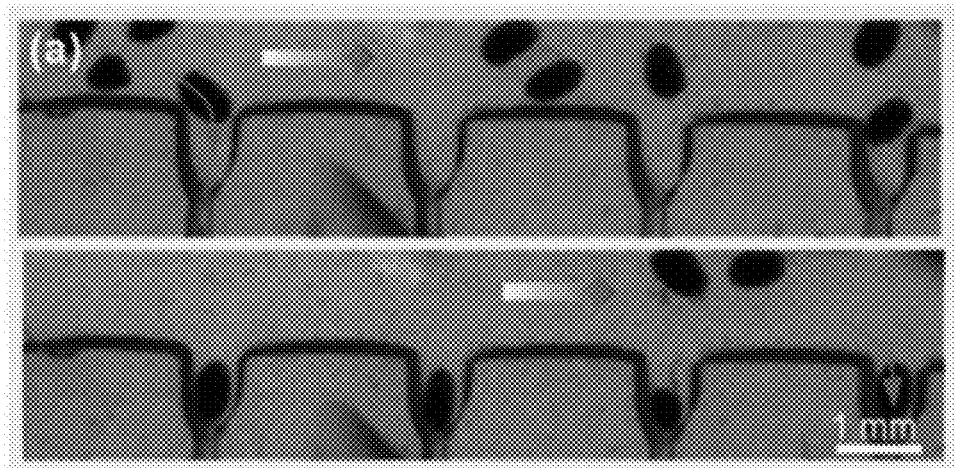
Figure 19B:
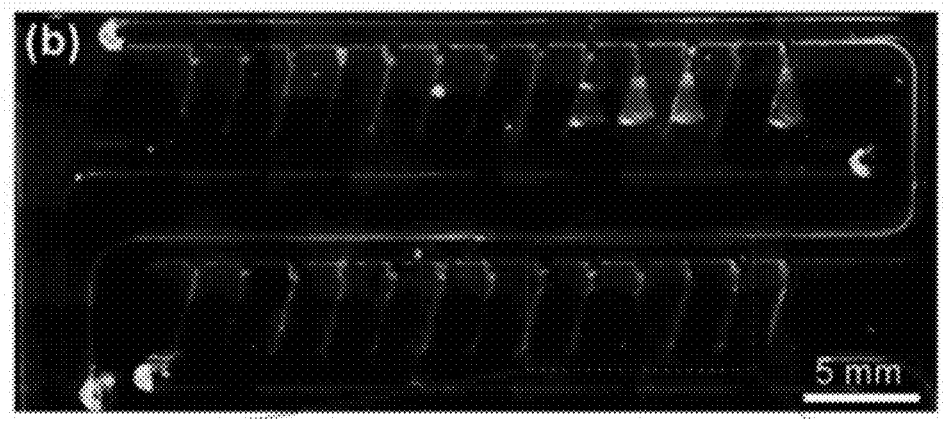
Figure 19C:

FIGS. 19A-C are color images of showing seed trapping in a MSC.

FIGS. 20A-C are each a series of color images taken at the same time intervals during plant growing in a MSC, but of different plants in different environments (e.g. different water/nutrient provided), allowing side-by-side visual and digital image processing comparison of differences in phenotypic traits with time.

Figure 21A:
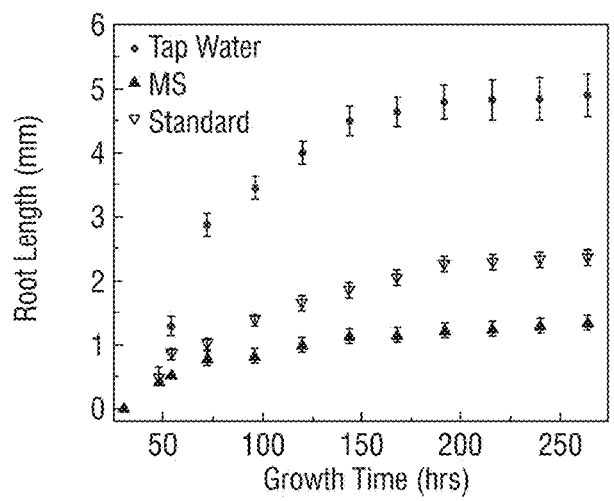
Figure 21B:
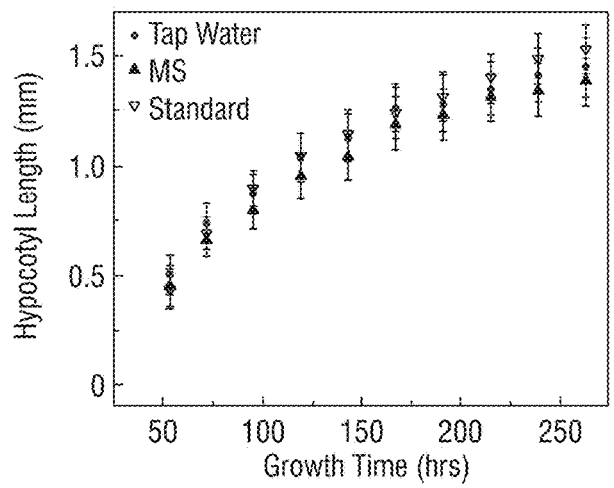
Figure 21C:
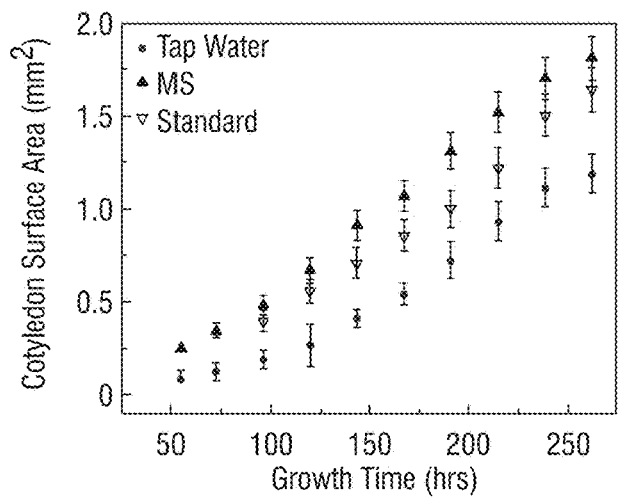

FIGS. 21A-C are graphs derived from time-spaced images illustrating quantification of differences in size from image processing of the images relative to different water/nutrient environments of FIGS. 20A-C.

Figure 22:
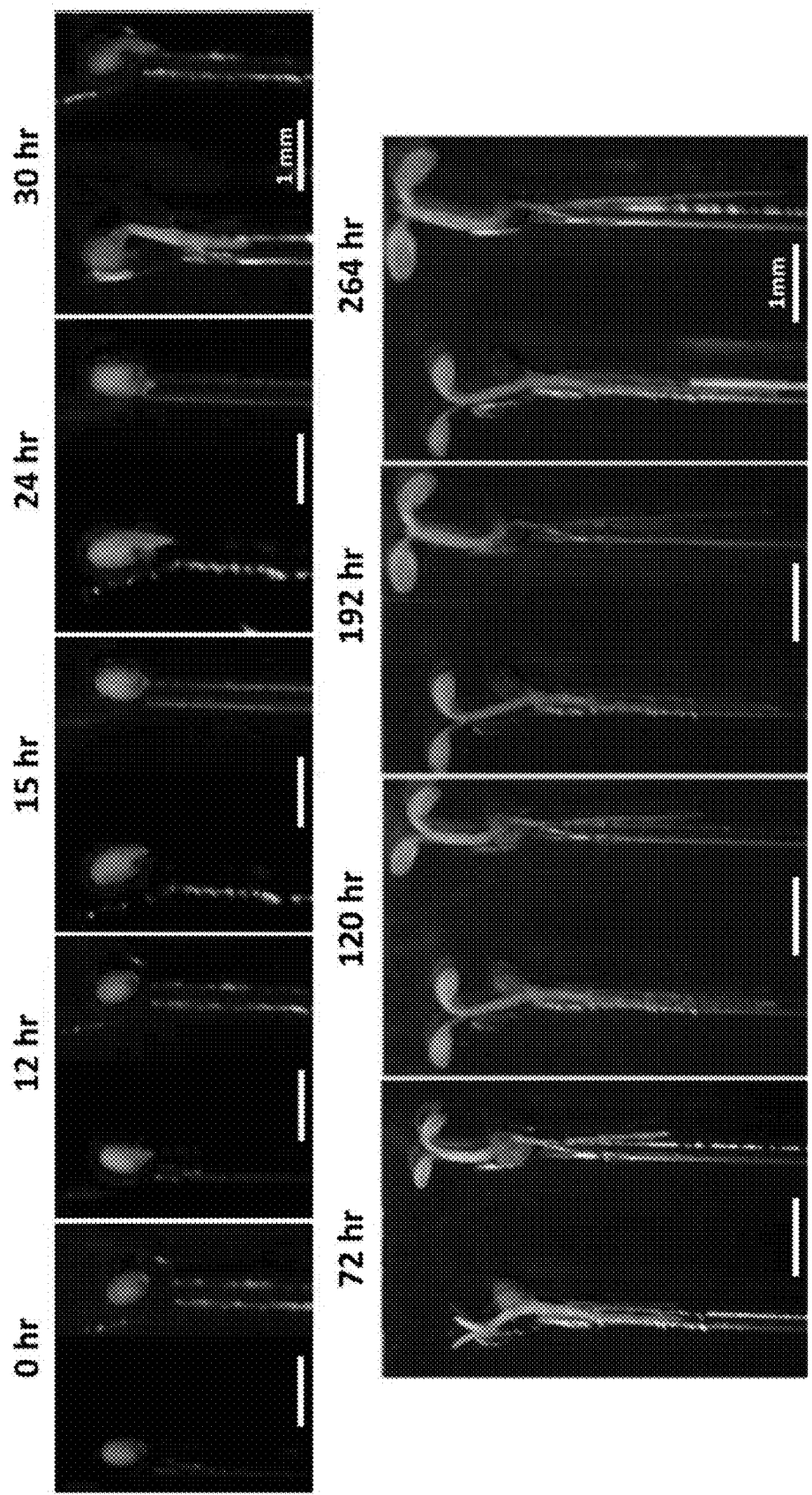

FIG. 22 is a series of side-by-side color images taken at indicated time intervals during growth of a two plants in their respective MSCs, the plants differing genotypically, allowing visual and digital image processing comparison of differences in phenotypic traits with time.

Figure 23A:
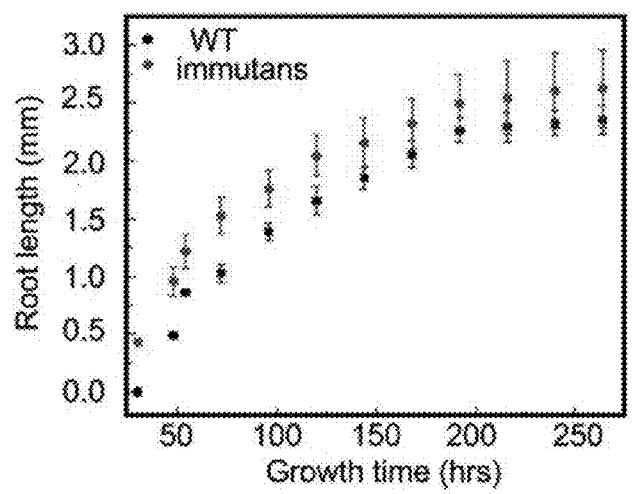
Figure 23B:
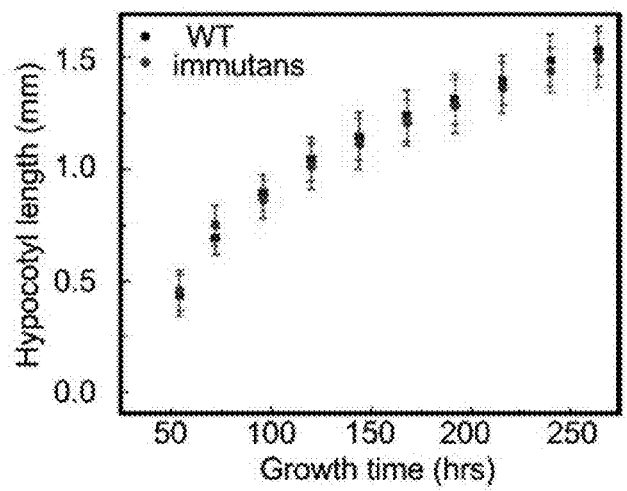
Figure 23C:
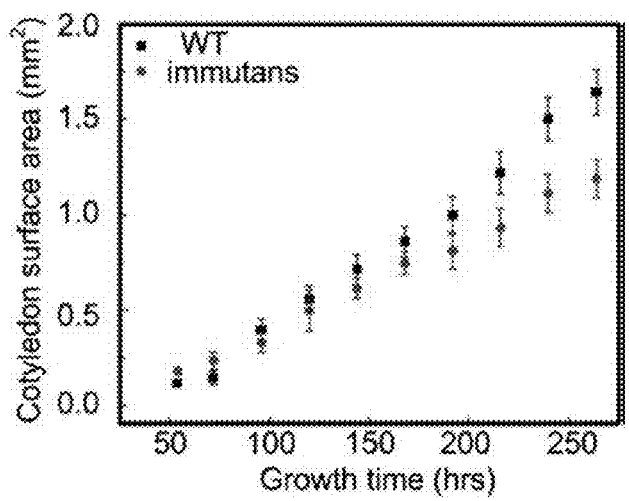
Figures 25A, 25B, 25C, 25D, 25E:
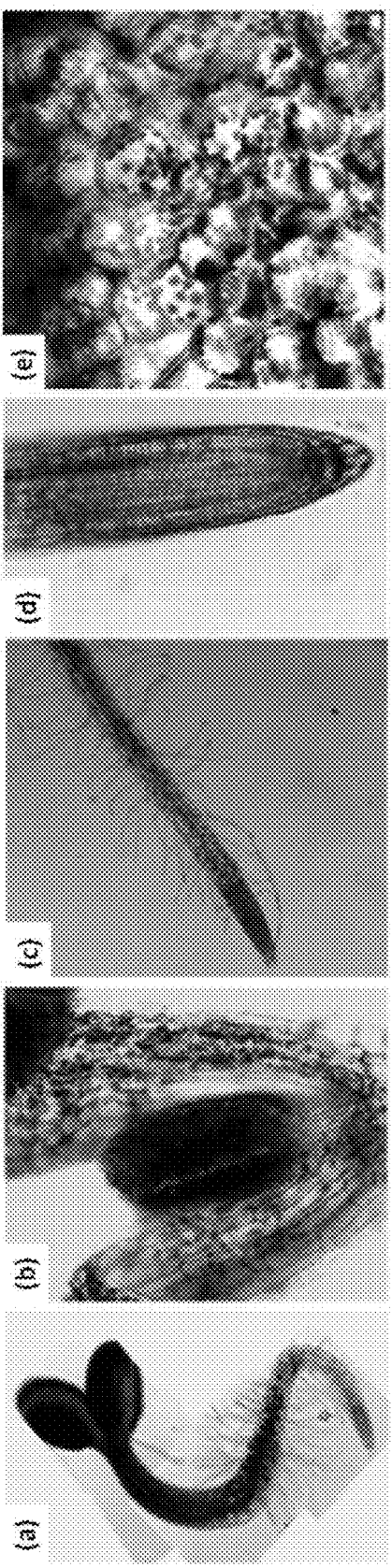

FIGS. 23A-C are graphs derived from time-spaced images illustrating quantification of differences in size from image processing of the images relative to different water/nutrient environments of FIGS. 22A-C.

FIGS. 24A-B are color images of plant growth in a MSC of the same plant at roughly the same time but differing in that FIG. 24A is an acquired image across the visible spectrum while FIG. 24B is an acquired image of fluorescence from the plant across a spectrally limited range correlated to the fluorescence.

FIGS. 24C-D are similar optical and fluorescence color images of the plant of FIGS. 24A-B, but at a time-separated time.

FIGS. 25A-E are confocal laser scanning microscopy color images of seedlings growing in an MSC at different magnifications.

Figure 26A:
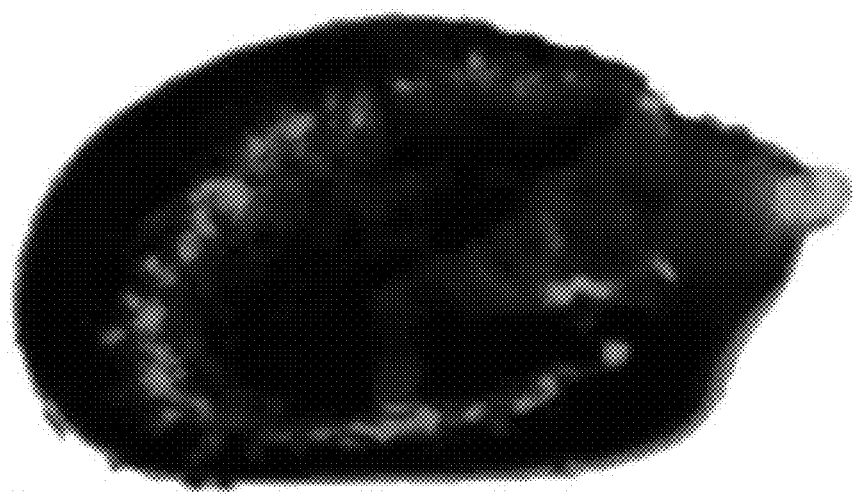
Figure 26B:
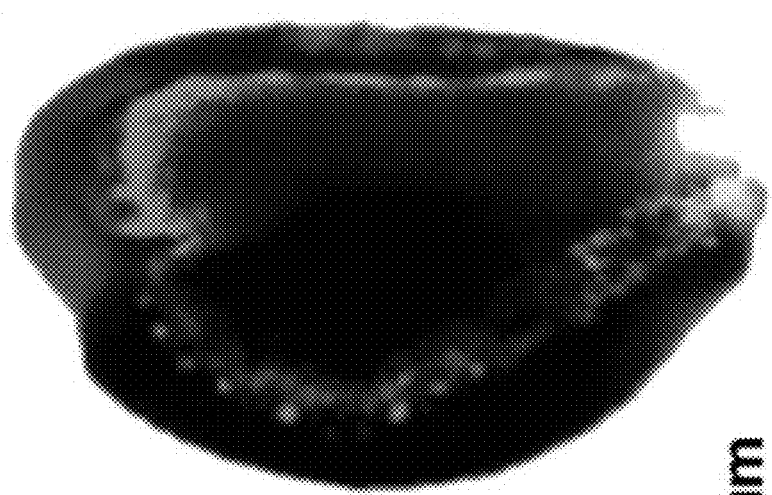
Figure 26C:

FIGS. 26A-C are microscopy color images of seed germination in a seed site of a MSC over time.

FIGS. 27A-D are microscopy color images of root development in a MSC over time.

Figure 28:
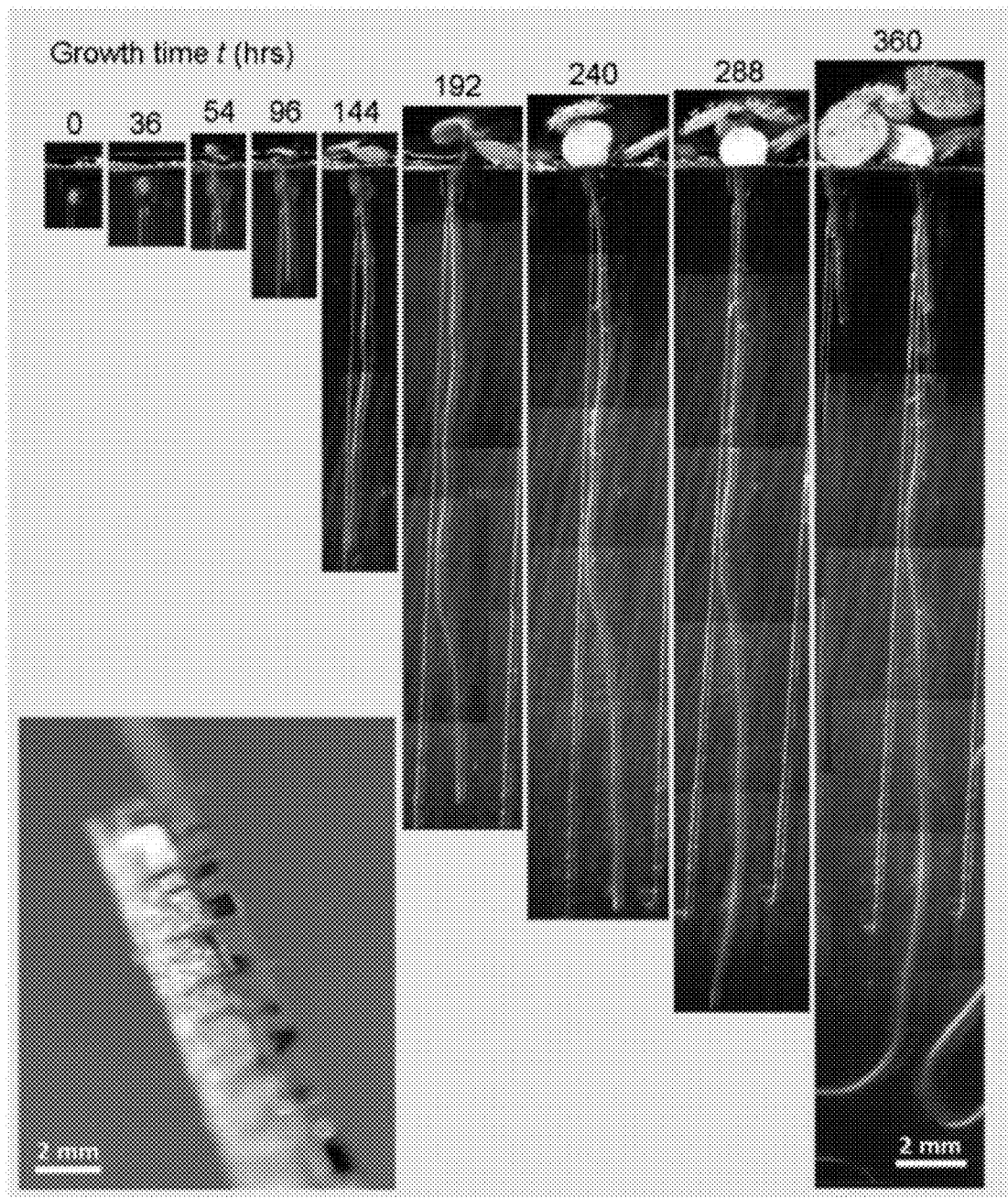

FIG. 28 is a series of seed germination, and root and shoot development over time in an open-top MSC. The insert (lower left side magnification) is a top edge view of an open top MSC.

Figure 29:
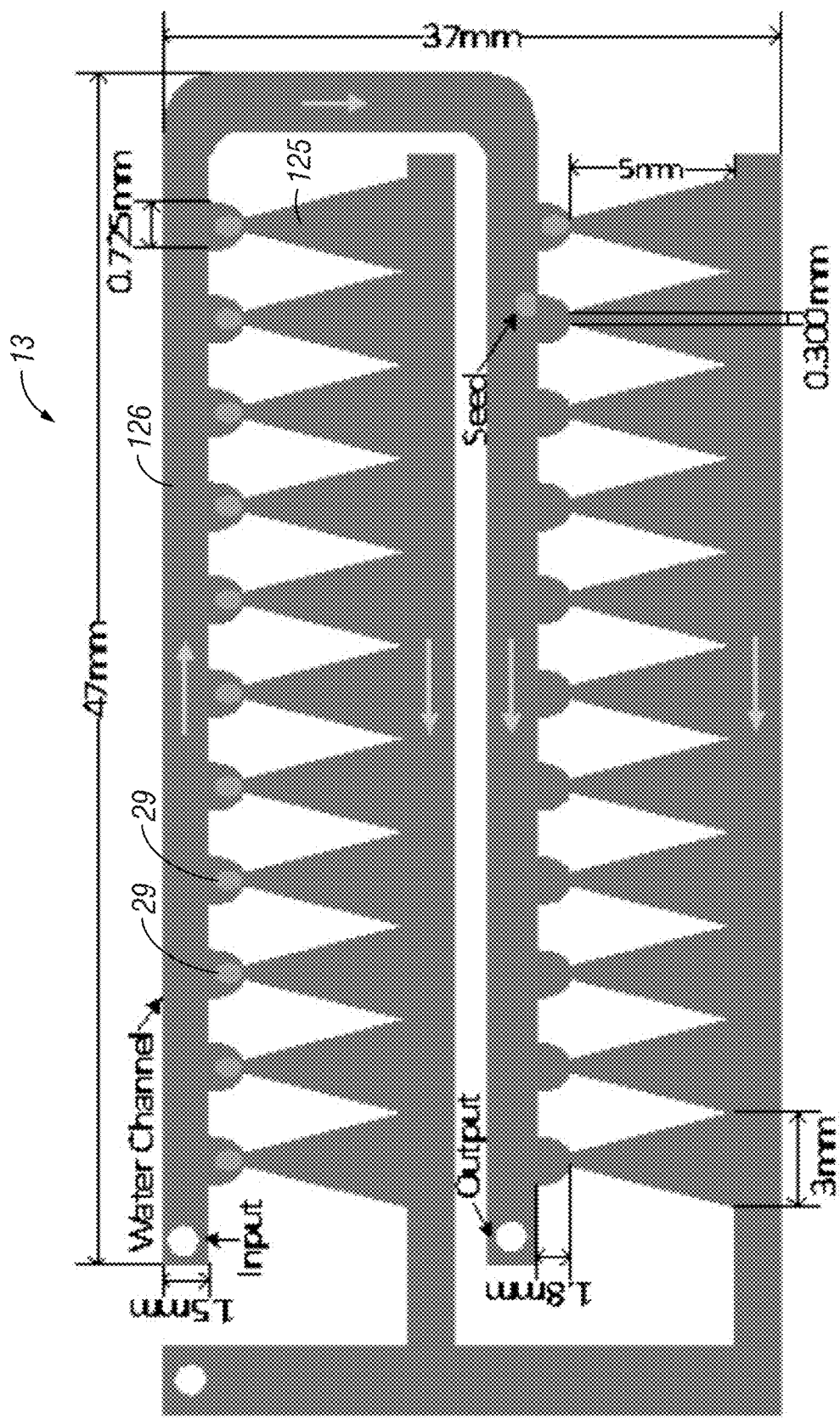

FIG. 29 is a diagram (not to scale) of an alternative double row MSC with seed sites, and closed shoot and root growth spaces.

Figure 30:
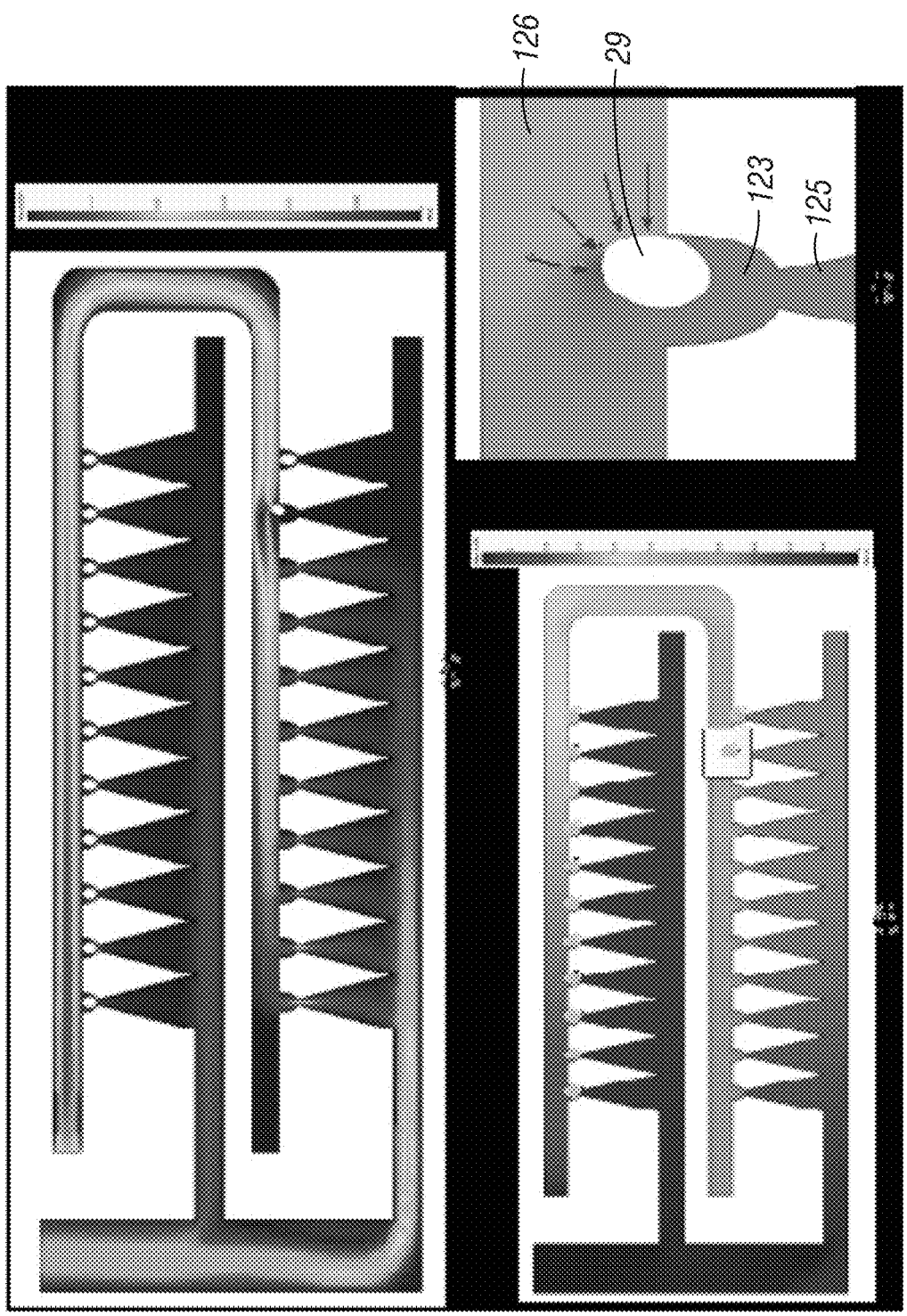

FIGS. 30A-C are color diagrams illustrating automatic seed trapping at the seed sites of the MSC of FIG. 29.

Figure 31:
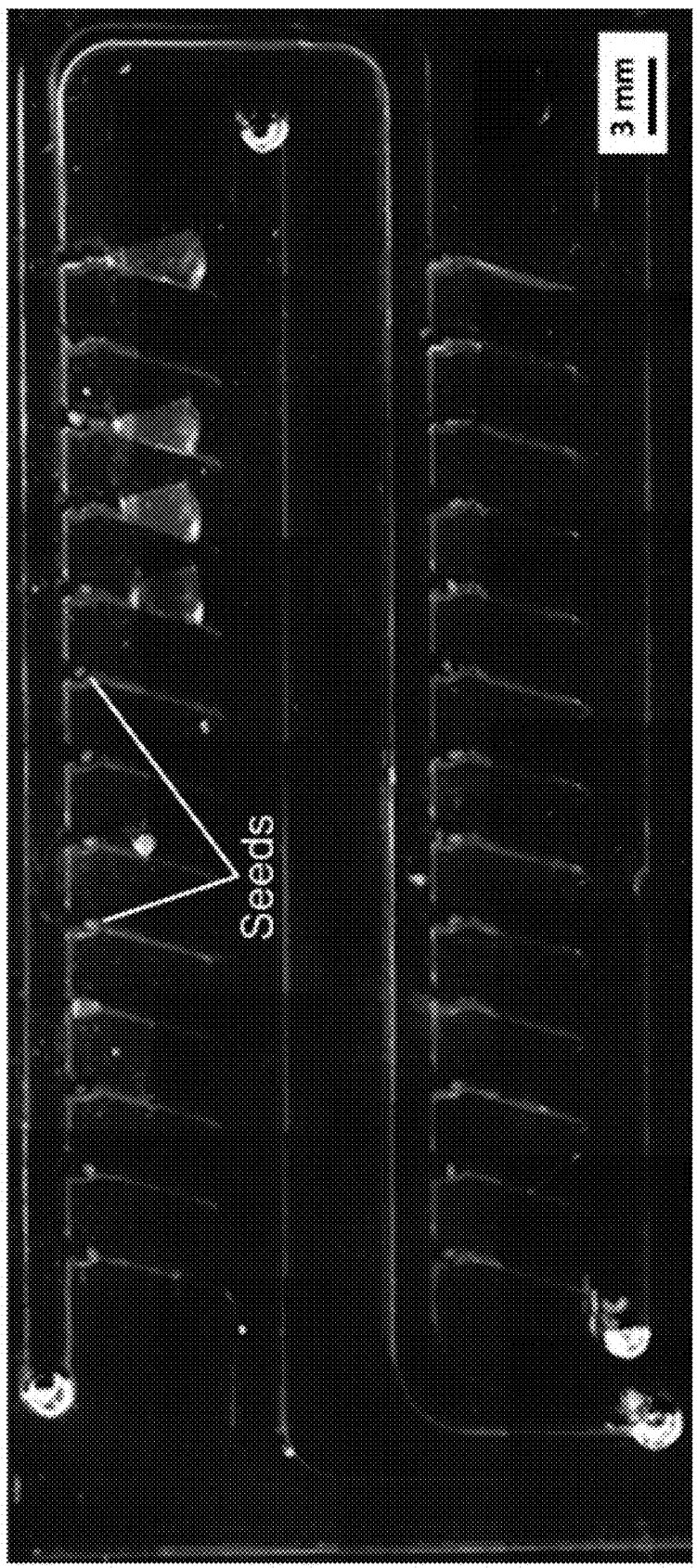

FIG. 31 is similar to FIG. 19B, and is a color image showing seed trapping in a MSC.

Figure 32A:
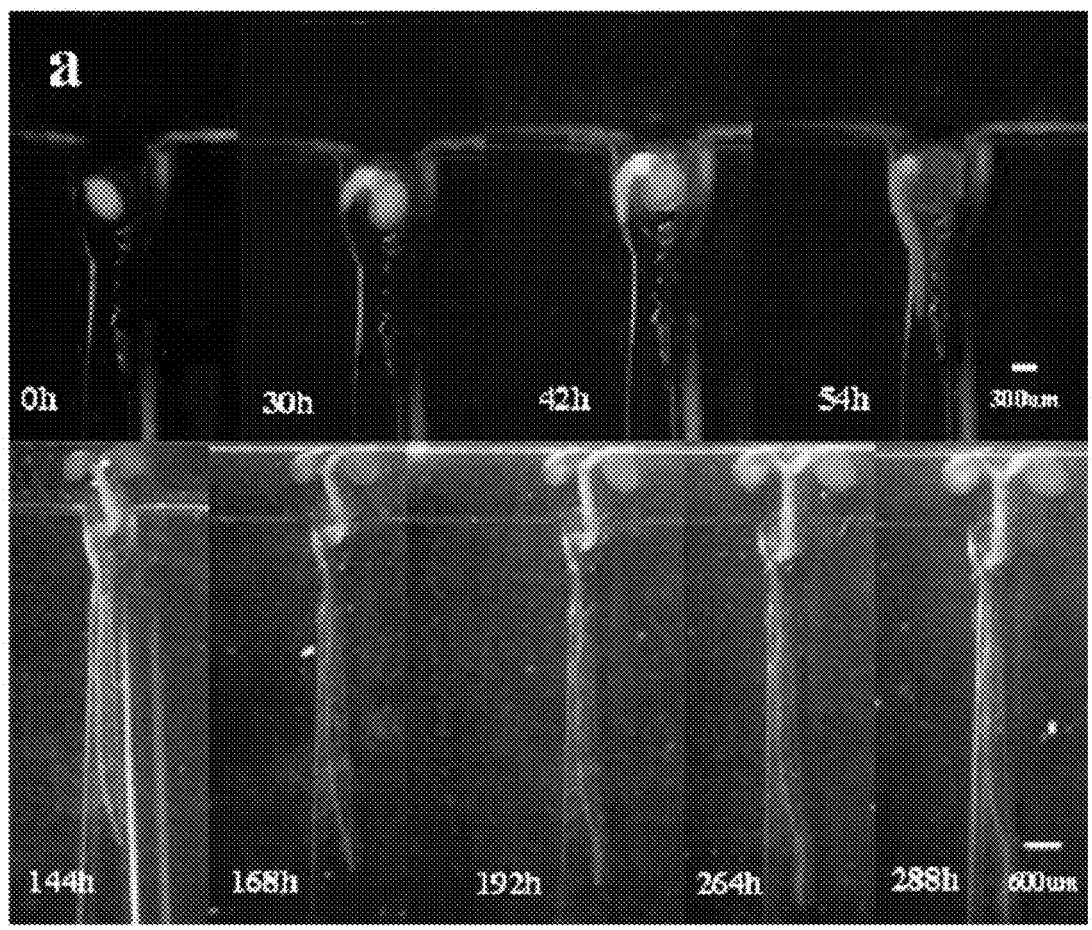

FIG. 32A is a sequence of color optical images of a plant in an MSC showing seed germination and seedling growth in tap water at separated times.

Figure 32B:
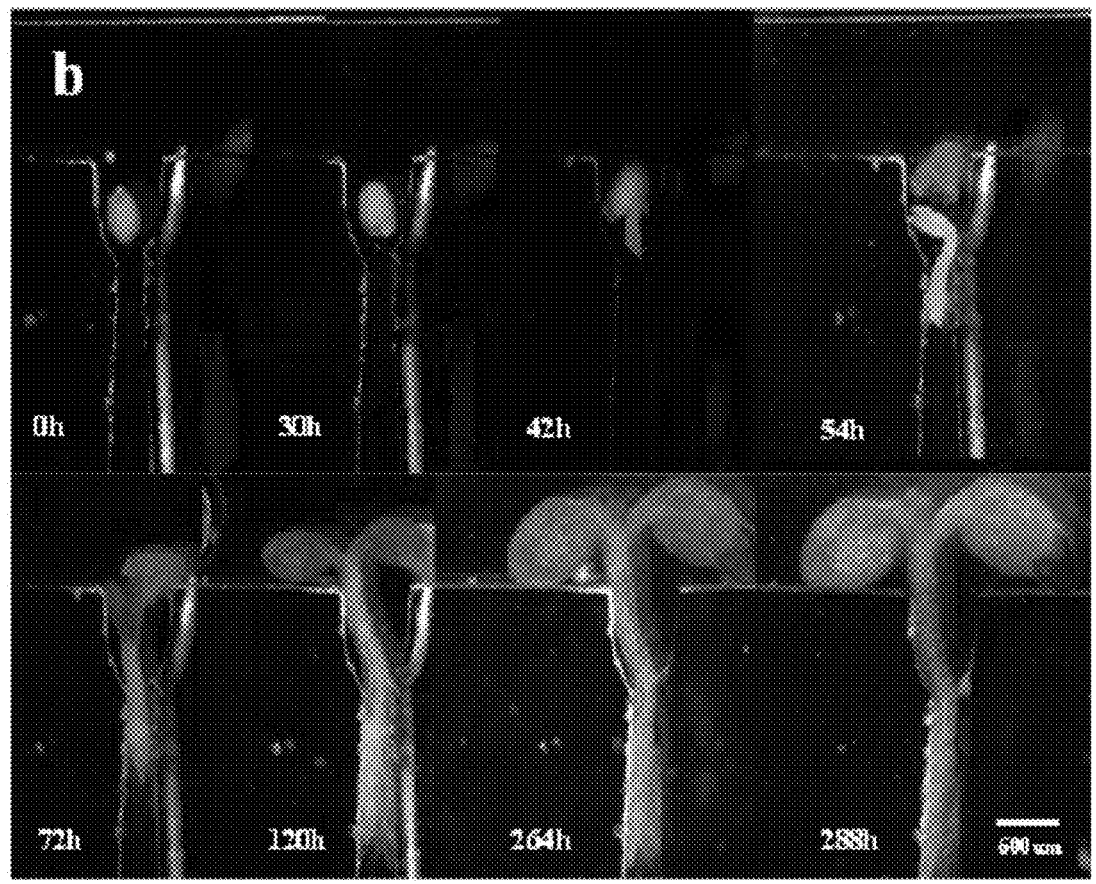

FIGS. 32B and C are color image sequences at the same separated times but for plants in different MSCs growing in different media.

Figure 32C:
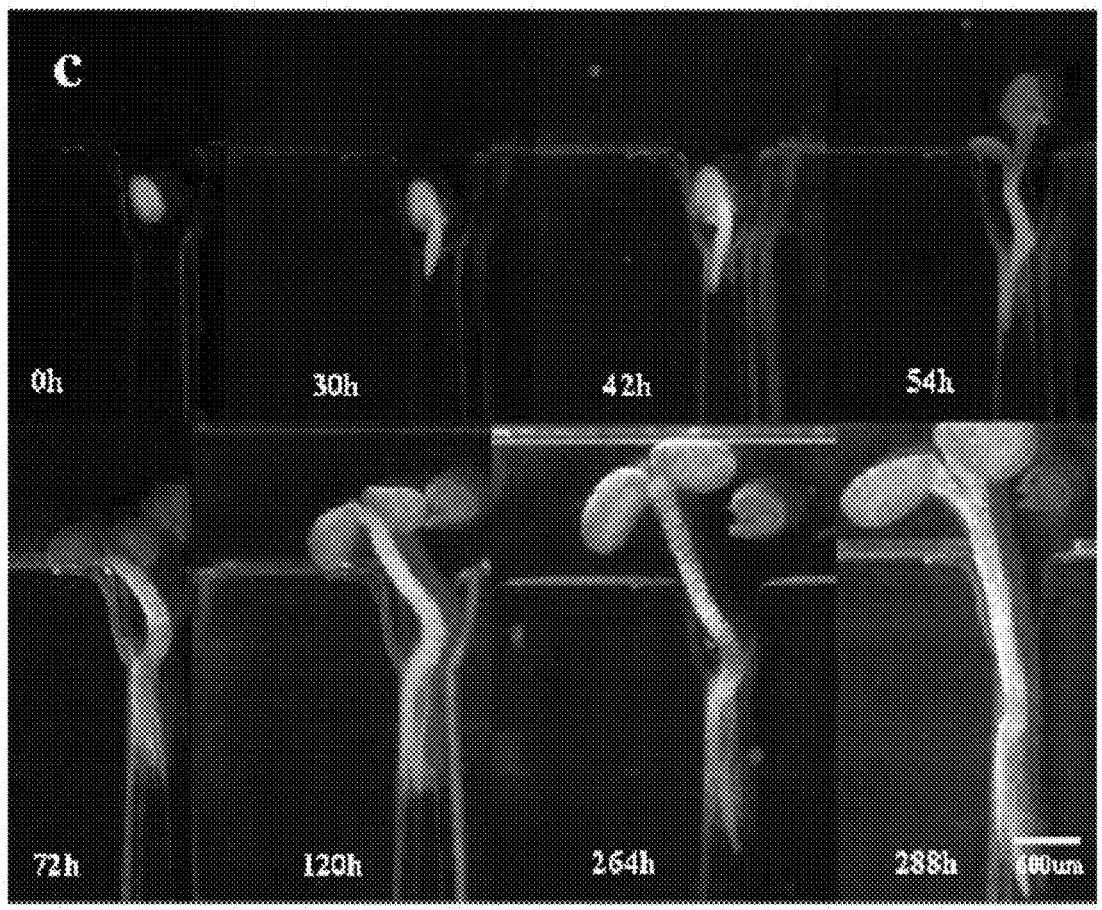
Figure 33A:
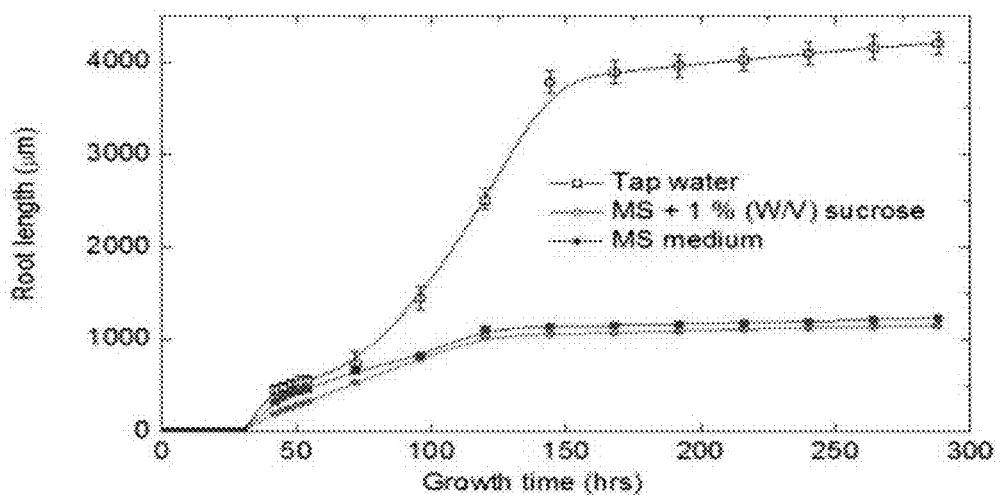
Figure 33B:
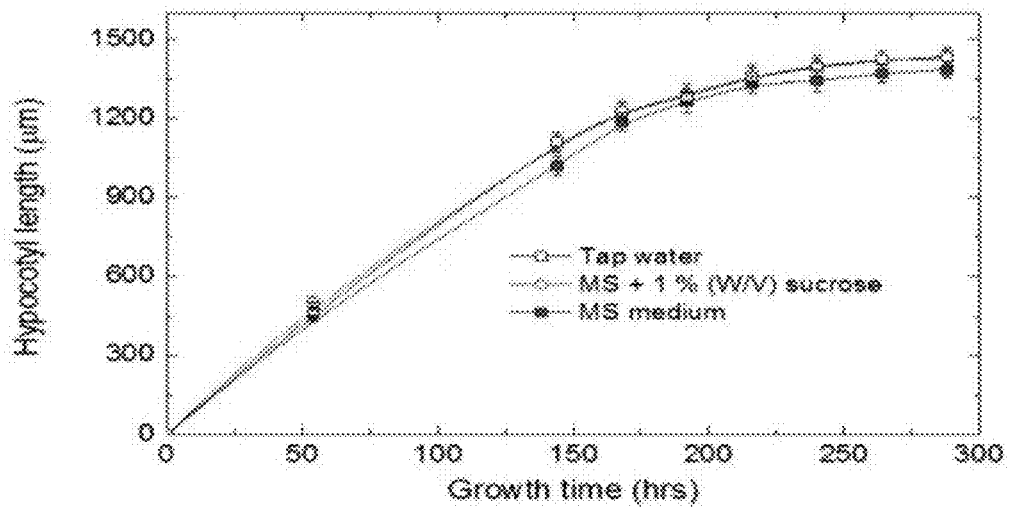
Figure 33C:
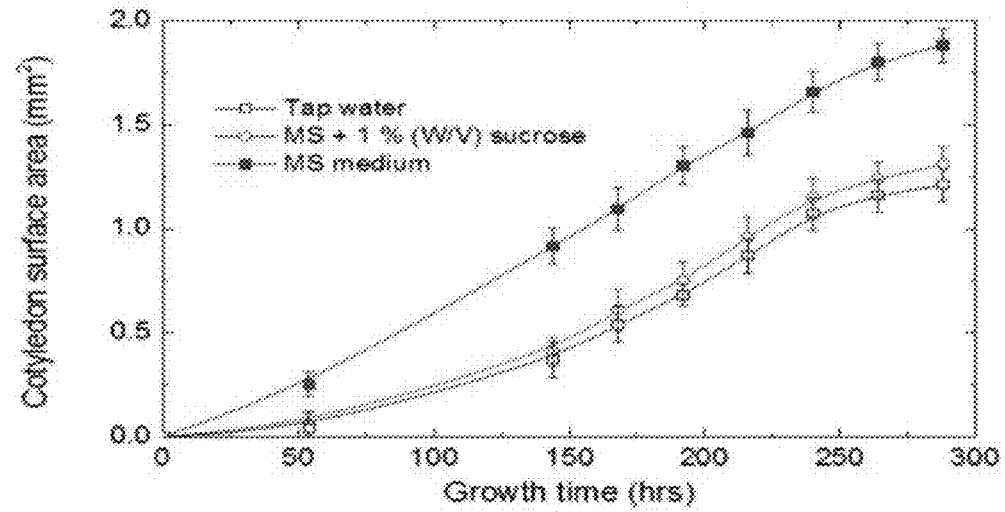

FIGS. 33A-C are graphs comparing phenotypic traits of the three plants of FIGS. 32A-C as quantified by digital image analysis of the images of FIGS. 32A-C.

IV. DETAILED DESCRIPTION OF EXEMPLARY EMBODIMENTS OF THE INVENTION

A. Overview

For a better understanding of the invention and its aspects, several examples of forms or embodiments the invention might take will be discussed in detail below.

It is to be understood that these are examples only, and neither inclusive nor exclusive of all the forms the invention can take.

The examples will be discussed primarily in the context of assaying plants. However, it is to be understood the invention could be applied to other things.

From time to time reference will be made to the drawings, which are incorporated by reference herein. Reference numbers will be used to indicate certain parts and locations in the drawings. The same reference numerals will indicate the same parts or locations unless otherwise indicated.

In one form, an embodiment of the invention is a high-throughput, large-scale plant phenotyping instrumentation whose purpose is to realize high throughput screening of plant-environment interactions for rapid discovery of such things as genotype-to-phenotype interactions at high spatial and temporal resolution. The core of the instrumentation of this embodiment is an integrated plant growth system comprising an array of miniature greenhouses (MGHs), vertical microfluidic seed chips (MSCs), and microfluidic control logic. The plant growth system can provide maximal environmental flexibility in large- and multi-scale study of plant-environment interactions. Each MGH can flexibly regulate relative humidity (RH), $CO_2$ level, and light intensity via controlled microfluidic capillary filling, controlled chemical reaction, and liquid crystal technologies, respectively. The vertical MSCs are designed to be sliding chip-like disposable components for use inside the MGHs. Each MSC can not only allow a number of plants to simultaneously grow for a desired period of time, but automatically trap individual seeds, change growth temperature, regulate different chemical concentration, and introduce biological species to the plants.

The vertical chip design for these MSCs allows for emulating normal gravitropic growth of plants, and for easy observation of phenotypes of multiple organs at the cellular as well as organismal level, including both root and shoot growth. Large-scale integration of an array of MGHs and MSCs is achieved by robust microfluidic control logic, resulting in setting up a large number of unique plant growth environments in multiple MGHs. A programmable imaging system is used to collect plant images.

However, instead of the microfluidic seed chips or MSCs, alternative seed holding components and alternative techniques of delivering liquid, gas, or solid phase materials to at or near the seeds/seedlings, or other items of interest being evaluated, can be used. For example, if seeds/plants or other items under investigation by the instrument are or will be larger than on the order of micro-scale, the instrument can be scaled up and might use seed (or other item) holding components bigger than a micro-chip-size and with fluid/gas/solid phase delivery paths bigger than microfluidic size.

Altered phenotypes have been central to the discovery of gene functions and molecular relationships among genes, thus illustrating the close relationship between the genotype and the phenotype of an organism. The recent completion of the genome sequencing projects, especially for model organisms such as the plant *Arabidopsis thaliana*, along with advances in high-throughput technologies (e.g., microarrays) have made it possible for a high-throughput "systems approach", and to acquire a great wealth of information about the genotype.

Most of the existing instrumentation and software have been built for genomics studies, with the key goal of identifying and analyzing RNA's, proteins, and metabolites. However, systematic analysis of genotype-to-phenotype relationship is still in its infancy, and the development of instrumentation for large- and multi-scale phenotypic profiling lags behind the rapid advances in instrumentation for genomic studies. Particularly, due to a lack of high-throughput plant phenotyping tools, systematic characterization of plant phenotypes remains a difficult challenge, as even model plants with smaller genomes such as *Arabidopsis thaliana* contain tens of thousands of genes. Moreover, plant development and growth is sensitive to environmental conditions (e.g., temperature, light, CO2, salt, humidity, drought, pathogen, etc.), as the underlying network of genes responds to these stimuli. Because of this inherent complexity, analyzing plant phenotypes on a large and multi-scale level with sufficient throughput, resolution and precision has been difficult and expensive.

The phenotyping instrumentation disclosed here can provide a generation of instruments allowing automated, accurate control of various plant growth environments and quantification of phenotypic traits related to plant performance. The phenotyping instrumentation is capable of tuning key environmental parameters such as relative humidity (RH), CO2 level, light intensity, temperature, and chemical/hormone concentrations to facilitate large- and multi-scale study of plant-environment and plant-pathogen interactions.

The phenotyping instrumentation allows growing multiple plants hydroponically and takes pictures for growing plants over a period of time. The phenotyping instrumentation is useful to a wide range of researchers in plant biology (functional genomics, phenomics, etc.).

Figure 1A:
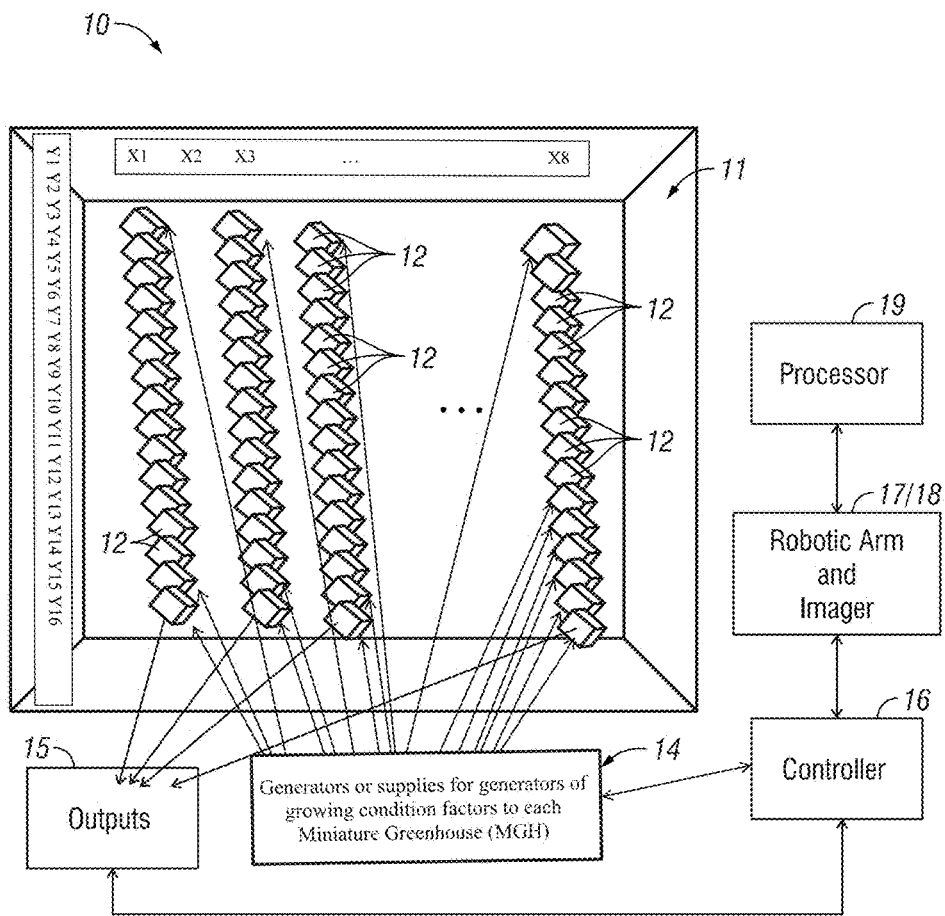
FIG. 1A is a diagrammatic illustration of an overall system according to one exemplary embodiment of the present invention.

In one example of implementation of aspects of the invention and used to evaluate *Arabidopsis thaliana*, what will be called a platform (e.g. a supporting surface or area such as glass or other substrate-type material) having a hundred or more (e.g. 128 but the designer can configure more or less) what will be called miniature greenhouses (MGHs) are spatially separated in a pre-designed array on the platform. The diagram of attached FIG. 1A provides a generalized diagrammatic representation of the same.

A system 10 according to this embodiment includes a platform 11 which would typically be placed horizontally on a table or other support inside a building. The diagram of FIG. 1A illustrates conceptually how platform 11 could itself support an n row by m column array of MGHs 12. Each MGH 12 would be individually addressable by operable connection to (or operation with) one or more inputs 14 and one or more outputs 15.

Examples of inputs for seeds/plants, which will be discussed in detail below, include such things as water, CO2, and light. A controller 16 can instruct appropriate components 14 to generate or regulate such things independently, if desired, at each MGH 12. An additional example of a regulated input could be temperature control, such as with a controllable heater.

Examples of outputs 15 could be sensor readings at or associated with the MGHs. In this example, appropriate sensors could feedback to controller 16 RH, CO2, light level, and temperature readings. Controller 16 could compare them to preset target values and automatically regulate those factors at each MGH.

As will also be discussed below, one way to supply growing factors that require fluid (gas or liquid phase) in relatively small quantities is through microfluidic channels and control logic. Here examples are water for humidity and $CO_2$ at the plants. Also, certain microfluidic control (valves and pumps) are powered with fluid pressure (positive or negative) that can be delivered through microfluidics. Other growing factors can be generated or regulated electrically or electronically. Here examples are electrically actuated heating and light transmissivity.

Programmable control of movement and image acquisition coordinated with controller 16 in this example is accomplished with a robotic arm 17 supporting a digital camera 18. Specifically, robot arm 17 has sufficient freedom of movement and precision to move camera 18 to any MGH 12 and effectively obtain desired images of seeds/plants 29 inside a MGH 12. Needed portions of MGH 12 are effectively transparent enough to allow good images through its enclosing walls. In this embodiment, camera 18 has a microscopic lens to allow a range of magnifications in acquired images.

FIG. 1A also includes a processor 19 (e.g. computer) operably connected to controller 16, robotic arm 17, and camera 18 to store acquired images in correlation to the particular MGH 12 involved as well as other data such as time, viewing angle, etc. In this manner, the designer can program a regimen of images acquired of different MGHs 12 over time. Processor 19 can then utilize digital image analysis software to quantify such things as length and width of a root or shoot, or color of the same. This allows comparison of images of the same plant over time, or comparison to other plants in the same or different MGH 12. Automatic quantification of aspects of the images allows the processor to make massive number of comparisons relatively quickly. This can facilitate efficient evaluation of plant development relative to different regulated environments over statistically meaningful populations.

As can be appreciated in FIG. 1A, a single platform 11 could utilize microfluidic and microelectronic technologies to supply fluid and electrical signals to and from each MGH 12. The control of microfluidics and electricity would use well-known techniques to distinguish between the x, by y, array. And, of course, as many additional platforms 11, each with an array of MGHs 12 could be coordinated in the same experiment or concurrently run different experiments, each with a system 10.

Figure 1B:
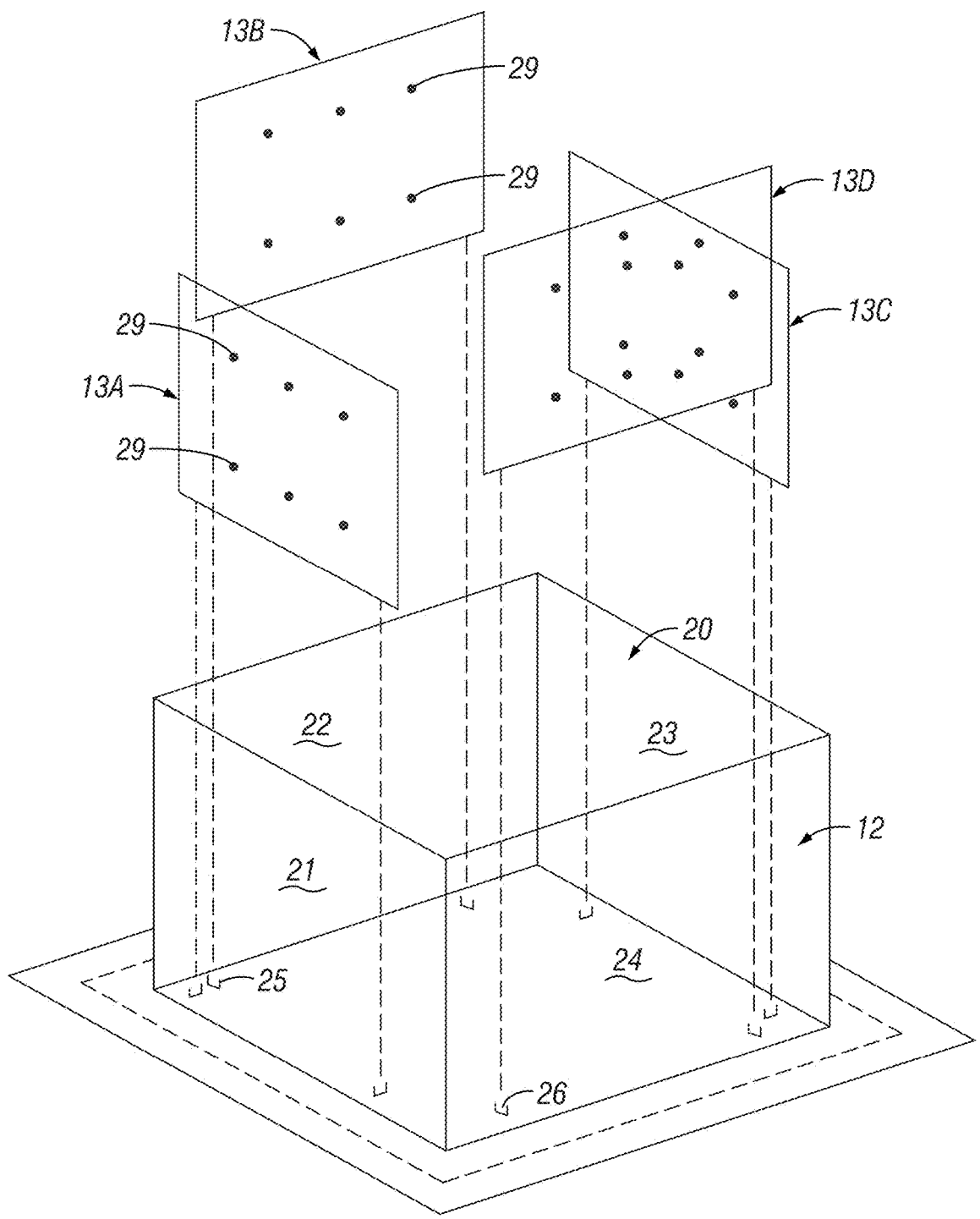
FIG. 1B is an enlarged, isolated and exploded illustration of a single miniature greenhouse (MGH) of the system of FIG. 1, showing how one or more micro seed chips (MSC) could be installed in the MGH.

FIG. 1B is an enlarged perspective of a MGH 12. It essentially is a box defining an interior volume of space 20 by four vertical transparent walls 21, 22, 23, and 24. In this embodiment, the top and bottom of the transparent box would be closed off by a floor comprising one or more of the generators or regulators of growing factors.

By creating miniature greenhouses 12 (as opposed to conventional ones or even controlled growing chambers like the LemnaTec systems), and coordinating them in a confined space array, the space needed for the system 10 is reduced and efficiencies in delivery of materials to each MGH are achieved. In a counter-intuitive manner, a miniaturization can still concurrently process a large number of plants (which is meaningful statistically), with more precision and accuracy because control of the variables can be more effectively utilized and administered. Programmable controller 16 and processor 19 components can automate delivery of needed materials to the MGHs 12 and acquisition of data from them in an efficient manner.

It is to be understood, however, that the number of MGHs 12 can vary according to need or desire. Likewise can their size.

Figure 2:
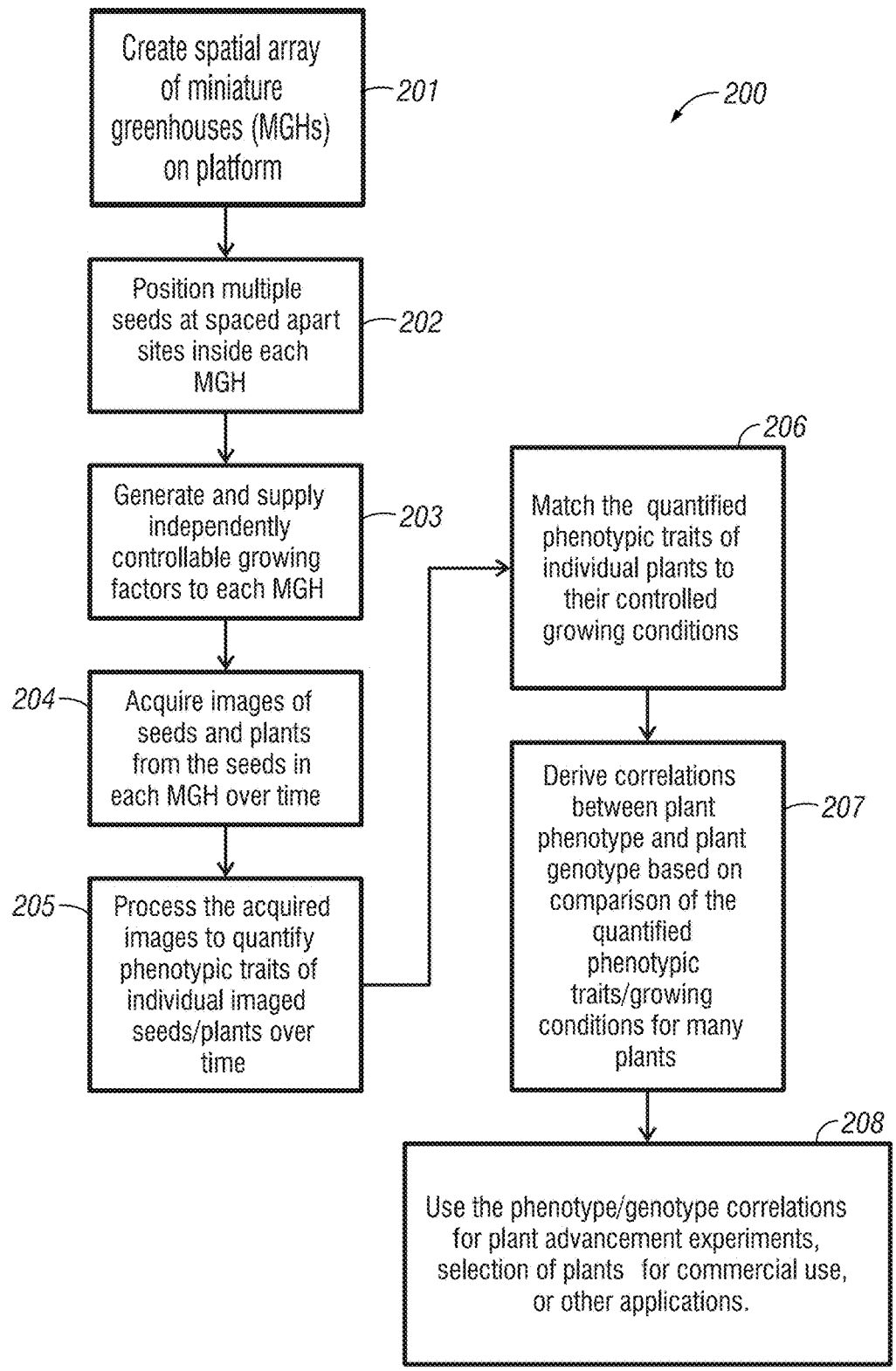
FIG. 2 is a flow chart diagram of a methodology according to an exemplary embodiment of the present invention.

FIG. 2 gives a high-level flow chart of one example of a methodology 200 according to one aspect of the invention. If an array of miniaturized greenhouses can be administered with growing factor substances in an effective, efficient way, and data acquired in a similar fashion, a large number of plants can be evaluated for a number of different growing condition/environment variables, to cost-effectively and quickly obtain statistically-meaningful data for identifying plant/environment interactions that are expressed in phenotypic traits. This allows such things as providing important insight for plant researchers as well as potentially identifying plant genotypes that will perform better in certain environmental conditions (e.g. drought versus wetter conditions, hotter versus cooler climates, etc.). This can be valuable to commercial seed companies and crop producers. Other applications are, of course, possible.

The MGHs are analogous to an array of integrated circuits placed on a circuit board or substrate. Each self-contained circuit can independently carry out functions. Each is individually addressable via inputs and outputs. Here an array of MGHs will be laid out on a platform (FIG. 2, step 201). Each MGH is individually addressable by inputs and outputs (here generated or regulated growing factors) and sensors to feedback information to a controller regarding the state of those factors so that each MGH can be its own customizable "living environment".

Each MGH can contain one or more seeds/plants (FIG. 2, step 202). One example of a carrier or holder for them is the Micro Seed Chip (MSC) 13 shown in FIG. 1B removed from its MGH 12. One or more MSCs 13 can be placed in an MGH 12. In this example, four MSCs 13A-D are removably mountable in a pair of u-shaped chip holders 25. Each holder 25 has a slot 26 complementary with the thickness of a MSC 13 and supports it in a vertical position inside MGH 12 along each transparent wall 21-24 of MGH 12. Each MGH 12 is supplied its pre-programmed regimen of growing conditions (FIG. 2, step 203). The manner in which an MSC 13 is installed in a MGH 12 can vary, as will be appreciated by those skilled in the art. Each MSC 13 is made of transparent or at least substantially transparent or light transmissive material. This allows multiple seeds/plant per MGH and allows an imager to move to each MGH wall 21-24 and obtain images of seeds or plants growing in any MSC 13 (FIG. 2, step 204). Imaging of seeds/plants is possible through the transparency of materials of the MGH and MSC.

Image processing of the imaging of germination and growth from seeds to seedlings in an MGH over time produces data about phenotypic traits and how they proceed over time for the given environmental conditions provided to the MGH (FIG. 2, steps 205 and 206). From that data predictions about what genotypes of the plant will perform best for given environments can be made, as one example (FIG. 2, step 207). By being able to vary different growing factors (e.g. water, light, nutrients, etc.) for statistically significant numbers of seeds/plants for a given experiment on a relatively small platform, such predictions can be accomplished with precision and efficiency. Those predictions can be used in a number of ways (FIG. 2, step 208). One example is by seed companies to determine which genetic make-up for a seed will be most commercially valuable to reproduce and sell for given conditions. For example, system 10 could help discover that a certain genetic make-up for a seed species develops better in drought or low water conditions than others, and can reproduce commercial quantities for geographic areas susceptible to drought or low water conditions.

MGHs can be of a variety of sizes and form factors. For some applications, they can be on the order of several inches in height, width, and depth and made of transparent material. Many (hundreds or perhaps more) can be spaced apart on a surface or platform 11 that would occupy less than a room-sized area. For smaller seeds and plant like *Arabidopsis thaliana* the area needed for 128 MGHs might be as small as a couple of feet by a couple of feet. Delivery and generator mechanisms to get different environmental growing factors to each MGH (e.g. water, light, air, nutrients) can be organized and installed on the platform to allow efficient but independent control to each MGH. Each MGH can house from one to quite a few plants. Therefore, experiments can concurrently service hundreds and thousands of plants with each subset in each MGH having its own pre-designed living conditions. By such predesign, a processor can automatically take images acquired over time from each MGH and quantify how plants in each MGH responded to the environmental conditions generated in it. By gathering this information for the many different MGHs, correlations between phenotypic information and genetics can be made.

The experiment can be time-limited. For example, seed germination and seedling growth for no more than a few weeks can be sufficient to acquire valuable phenotypic information for making the correlations. This can allow the MGHs (and MSCs, if used) to be smaller because they do not need to accommodate full, mature size plants. Once the experiment is done, the seedlings can be removed, the delivery channels and mechanisms cleaned out, and a next experiment can proceed with the same efficient and effective use of space, time, and resources. By having integrated and coordinated control of the array of MGHs in the limited space of the platform, high accuracy, reduced costs in materials, energy, and labor result from this highly automated system. And it can process large numbers of plants with high throughput.

If micro seed chips (MSCs) are used, they are relatively inexpensive to produce and can be disposable, further lessening the time and resources of change-over between experiments. For example, they can be made of plastics or glass/plastic laminations and produced relatively economically in mass quantities.

B. System

Below is a description of an overall system according to one aspect of the invention.

This is a high-throughput, large-scale plant phenotyping instrumentation whose purpose is to realize high-throughput screening of plant-environment interactions for rapid discovery of genotype-to-phenotype interactions at high spatial and temporal resolution. The invention will benefit at least the following biological research community: plant biology (functional genomics, phenomics, etc.). The core of the instrumentation is an integrated plant growth system including an array of miniature greenhouses (MGHs), vertical microfluidic seed chips (MSCs), and microfluidic control logic. In the broadest context of the invention, the seed chips are optional. Other types of seed holders or sites could be used in each MGH.

The plant growth system can provide maximal environmental flexibility in large- and multi-scale study of plant-environment interactions. Each MGH can flexibly regulate relative humidity (RH), CO2 level, and light intensity via controlled microfluidic capillary filling, controlled chemical reaction, and liquid crystal technologies, respectively. If used, the vertical MSCs are designed to be sliding chip-like disposable components for use inside the MGHs. Each MSC can not only allow a number of plants to simultaneously grow for a desired period of time, but automatically trap individual seeds, change growth temperature, regulate different chemical concentration, and introduce biological species to the plants. The vertical chip design for the MSCs will allow for emulating normal gravitropic growth of plants, and for easy observation of phenotypes of multiple organs at the cellular as well as organismal level, including both root and shoot growth. Large-scale integration of an array of MGHs and MSCs will be achieved by robust microfluidic control logic, resulting in setting up a large number of unique plant growth environments in multiple MGHs. A programmable imaging system will be designed to collect plant images. To quantify morphological traits precisely and determine phenotypic differences, an automated algorithm will be developed to extract and analyze images acquired during plant development.

Characterization of the complete plant phenome poses a difficult challenge due to the large number of genes in the genome(s), and changeable environmental conditions that influence plant phenotypes. Because of this complexity, analyzing plant phenotype(s) on a large- and multi-scale level with sufficient throughput and resolution has been difficult and expensive. The invention can be implemented in large-scale, high-throughput plant phenotyping instrumentation, and therefore will constitute a significant leap in throughput and information content over existing phenotype assays. The instrumentation can also be flexibly scaled up and down to phenotype different plant species growing to different stages. Thus, this instrumentation will contribute to systematic analysis of plant phenotypes with a wide range of applications in gene identification, functional genomics, and genotype-to-phenotype correlations.

The instrumentation addresses grand challenging large-scale problems in the field of phenomics, will build resources to benefit plant biology researchers, and will create a paradigm shift in the plant phenomics area by placing powerful data analysis capability in the hands of researchers, and thereby accelerate the pace of discoveries.

B1. Overview

Figure 3:
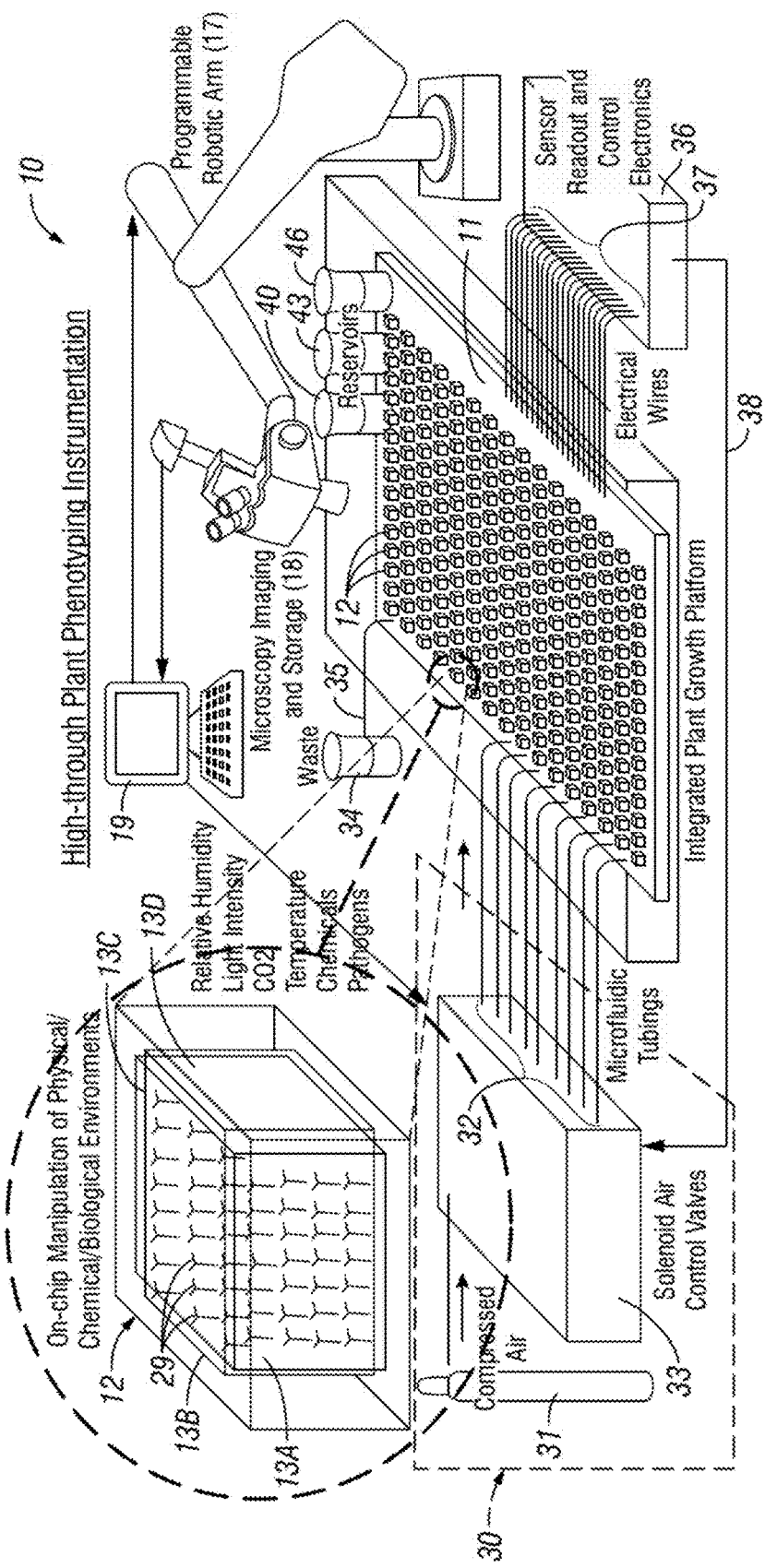
FIG. 3 is a diagrammatic illustration of an overall system according to one exemplary embodiment of the present invention.

With reference to FIG. 3, the following description provides a high level discussion of one embodiment of a whole system. FIG. 3 is a schematic for such a high-throughput plant phenotyping.

The system 10 uses vertical microfluidic seed chips (MSCs) 13 as a technique of holding seeds inside each miniature greenhouse (MGH) 12. However, it is to be understood that this is but one example and that alternative techniques are possible. For example, an alternative could be similar to a microtiter multi-well plate or something analogous. Seeds could be loaded into such an alternative holding device and include either on-device or off-device components or generators to supply one or more of a variety of plant growth environmental factors to at or near each of the seeds. The overall system does not necessarily have to use the MSCs.

System 10 can also use microfluidics as a technique to deliver various things to the seeds (e.g. fluids, gases, or other relevant things) inside each miniature greenhouse (MGH). However, it is to be understood that this is but one example and that alternative techniques are possible. For example, if the overall system is scaled up to sizes where conduits, channels, seed holders or receivers, etc. are bigger than those discussed with regard to MSCs, such may not be considered microfluidic or micro-size (i.e. where at least one dimension of the channel or feature is of the order of micrometers). An alternative could be similar channels or features but of larger scale, or channels or features that function similarly but on larger scale and different mechanisms for delivering gas, liquid, or solid phase materials through them or to them. The overall system does not necessarily have to use microfluidics.

A use of system 10 can be for phenotyping of plants grown, for at least an initial period, from seeds. However, it is to be understood that this is but one example and that alternative things can be investigated with the system. For example, insects could be held in place and supplied life-sustaining and growth promoting factors, and then imaged over time for the analogous purpose of correlating phenomic traits with genomic make-up or for other purposes. Or the system could be used for just tracking development (as it could for plants). Small animals are another possible alternative. Others include biological cells. The overall system is not limited to plants/seeds. As mentioned, system 10 can be scaled up for larger items of interest, and scaled down for smaller items of interest. This includes the potential of using microscopy for imaging of small items or portions thereof. For example, microscopic imaging could be used to image on the order of cellular level of items of interest.

Altered phenotypes have been central to the discovery of gene functions and molecular relationships among genes, thus illustrating the close relationship between the genotype and the phenotype of an organism [see, e.g., references B1, B2 of the bibliography below for Section B]. The recent completion of genome sequencing projects, especially for model organisms such as the plant *Arabidopsis thaliana*, along with advances in high-throughput technologies (e.g., microarrays), have made it possible for a high-throughput "systems approach", and to acquire a great wealth of information about the genotype [B3-9]. Furthermore, most of the existing instrumentation and software have been built with the key goal of identifying and analyzing RNA's, proteins, and metabolites [B10-14]. However, systematic analysis of genotype-to-phenotype relationship is still in its infancy, and the development of instrumentation for large- and multi-scale phenotypic profiling lags behind the rapid advances in instrumentation for genomic studies. Particularly, due to a lack of high-throughput plant phenotyping tools, systematic characterization of plant phenotypes remains a difficult challenge, as even model plants with smaller genomes such as *Arabidopsis thaliana* contain tens of thousands of genes.

Moreover, plant development and growth is sensitive to environmental conditions (e.g., temperature, light, CO2, salt, humidity, drought, pathogen, etc.) [B15-23], as the underlying network of genes responds to these stimuli. Because of this inherent complexity, analyzing plant phenotypes on a large and multi-scale level with sufficient throughput, resolution and precision has been difficult and expensive.

In this example, system 10 comprises a high-throughput, large-scale plant phenotyping instrumentation (FIG. 3). The core of this example of the instrumentation includes a miniature integrated plant growth system including multiple miniature greenhouses (MGHs) 12, seed holders, in this example vertical microfluidic seed chips (MSCs) 13, and microfluidic control logic (FIGS. 4A-E). The system 10 is capable of tuning key environmental parameters such as relative humidity (RH), CO2 level, light intensity, temperature, and chemical/hormone concentrations to facilitate large- and multi-scale study of plant-environment and plant-pathogen interactions. The vertical MSCs 13 (see also FIGS. 1B and 9A, and 10K) can be designed with the goal of growing multiple plants inside the MGHs (or alternatives), and the microfluidic logic control approach will be used to realize large-scale integration of an array of MGHs and MSCs (or alternatives) that will form phenotyping instrumentation. The instrumentation can be used to facilitate at least the following areas and can advance the emerging field of plant phenomics:

(a) Design, fabrication, and system integration of MGHs, MSCs (or alternatives), and microfluidic (or alternatives) control logic to form a high-throughput plant phenotyping system, for knowledge discovery in plant phenomics area.

(b) Systematic analysis of plant phenotypes with applications in gene identification, functional genomics, and genotype-to-phenotype correlations.

(c) Large-scale, high-throughput assays for screening of plant mutants phenotypes performed at high resolution while varying growth environments. For example, an automated imaging system in conjunction with, as one example, a robotic arm (or alternatives) can be used to take digital images of plant growth and development at specific intervals on vertical MSCs (or alternatives), and for data collection.

(d) Tracking developmental characteristics of multiple plant organs (e.g., cell, seed, root, shoot), and using the resulting estimates to quantify morphological traits more precisely and determine phenotypic differences, as well as understanding individual vs. combinatorial effects of varying environments on phenotypes.

B2. Description of the High-Throughput Plant Phenotyping Platform

The exemplary embodiment bioinstrumentation for high-throughput, high-resolution phenotyping of plants while varying multiple growth environmental conditions (of FIGS. 3 and 4A-E) will be further discussed below.

Integrated Miniature Plant Growth Platform:

As the core of this plant phenotyping instrumentation, the integrated plant growth platform 11 (FIGS. 4A-E) includes a large number of MGHs, vertical MSCs. and microfluidic control logic components. It has the following unique and useful features: (A) Each MGH 12 can flexibly regulate multiple climate/environmental variables, including RH. CO2, and light intensity (see also Section B4.1.1). Thus, a number of different plant growth environments can be simultaneously realized with an array of MGHs. The vertical MSCs 13 are sliding chip-like disposable components (Section B4.1.2). Each MGH 12 houses multiple MSCs 13. Multiple plants simultaneously grow in each vertical MSC 13 for a desired period of time (e.g., 7-28 days for the model plant *Arabidopsis*, depending on the size of the MGHs 12). (B) The vertical chip design for the MSCs 13 emulates normal gravitropic growth of plants, and facilitate easy and high-quality microscopic observation of plant phenotypes at the cellular as well as at organismal level, including seed germination, root growth, and shoot growth. Besides, the MSCs 13 can automatically trap individual seeds, change local environmental temperature via an integrated heater and thermal sensor, regulate chemical and hormone concentration, and introduce biological species (e.g., pathogens) via microfluidic approaches (Section B4.1.2). (C) The arrayed design of the plant growth system 10 is supported by well-established, reliable, on-chip microfluidic control logic technology with on-chip microvalves and micropumps [B24-27]. Specifically, the microfluidic control logic (e.g. reference numerals 41, 44, and 47 of FIG. 4A) addresses individual MGHs 12; the micro valves and micropumps (FIG. 4E) will control relevant microscale fluids to a selected MGH 12 to change environmental parameters (e.g., RH and CO2) inside the MGH 12 (Section B4.1.3). Therefore, the plant phenotyping instrumentation 10 will facilitate in regulating physical/chemical/biological environments with high flexibility, accuracy and fast speed, to reduce chemical/biological agents and energy consumption, to realize automation and avoid contamination during seed preparation, and more importantly, to obtain high throughput and data statistic for parallel processing.

Figure 6B:
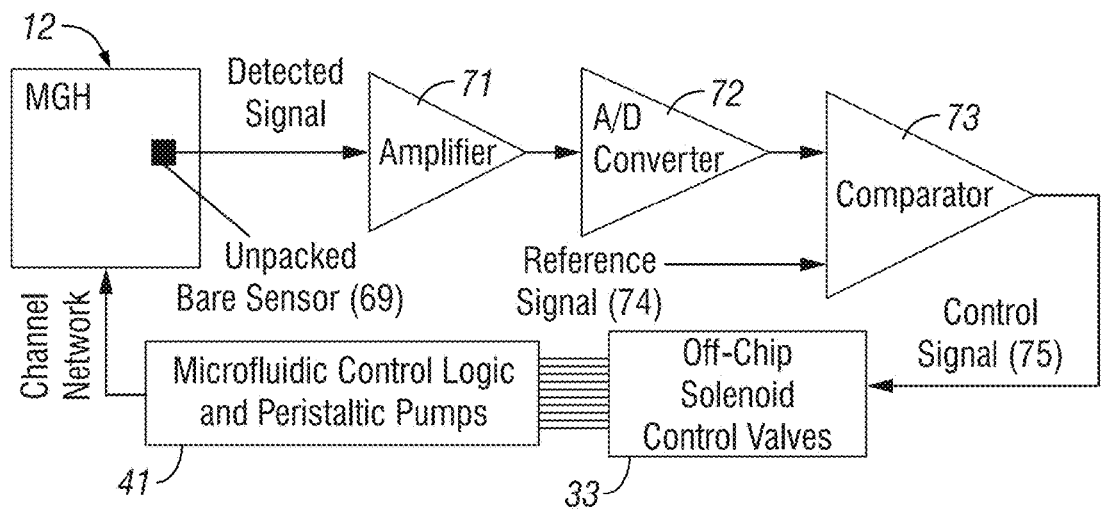
FIG. 6B is an electrical circuit diagram for sensor feedback and control of the fluid pump of FIG. 6A.

To reduce the complexity involved in system integration, a closed-loop sensor readout and electronic controller 36 (with wires 37 and 38) and a set of solenoid air control valves 33 are designed and built off the chip (FIGS. 3, 4A and 6B). Specifically, the sensor readout and electronic controller function i) to read out real-time signals from bare/unpacked RH and CO2 sensors partially embedded in the substrate of the MGHs. and from integrated temperature sensors on the MSCs (see, e.g., RH sensor 69 of FIG. 6A, CO2 sensor 89 of FIG. 7A, and temperature sensor 131 of FIG. 9A); and ii) to generate signals to control the external solenoid air valves, triggering an appropriate microfluidic control logic to adjust the environmental parameters (FIGS. 4A-E). The off-chip solenoid control valves function to actuate the microfluidic control logic and the on-chip valves and pumps (FIGS. 4A-E). Fluid inputs and outlets (e.g. line 35 to waste container 34) can be used. More specifically, FIGS. 4A-E illustrate the following. FIG. 4A is an overall schematic for an exemplary integrated plant growth system 10 for large-scale, high-throughput plant phenotyping. FIG. 4B shows one possible form of a single MGH 12 capable of regulating RH, CO2 level, and light intensity. For the purpose of describing the device structure only, Layers 1 and 2 are separated. As will be appreciated, variations on communication of electrical signals in possible. For example, instead of wired connections, some or all could be wireless by techniques know in the technical art.

The four transparent vertical walls 21-24 of MGH 12 define the interior space 20 of MGH 12. A light intensity regulator 100 encloses the top of space 20. Layer 1, an RH regulator 60, and Layer 2, a CO2 regulator 80, form the bottom of space 20 and the base for each MGH 12 (to mount on platform 11).

Figure 4C:
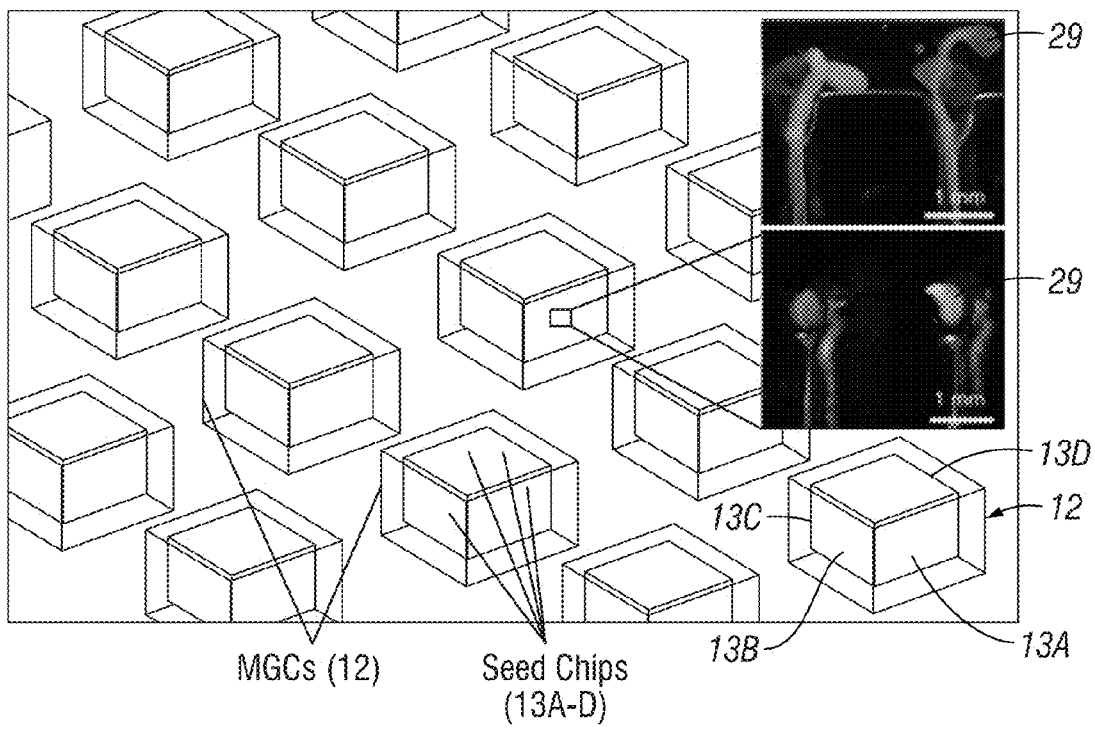
FIG. 4C is a diagrammatic illustration of placement of the MGHs of FIG. 4B in an array on a platform for the system of FIG. 3.
Figure 4D:
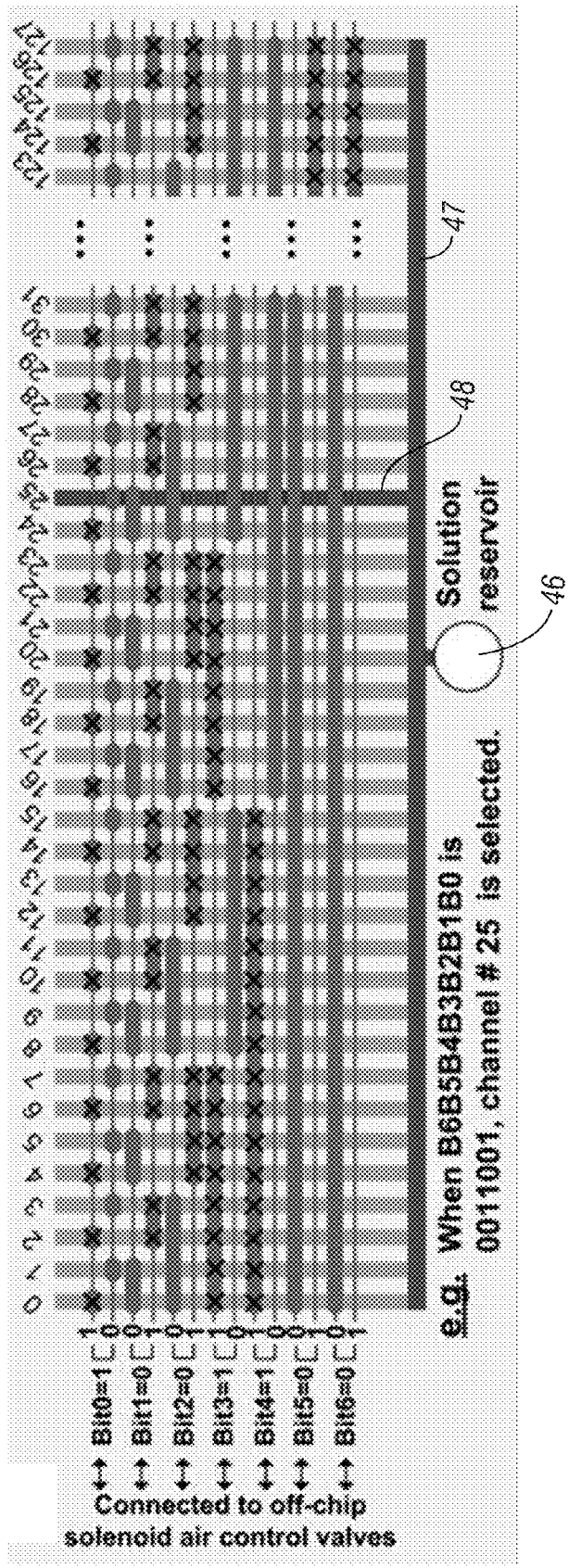
FIG. 4D is a logic diagram for one state possible with the microfluidic control logic of FIG. 4A.
Figure 4E:
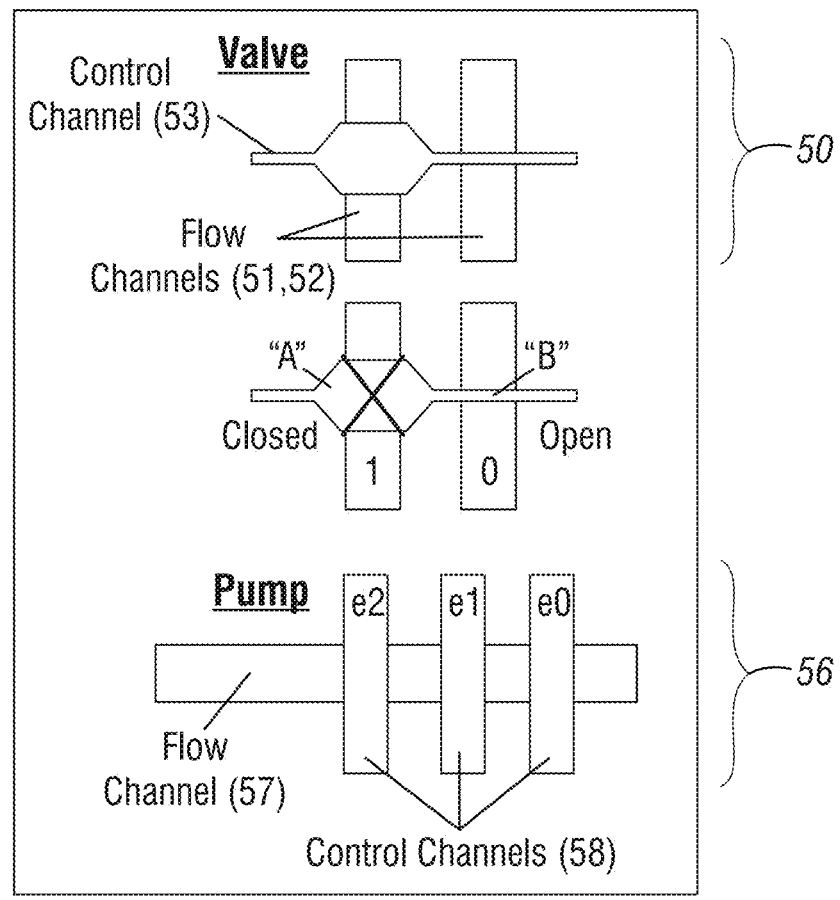
FIG. 4E are enlarged diagrammatic illustrations of types and states of microfluidic control components used with the circuit and logic of FIGS. 3 and 4A-D.

FIG. 4C is a diagrammatic depiction of part of an array of 128 MGHs 12 each with MSCs 13. Multiple (here 4) MSCs 13A-D are vertically inserted into each MGH 12. The insertion in FIG. 4C are images of: wild-type *Arabidopsis* are grown on a MSC at day 1 (lower) and day 10 (upper). FIG. 4D is a diagram of microfluidic control logic for addressing 128 MGHs and for controlling flow to a selected MGH. FIG. 4E is diagrammatic depictions of microfluidic control logic, namely an on-chip microvalve 50 (with a control channel 53 and flow channels 51, 52), and a peristaltic pump 56 (with control channels 58 and flow channel 57). Notations in FIGS. 4A-E illustrate how the control logic can individually address each valve 50 and pump 56 for each MSC 13 in each MGH 12. These are one example of the form and function that can be used for a system 10. Others are of course possible, as will be appreciated by those skilled in this technology art.

A robotic arm-assisted stereo microscopic imaging system 17 and 18 (FIG. 3) serves to image plant growth in the MSCs 13. This system 17, 18 collects phenotypic data of interest in a real-time manner at high spatial and temporal resolution (see, e.g., image samples in FIGS. 9D-J), including seed phenotype (e.g., size, color, germination, etc.), root phenotype (e.g., length, diameter, amount of lateral branching and length of specific zones within the root, etc.), shoot phenotype (e.g., hypocotyl emergence and length, cotyledon emergence and color, leaf emergence and number of leaves, etc.), and even cell phenotype (e.g., cell division, elongation, and maturation). These images provide a rich dataset for analyzing tools to facilitate large-scale plant phenotyping. Note that the hydroponic growth of plants within transparent microfluidic devices provides a high-resolution nondestructive view of phenotypes at the cellular as well as at the organismal level.

Model Plant *Arabidopsis thaliana*:

As one of the most important model plants in plant biotechnology, *Arabidopsis* offers excellent opportunities for providing key insights into the influence of genetic interactions and environmental conditions on plant productivity and yield. The availability of complete genome sequence and large number of genome-wide resources, and the ease with which results from *Arabidopsis* can be extrapolated to crop plants also make it an ideal organism for genomics as well as phenomics studies [B28].

Scalability of the Instrument for Different Growth Stages of *Arabidopsis* Plants and for Other Species:

To accommodate different growth stages and recording phenotypes over different time periods, the dimensions of MGHs and MSCs can be flexibly scaled up and down during structure design and fabrication processes. This is because the mechanisms for regulating environmental conditions in the MGH and MSC are largely independent of the volume/size of the MGH and MSC. This makes it possible to form a cube-shaped (or other form factor) MGH having an edge length of up to several inches. In comparison, FIG. 16A gives dimensions for one embodiment of an MSC 13 for *Arabidopsis* seeds and plants. The size of the MSC is also changeable following the size of the MGH. The number of seeds and the size of seed holding sites in the MSC can be varied flexibly as well, depending on the seed size and growth stages of the plant. Therefore, multiple versions of the instrumentation can be realized to accommodate different plant growth stages of interest. The instrumentation is capable of offering a considerable large number of different sets of environments, with each set including RH, CO2, light, temperature, chemicals (e.g., salt, hormone, etc.), and pathogens. Several hundreds to several tens of thousands of *Arabidopsis* plants can be simultaneously grown in one single system under the multiple sets of environments for high-throughput, large-scale plant phenotyping. Furthermore, due to the flexibility in changing geometry and shape of the MGHs and MSCs, the instrumentation can attract different users working with different plant species, and will not be limited to *Arabidopsis* only.

B3. Instrumentation Benefits

Currently, plant phenomics studies rely mainly on culturing seeds and growing plants in soil pots and agarose plates using culture facilities (e.g., greenhouse and plant growth chamber) with controlled environments, and on using imaging technologies to measure plant characteristics and performance in real time [B29-36]. While progress has been made in this area, insufficient technical and conceptual capacity imposes a strict limitation to conduct a large number of experiments for studying plant-environment interactions in a cost-effective and timely manner. With the model plant *Arabidopsis*, large-scale studies at high spatial/temporal resolution were difficult previously for the cost and greenhouse needs, and thus, only few studies with a few thousand mutants were done (the largest was 4,000 mutants) under specific environments.

B3.1 Existing Large Phenotyping Facilities and Limitations

Several high-throughput plant phenotyping facility and measurement systems, such as the Australian Plant Phenomics Facility and the PhenoFab in Netherlands are currently available for phenomics studies [B37, 38]. Controlled environments and automated imaging analysis are the two main technologies involved in these plant phenotyping facilities. The controlled growth environmental conditions (e.g., temperature, light, RH, CO2), provided by *Lemna* Tec [B39], are supported by a conveyor system for greenhouses and growth chambers. Specifically, the pots and plates with plants are moved through a growth compartment and scanned at preset time points from various angles to capture digital images. However, there are several concerns worth noting. First, screening of plant phenotypes using greenhouses or growth chambers is costly and the number of experiments is limited. Changing climate conditions of a greenhouse or plant growth chamber requires accessories such as water spray system, heater, and air ventilation system. The flexibility, accuracy and speed of changing environments are thus low. These issues become exacerbated when multiple climate-controlled chambers are needed for growing plants in parallel under various environments (with each chamber providing a specific set of growth conditions). Second, due to the use of pots and plates, a relatively large amount of chemicals and biological species is needed. Energy consumption is another concern for using multiple growth chambers. Third, since current practices for monitoring root growth behaviors in laboratory are often limited to non-transparent soil pots and agarose plates, the resultant spatial resolution of morphological measurements for seed, root, and shoot phenotypes is on the millimeter scale [B35, 40]. Microscopic real-time observation of cellular behaviors (e.g., cell division, elongation, host-pathogen interactions) on the micrometer resolution is not easy. Lastly, the low temporal resolution may lead to missing information about progressive and subtle changes in plant phenotypes during plant growth.

B3.2 Existing Miniature Phenotyping Devices and Limitations

The applications of microsystems and lab-chip technologies have facilitated high-throughput studies at the organismal level [B41-63] at significantly reduced costs and experimental times, while concomitantly increasing the accuracy of experiments. Recently, Guido et al. developed a root chip for characterizing phenotypic changes of multiple roots. The device contained separate chambers for individual delivery of chemical medium for multiple roots from multiple seedlings [B64]. *Arabidopsis thaliana* seeds germinated and grew in conventional pipettes in the first few days and then transferred into the device. Because seed germination and initial seedling growth was conducted outside the device, important early-stage phenotypic information was lost. Another issue is that the device only allowed for observation of root phenotypes, but was unable to observe changes in other plant organs inside the pipettes. Dong et al also developed a planar microfluidic seed chip capable of germinating multiple *Arabidopsis thaliana* seeds and setting different growth temperature via a size controllable nanofiber technology [B65]. Both seed germination and seedling growth were successfully realized in optically transparent microfluidic channels of the chip. These studies have shown the potential of using microfluidics technology for high-throughput plant phenomics analysis. But, all of the existing microfluidic technologies only allowed for studying the influence of a specific environmental parameter on roots [B64-68]. To the best of our knowledge, a high-throughput, automated shoot and root phenotyping instrumentation, capable of flexibly creating various environments, is not achieved yet.

B3.3 Significance of the Instrumentation

Figure 5:
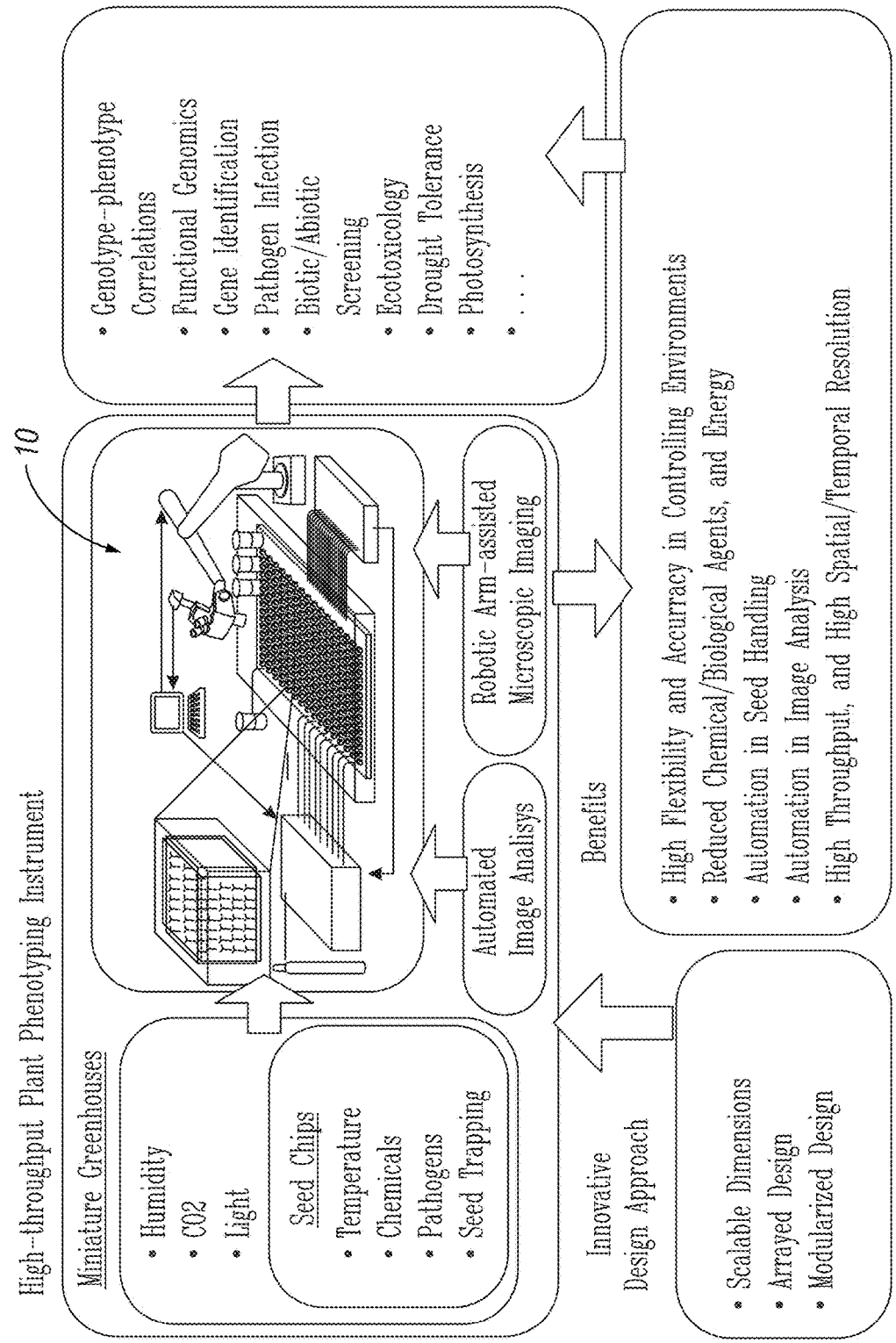
FIG. 5 is an annotation of the diagram of the system of FIG. 3.

The instrumentation will lead to the development of a high-throughput, large-scale phenotyping platform for screening of plant growth-environment interactions. The system will largely facilitate plant phenotyping experiments that are impossible by current techniques, constituting a significant leap in throughput and information content over existing plant phenotype assays. These capabilities are important in providing key insights into the genetic control of plant growth, health, and quality at the organismal level, as well as plant genotypes that produce valuable traits. The system will lead to rapid discovery of various phenotypes and the underlying genes that control the phenotypes under different environments, and thus, will benefit a wide range of researchers in plant biology community (e.g., functional genomics, phenomics, etc.). See FIG. 5 for additional details on the benefits and interoperability of the features of system 10 according to one embodiment of the invention.

B4. Specific Examples

The system 10 involves design, fabrication, and integration of the plant growth platform.

B4.1 Task 1: High-Throughput, Large-Scale Plant Phenotyping System

B4.1.1 Function Modules for MGHs

The MGHs 12 are capable of tuning environmental parameters such as RH, CO2 level, and light intensity, to facilitate study of plant-environment interactions.

A. Microfluidic On-Chip Humidity Generator:

Basically, RH is defined as the ratio of the amount of water vapor actually in the air compared to the amount of water vapor required for saturation at a particular temperature. At room temperature, about 150 nL water is needed to saturate water vapor (RH=100%) inside a MGH with a volume of 1×1×1 in$^3$ at room temperature. It would be challenging if one intends to control the RH inside this small space by conventional water spray and air ventilation systems. In the disclosed instrument 10, a microfluidic on-chip humidity generator 60 uses a controlled microfluidic capillary filling mechanism to regulate the internal RH of the greenhouse 12 from ~5 to 100% with a conservative step of ~1%. This method eliminates the need for water spray and air ventilation systems. As shown in FIG. 6A, a number of open shallow capillary channels 62 (only a few m deep) are structured on the floor of the MGH 12. Water comes from a reservoir 40 (with control logic and lines 41 and 42) located outside the MGH 12 and crosses over the sidewall 21 of the MGH 12 into the capillaries 62 through a conduit ("selected channel" of FIG. 6A) underneath the sidewall 21. Then, it evaporates into vapor that diffuses until a uniform vapor distribution is obtained within the MGH 12. The use of the multiple open shallow capillaries 62 allows for fast evaporation of water. Simulation and experimental results (FIGS. 11A-D) demonstrated that a 5 μm thick water sheet could become vapor completely in only several minutes at room temperature. FIGS. 11A-D show an image of an early-version MGH (FIG. 11A); RH vs. water column delivered to that MGH (FIG. 11B); RH vs. time for that MGH (FIG. 11C); and RH stability before and after water compensation (FIG. 11D).

A peristaltic pump (FIGS. 6A and 4E, and Section B4.1.3A) is used to control the volume of water delivered to the capillaries 62. Since each pumping cycle can result in injecting a liquid volume less than 0.1 nL (vs. ~150 nL for 100% RH) (section B4.1.3A), it is possible deliver an accurate amount of water into the capillaries 62 to obtain desired RH in the MGH 12. Note that RH inside the MGHs 12 may change due to the absorption of water moistures by surrounding materials and due to changing external temperature. To keep a desired RH stable, an off-chip electronic controller 41 detects the internal RH and controls the on-chip peristaltic micropump real time (FIG. 6B). Specifically, a bare RH microsensor 69 (FIGS. 6A and 6B) is partially embedded in the floor of MGH 12. The RH data is read out by the electronic controller. When the detected data are lower than the desired settings, the controller feeds a signal to the off-chip solenoid air control valves 33 (FIG. 3). Subsequently, the microfluidic control logic and peristaltic pumps are activated to deliver an amount of compensating water to the floor of the MGH. FIG. 6B shows one possible circuit: sensor 69 outputs its signal to amp 71, A/D convertor 72; that conditioned signal is compared to reference signal 74; the resulting output of comparator 73 is a control signal 75 that instructs valves 33, which control pumps or valves 41. Others are, of course, possible.

B. Microfluidic On-Chip CO2 Generator:

A conventional approach for controlling CO2 level in a greenhouse or growth chamber is to introduce CO2 directly from a gas cylinder. This involves using a bulky gas source, a pressure regulator, and a high resolution flow meter. Since an MGH 12 is small, delivery of a small amount of CO2 is a challenging task. In the disclosed instrument 10, a microfluidic on-chip CO2 generator 80 uses controlled chemical reactions underneath the floor of an MGH 12 (FIGS. 7A-D). This approach eliminates the need for a bulky CO2 delivery and regulation setup. As shown in FIGS. 7A-D, the solutions A ($NaHCO_3$) and B ($CH3COOH$) (see reference numbers 43 and 46 and ports 90 and 91 respectively; with control logic and lines 44,45 and 47,48 respectively) are pumped to a channel through a zigzag mixer 92 by using two individual 3-valve peristaltic pumps 56 (FIG. 7B; also see FIG. 4E). Then, both pumps 56 are closed. The reaction product is a mixture of CO2, CH3COONa, and H2O, according to $NaHCO3+CH3COOH \rightarrow CH3COONa+CO2+H2O$ (FIG. 7C). Subsequently, one of the source solutions (NaHCO3) is pumped to flush gently the gas-liquid mixture downstream to an on-chip waste reservoir 96 and/or an off-chip waste reservoir W through a spiral reaction channel 94 (FIGS. 7A, B, C, and D). Multiple tiny gas outlet holes 95 are structured along spiral reaction channel 94. These holes are pretreated hydrophobic (see also FIGS. 12A-D). FIGS. 12A-D show CO2 generation (FIGS. 12A-C) and CO2 concentration in a 1-in$^3$ chamber vs. flow rate of NaHCO3 and CH3COOH.

Thus, as the CO2-liquid mixture can flow downstream to pass by these holes 95, the CO2 bubbles 97 enter the holes 95 (see cross-sectional view of the device in FIG. 7D), while the aqueous solution doesn't. To block moisture entering the MGH above the spiral reaction channel 94, a CO2 permeable membrane filter 82 is placed on the floor of the MGH 12. Here, the amount of CO2 in the original product is determined by the amount of the source solutions 43, 46 delivered. The reaction speed can be adjusted by changing source solution concentration, and/or by pumping frequency. That CO2 partially dissolves to water. But, because the gas outlet ducts 95 are distributed along a long spiral reaction channel 94 and the gas-liquid solution keeps moving during collecting, the CO2 dissolution is limited and the amount of CO2 collected is controllable (see the previous result in FIGS. 12A-D). Similarly, the CO2 level may decrease because of consumption by plants and/or by possible absorption by surrounding materials. Thus, an off-chip electronic controller (FIG. 6B), in conjunction with a bare CO2 sensor 89, are used to keep a desired CO2 level stable. The two peristaltic micropumps 56 are called by the signal from the sensor 89 to control two chemical reaction source solutions 43, 46.

C. Light Intensity Generator:

A liquid crystal (LC)-based ceiling 100 is used for each MGH 12 (FIG. 8). This ceiling allows users to change internal light intensity by up to ~60 fold (see the preliminary result in FIGS. 13A-D). Specifically, nematic LCs 102 are injected into a space defined by two glass slides 104. Both of the slides 104 are coated with transparent conducting film electrodes 103 such as indium tin oxide (ITO). Two orthogonal polarizing films 105 are adhered to the two slides 104. A DC voltage applied to the electrodes causes to reorientate LC molecules [B69], modulating the refractive index of LCs 102, and thus, switching from an opaque to a transparent state. FIGS. 13A-C show images of light switching of a LC light shutter. FIG. 13D shows a graph of light intensity change vs. applied DC voltage in an LC light shutter of the type of FIG. 8.

B4.1.2 Vertical MSCs

The vertical MSCs 13 are used for growing multiple plants inside the MGHs 12. Automated seed loading, growth temperature regulation, chemical concentration regulation, introduction of pathogens, etc. can be performed on the MSCs 13 (FIG. 9A). The MSCs 13 make it convenient to continuously monitor phenotypic changes in plants at the whole organismal level (FIG. 9D), including seed germination, root growth, and shoot growth, as well as at the cellular level (FIGS. 9E and 9F).

FIGS. 9A-J relate to the following. FIG. 9A is a schematic of a vertical MSC 13. FIG. 9B is a diagrammatic depiction of a seed trapping mechanism for MSC 13. FIG. 9C is a highly diagrammatic depiction of a microfluidic chemical concentration generator. FIG. 9D is a series of acquired images of germination and growth of wild-type (WT) *Arabidopsis* plants in a top-closed MSC 13. FIG. 9E are images of root development of WT *Arabidopsis*. FIG. 9F is a fluorescence image of growing root cells of GFP-im. FIG. 9G are images of color phenotype (WT vs. im mutant) acquired with system 10. FIG. 9H are color images of interaction between *Arabidopsis* and pathogen, *Phytophthera sojae*, such as can be carried out with system 10. FIG. 9I is an acquired image from system 10 of WT *Arabidopsis* plant growth in a top-opened MSC at 17 days. FIG. 9J is an image of *Arabidopsis* plants grown in a top-opened MSC.

A. Automated Seed Trapping and Loading:

Generally, *Arabidopsis* seeds are handled by using sterilized tools such as forceps. Since they are small, it is difficult to manually load thousands of seeds individually into the chips. Also, seeds may get contaminated during handling of seeds. Thus, in the disclosed instrument, a hydrodynamic trapping method is used to load seeds into seed sites with automation. As shown in FIG. 9B, multiple seeds 29 are first loaded into a seed stock site 127 and then pushed into a main channel 126. Sucking pressure via parts 124 is applied to force the seeds 29 to flow against the lower wall of the main channel 126. When a seed flows by a funnel-like seed site 123, the fluid streamlines and carries the seed entering there. Since the seed sites 123 are designed in the way that each funnel hosts only one seed 29, other seeds have to flow over this seed site 123 to successive seed sites 123. Thus, the seeds can be trapped.

B. Vertical Growth of Seeds in Microfluidic Channels:

Once the seeds are trapped, the channel 126 (see FIG. 9B) above the seed holding site 123 can sometimes (if enough room) be removed to allow plant growth for longer periods of time (FIG. 9I) and to observe phenotypes at later stages of growth beyond the early seedling stage. However, in the event that only seed germination or early seedling stages are to be observed, then the main channel 126 can either be opened or remain closed since a closed channel allows users to observe phenotypes for ~10 days (FIG. 9D).

Emulating normal gravitropic growth of plants, the shoots 122 grow up vertically and the roots 121 will enter the growth regions 125 below the seed trapping sites 123 in the MSCs 13. The root growth regions 125 are designed to be spreading out downward, emulating normal gravitropic growth of plants. Water, nutrients, chemicals, and/or pathogens of interest can be injected into growth regions from the lower channels 125. In a previous planar seed chip design [B65], the roots grew horizontally while shoots grew vertically (FIGS. 14A-D). This caused difficulty in imaging the whole plant growth, especially in observing the initial stage of seedling growth. In the vertical chip design, growing multiple plants in the same vertical plane allows observing not only roots, but shoots and leaves, without losing important plant growth information. FIG. 14A is a schematic of such a MSC. FIG. 14B is an image from an imager of an *Arabidopsis* seed growing in such a MSC. FIG. 14C is a graph of root length vs. time; while FIG. 14D is a graph of root width vs. time for such a MSC. FIGS. 15A and B are still further magnified images of root growth of WT *Arabidopsis* seed at day 1 (FIG. 15A) and day 3 (FIG. 15B).

C. Chemical Concentration Generation:

Chemicals (e.g., salt, hormone) can regulate plant growth. To facilitate high-throughput studies of plant responses to different chemical environments, a conventional universal microfluidic chemical concentration generator [B70] is used on the MSC 13. The generator 115 can provide different chemical concentrations to the growth regions on the chip 13. As shown in FIG. 9C, a channel network has two inlets 116 and multiple outlets 118. Each inlet is connected to syringes that contain solutions of chemicals of interest. As the fluid travels down the network 117, they are repeatedly split, mixed, and recombined. After several generations of branched systems 117, each output channel 118 contains different proportions of the infused solutions and connects to multiple growth regions. Also, biological species such as pathogens can be introduced to the channels (FIG. 9H).

D. Growth Temperature Regulation:

To change growth temperature, a zigzagged thin-film metal wire heater 130 is structured on the backside of the seed chip (see wire to 130 in FIG. 9A; see also FIG. 10K). Electric current through the heater 130 can cause heat dissipation, changing local temperature on the seed chip 13. To detect the local temperature, a thin-film metallic thermal sensor 131 (see wire in FIG. 9A) is located adjacent to the heating wire (see also FIG. 10K). The sensing principle is simple: electrical resistance of the metal wire follows an almost linear trend to temperature relationship. The temperature readout and the control circuit are realized on the off-chip controller, along with the control circuit for internal RH and $CO_2$ levels.

Fabrication Processes for MSCs:

All channels are first formed in a polydimethylsiloxane (PDMS) layer by using soft lithography with a thick photoresist as a master mold. The channel layer is then bonded to a glass substrate by oxygen plasma treatment. Subsequently, a nichrome thin film is evaporated on the other side of the glass, and then, is patterned to form the designed zigzagged wire heater by photolithography and wet etching. Similarly, a thin film of nickel (having a high temperature coefficient of resistance of ~0.6‰C) is evaporated and patterned to form the thermal sensor.

Development of a "Library" of MSCs:

Besides the development of the MSC described above for general purposes, other simpler versions can be developed to form a "library" of MSCs to meet specific application needs. For example (but not limited to), in the event that temperature modulation is not necessary, a version of MSC without the integrated heater/sensor can be chosen. On the other hand, if plants need to be grown at different temperatures but at same chemical concentration(s), another version of MSC having a temperature regulator but excluding a concentration generator may be utilized.

B4.1.3 Fabrication and Integration of MGHs and MSCs with Microfluidic Control Logic A. Microfluidic Control Logic and Pneumatic Valve and Pump Mechanisms:

A well-established, robust microfluidic control logic method is used to realize integration of MGHs with a minimal number of controlled inputs (FIG. 4D) [see also B24-27]. Briefly, a flow layer contains channels for flowing liquids, and a control layer contains channels that deflect a thin membrane valve into the flow channel and stop liquid flow when pressurized with air. Simultaneous addressing of multiple noncontiguous flow channels can be accomplished, by fabricating control channels of varying width while keeping the dimension of the flow channel fixed. Thus, a low pneumatic pressure in a control channel can close the flow channel "A" without closing off the flow channel "B" (FIG. 4E). By using multiplexed valve systems, a 7-Bit microfluidic control logic (7 off-chip solenoid control valves are used to control air pressure in control channels) can address 128 flow channels (see FIG. 4D for details). Furthermore, a linear array of pneumatic valves forms an on-chip peristaltic pump (FIG. 4E). For example, peristaltic pumping occurs when three valves are actuated in the digital pattern 101, 100, 110, 010, 011, 001, where 0 and 1 represent open and closed valves, respectively. The pumping frequency is controlled by the frequency of the off-chip solenoid control valves. Each cycle of the pump injects a well-defined volume of liquid, at the level of tens of picoliters (pLs). In the system, 30 off-chip solenoid air control valves (from compressed air source 31) are used (through tubes 32) to control the on-chip pneumatic valves, generating logic to address individual flow channels connecting to targeted MGHs. Specifically, as shown in FIGS. 4A and 4D, a6-a0 (7-Bit) can select a desired water flow, and then, c2-e0 (3-Bit) can drive a pump to deliver an accurate amount of water to a selected MGH, for changing RH (FIG. 6A) of that MGH. Similarly, b6-b0 and d2-d0 are for delivering chemical solution A. and c6-c0 and f2-f0 are for solution B. The solutions A and B react in channels to produce CO2 (FIGS. 7A-D).

B. Fabrication and Integration Processes:

Step 1: This step is to fabricate the microfluidic RH generators 60 and their corresponding microfluidic control logic unit. An air control channel layer 67 (with air channels 66), a flow channel layer 65 (with channels 64), and an open capillary channel layer 63 (with capillaries 62) are made of PDMS [B71] (FIGS. 10A-C) by high precision replica molding process. Due to the large area of the device, the master molds used in the replica molding process are formed by a high precision milling machine. The bare RH sensors 69 are partially embedded in the capillary open channel layer 63 during curing. Installation of CO2 sensor 61 is also completed in this step (FIG. 10C). The three PDMS layers 63, 65, and 67 are then bonded together via oxygen plasma treatment (FIG. 10D). To form the microfluidic control logic structures, valves, and peristaltic pumps, the flow channels are aligned orthogonal to the control channels. Through-holes are punched to connect the flow channels and the open capillary channels. A CO2 passage 68 is also be formed by punching through all three layers in this step (FIG. 10D). Step 2: This step is to fabricate the microfluidic CO2 generators 80 and corresponding microfluidic control logic units. The CO2 generators 80 are located below the RH generators 60 and have two microfluidic control logic units. By using the similar procedures as the previous steps, the main structures of the CO2 generators can be formed. An air control layer 87 (with air channels 86) is bonded to a flow channel layer 85 (with fluid channels 84). The gas ducts 95 to spiral reaction channel 9694 are then coated with octa-decyltrichlorosilane solution to form a hydrophobic surface. Then, a gas permeable membrane filter 82 (e.g., polyethersulfone, polypropylene, etc.) is placed above the CO2 ducts 95 (FIGS. 10C-G). Step 3: This step is to fabricate the growth chambers by the replica molding process (not shown in FIGS. 10A-K). This can proceed according to well-known processes. Step 4: This step is to fabricate multiple LC ceilings 100 to cap multiple MGHs 12 in an array. The fabrication process starts with coating two glass slides 104 with transparent conducting film (ITO) 103. Next, a 2-3 μm thick photoresist 106 is patterned along the edges of a slide. A cavity is then formed between the two slides by the photoresist spacer 106 (FIG. 10I). Subsequently, LCs 102 are loaded into the cavity. Two adhesive polarizing sheets 105 are then adhered to the two slides 104 (FIG. 10J). Multiple individual ITO electrodes are formed on one slide 104 such that the light intensity in each MGH 12 can be individually controlled. Step 5: This step is to assemble all the device components (except for the LC ceiling 100) via oxygen plasma treatment (FIG. 10K). To hold the MSCs 13, chip holding slots 26 (FIG. 1B) are formed inside the MGHs 12. Four MSCs 13A-D can be placed near (but not against) the sidewalls 21, 22, 23, 24 of the MGH 12, at an appropriate small angle from the vertical plane. In this way, the plants in lower channels of the MSC 13 are shaded. To build electrical and microfluidic connections between the inside and outside components, multiple holes are formed in the sidewalls 21-24 of the chambers 12. These holes are sealed later. An external electronic controller (in FIG. 6B) is needed to provide real-time readout of sensor output and consequent control of the off-chip solenoid air control valves.

C. Robotic Stereo Microscopic Imaging System:

The robotic plant imaging system 17, 18 consists of a programmable robotic arm 17 [B72] and a portable microscope with a camera 18 [B73], g., a high resolution colored video camera. The robotic arm 17 serves to move and rotate the microscope and camera 18 [B74]. The microscope can be programmed to change zoom settings. Therefore, the automated imaging system can take pictures for different plant growth regions on the MSCs 13 with different magnifications.

As can be appreciated by those having skill in this technology, the robotic arm 17 can have at least three degrees freedom of movement (or more) and have programmable highly precise movement. By appropriate programming and construction of at least substantially transparent portions or windows in the Miniature Greenhouse walls, the imager 18 on the robotic arm 17 can move to each MGH 12, assume a correct optical axis relative to the window and acquire very high resolution images of seeds or seedlings inside the MGH. Sometimes this will be at an angle to the seedling, sometimes orthogonal to it. One version of the MGH has all walls 21-24 of the MGH transparent. But as indicated herein, the spacing between MGHs and the articulation of the imager on the robotic arm can benefit from imaging of a vertically growing seedling, including the whole plant in some images and possibly zoomed in areas of interest on the plant. Whatever seed holder is used in the MGH, it also can be at least substantially transparent to promote good and clear imaging. Seed holders, including MSCs 13, could be positioned along or near vertical walls 21-24 of the MGH 12 to also promote imaging.

REFERENCES FOR SECTION B

B [1] P K Gupta, S Rustgi and R R Mir, Array-based high-throughput DNA markers for crop improvement, Heredity 101: 5-18 (2008).

B [2] J D Hoheise, Microarray technology: beyond transcript profiling and genotype analysis Nature Reviews Genetics 7: 200-210 (2006).

B [3] P Liu P, N Koizuka, T M Homrichhausen. J R Hewitt, R C Martin, and H Nonogaki, Large-scale screening of *Arabidopsis* enhancer-trap lines for seed germination-associated genes. Plant Journal 41:936-944 (2005).

B [4] D C Boyes, A M Zayed, R Ascenzi, A J MacCaskill, N E Hoffman, K R Davis, and J Gorlacj, Growth stage-based phenotypic analysis of *Arabidopsis*: A model for High-throughput functional genomics in plants. Plant Cell 13:1499-1510 (2001).

B [5] A Sessions, E Burke, G Presting, G Aux, et. al, A High-Throughput *Arabidopsis* Reverse Genetics System, The Plant Cell 14: 2985-2994 (2002).

B [6] M R Ponce, P Robles, and J L Micol, High-throughput genetic mapping in *Arabidopsis thaliana*. Molecular and General Genetics, 261: 408-415 (1999).

B [7] J M Alonso, A N Stepanova, T J Leisse, C J Kim, et al., Genome-wide insertional mutagenesis of *thaliana*, Science 301: 653-657 (2003).

B [8] Q Dong, S D Schlueter, and V Brendel, PlantGDB, plant genome database and analysis tools, Nucl. Acids Res. 32 (suppl. 1): D354-D359 (2004).

B [9] http://www.plantgdb.org/

B [10] P Zimmermann, M Hirsch-Hoffmann, L Hennig, and W Gruissem, GENEVESTIGATOR. *Arabidopsis* Microarray Database and Analysis Toolbox, Plant Physiology 136:2621-2632 (2004).

B [11] J K. C. Rose, S Bashir, J. Giovannoni, M. Jahn, R S Saravanan, Tackling the plant proteome: practical approaches, hurdles and experimental tools, The Plant Journal 39: 715-733 (2004).

B [12] M M Bushey and J W Jorgenson, Automated instrumentation for comprehensive two-dimensional high-performance liquid chromatography of proteins, Anal. Chem. 62: 161-167 (1990).

B [13] V Zabrouskov. L Giacomelli, K J van Wijk, and F W McLafferty. A new approach for plant Proteomics: Characterization of chloroplast proteins of *Arabidopsis thaliana* by top-down mass spectrometry, Mol Cell Proteomics 2:1253-60 (2003).

B [14] L W Sumner, P Mendes, and R A Dixon, Plant metabolomics: large-scale phytochemistry in the functional genomics era, Phytochemistry 62: 17-836 (2003).

B [15] D Houle, D R Govindaraju, and S Omholt, Phenomics: the next challenge, Nature Reviews Genetics 11: 855-866 (2010).

B [16] R T Furbank and M Tester, Phenomics—technologies to relieve the phenotyping bottleneck, Trend in Plant Science 16: 635-644 (2011).

B [17] M N Hemming, S A Walford, S Fieg, E S Dennis, and B Trevaskis, Identification of high temperature responsive genes in cereals, Plant Physiology 111: 192013 (2012).

B [18] M Levin. N Resnick, Y Rosianskey, I Kolotilin, S Wininger. J H Lemcoff, et al., Transcriptional profiling of *Arabidopsis thaliana* plants' response to low relative humidity suggests a shoot-root communication, Plant Science 177: 450-459 (2009).

B [19] C Kami, S Lorrain. P Hornitschek, and C Fankhauser. Light-Regulated Plant Growth and Development, Current Topics in Developmental Biology 91: 29-66 (2010).

B [20] B Berger, B Parent, and M Tester, High-throughput shoot imaging to study drought responses. J. Exp. Bot. 61: 3519-3528 (2010).

B [21] J K Ward and J K Kelly, Scaling up evolutionary responses to elevated CO2: lessons from *Arabidopsis*, Ecology Letters 7: 427-440 (2004).

B [22] J K. Zhu, Plant salt tolerance, Trend in Plant Science 6: 66-71 (2001).

B [23] Y H Cheong. H-S Chang, R Gupta, X Wang, T Zhu, and S Luan, Transcriptional Profiling Reveals Novel Interactions between Wounding, Pathogen, Abiotic Stress, and Hormonal Responses in *Arabidopsis*, Plant Physiology 129: 661-677 (2002).

B [24] T Thorsen, S J Maerkl, and S R Quake, Microfluidic large-Scale Integration, Science 298: 580-584 (2002).

B [25] J Melin and S R Quake, Microfluidic Large-Scale Integration: The Evolution of Design Rules for Biological Automation, Annu Rev Biophys Biomol Struct. 36: 213-231 (2007).

B [26] S R Quake and A Scherer, From micro to nano fabrication with soft materials. Science 290:1536-1540 (2000).

B [27] M A Unger, H P Chou, T Thorsen, A Scherer, and S R Quake, Monolithic microfabricated valves and pumps by multilayer soft lithography. Science 288:113-116 (2000).

B [28] C Bolle, A Schneider, and D Leister, Perspectives on systematic analyses of gene function in *Arabidopsis thaliana*: New tools, topics and trends. Current genomics 12:1-14 (2011).

B [29] T Kuromori. T Wada, A Kamiya. M Yuguchi, et al., A trial phenome analysis using 4000 Ds-insertional mutants in gene-coding regions of *Arabidopsis*. Plant J. 47:640-651 (2006).

B [30] T Kuromori, S Takahashi, Y Kondou, K Shonozaki, and M Matsui. Phenome analysis in plant species using loss-of-function and gain-of-function mutants. Plant Cell Physiology 50:1215-1231 (2009).

B [31] U Kolukisaoglu and K Thurow, Future and frontiers of automated screening in plant sciences, Plant Science 178: 476-484 (2010).

B [32] R T Clark, R B MacCurdy, J K Jung, J E. Shaff, S R. McCouch, D J. Aneshansley and L V Kochian, Three-Dimensional Root Phenotyping with a Novel Imaging and Software Platform, Plant Physiology 156: 455-465 (2011)

B [33] J M. Montes, A E. Melchinger, and J C Reif, Novel throughput phenotyping platforms in plant genetic studies, Trends in Plant Science, 12: 433-436 (2007).

B [34] S Trachsel, S M Kaeppler, K M Brown, and J P Lynch, Shovelomics: high throughput phenotyping of maize (*Zea mays* L.) root architecture in the field, Plant and Soil 341: 75-87 (2011).

B [35] A S Iyer-Pascuzzi, O Symonova, Y Mileyko, Y Hao, H Belcher, J Harer, J S. Weitz, and P N Benfey, Imaging and Analysis Platform for Automatic Phenotyping and Trait Ranking of Plant Root Systems, Plant Physiology 152: 1148-1157 (2010).

B [36] G W Bassel, P Fung, T F Chow, J A Foong, N J Provart, and S R Cutler, Elucidating the germination transcriptional program using small molecules. Plant Physiol. 147: 143-155 (2008).

B [37] http:/www.plantphenomics.org.au/

B [38] http://www.phenofab.com,

B [39] http:/www.lemnatec.com/

B [40] A French, S Ubeda-Tomas, T J Holman, M J Bennett, T Pridmore, High-throughput quantification of root growth using a novel image-analysis tool. Plant Physiology. 150: 1784-1795 (2009).

B [41] G M Whitesides, The origins and the future of microfluidics, Nature 442: 368-373 (2006).

B [42] S K Sia and G M Whitesides, Microfluidic devices fabricated in poly (dimethylsiloxane) for biological studies, Electrophoresis 24: 3563-3576 (2003).

B [43] D J Beebe, G A Mensing, and G M Walker, Physics and applications of microfluidics in biology, Annual Review of Biomedical Engineering 4: 261-286 (2002).

B [44] A J deMello, Control and detection of chemical reactions in microfluidic systems, Nature 442: 394-402 (2006).

B [45] G Lin and A P Lee, Microfluidics: an emerging technology for food and health science, Annals of the New York Academy of Sciences 1190: 186-192 (2010).

B [46] L F Kang, B G Chung, R Langer, et al., Microfluidics for drug discovery and development: From target selection to product lifecycle management, Drug Discovery Today 13: 1-13 (2008).

B [47] R Sista, Z S Hua, P Thwar, et al., Development of a digital microfluidic platform for point of care testing. Lab Chip 8: 2091-2104 (2008).

B [48] S Y Teh, R Lin, L H Hung, et al., Droplet microfluidics, Lab Chip 8: 198-220 (2008).

B [49] J Atencia and D J Beebe, Controlled microfluidic interfaces, Nature 437: 648-655 (2005).

B [50] B Zheng. L S Roach, and R F smagilov, Screening of protein crystallization conditions on a microfluidic chip using nanoliter-size droplets, Journal of The American Chemical Society 125: 11170-11171 (2003).

B [51] H Song. J D Tice, and R F Ismagilov, A microfluidic system for controlling reaction networks in time, Angewandte Chemie International Edition 42:768-772 (2003).

B [52] J Qin and A R Wheeler, Maze exploration and learning in *C. elegans*, Lab Chip 7: 186-192 (2007).

B [53] X Heng. Optofluidic microscopy-a method for implementing a high resolution optical microscope on a chip, Lab Chip 6, p. 1274-1276 (2006).

B [54] S E Hulme, A microfabricated array of clamps for immobilizing and imaging *C. elegans*, Lab Chip 7: 1515-1523 (2007).

B [55] G B Rohde, F Zeng. R Gonzalez-Rubio, et al., Microfluidic system for on-chip high-throughput whole-animal sorting and screening at subcellular resolution, Proc. Natl. Acad. Sci. USA 104: 13891-13895 (2007).

B [56] K Chung. Y Kim, J S Kanodia, et al., A microfluidic array for large-scale ordering and orientation of embryos. Nat. Methods 8: 171-176 (2011).

B [57] C Samara, C B Rohde, C L Gilleland, et al., Large-scale in vivo femtosecond laser neurosurgery screen reveals small-molecule enhancer of regeneration. Proc. Natl. Acad. Sci. USA 107: 18342-18347 (2010).

B [58] C Bermejo, J C Ewald, V Lanquar, et al., In vivo biochemistry: Quantifying ion and metabolite levels in individual cells or cultures of yeast. Biochem. J. 438: 1-10 (2011).

B [59] A Huebner, M Srisa-Art, D Holt, et al., Quantitative detection of protein expression in single cells using droplet microfluidics, Chemical Comm. 12: 1218-1220 (2007).

B [60] E Brouzes, M Medkova, N Savenelli, et al., Droplet microfluidic technology for single-cell high-throughput screening, Proc. Natl. Acad. Sci. USA 106: 14195-14200 (2009).

B [61] E M Lucchetta, J H Lee, L A Fu, N H Patel, and R F Ismagilo. Dynamics of *Drosophila* embryonic patterning network perturbed in space and time using microfluidics. Nature 434: 1134-1138 (2005).

B [62] C L Gilleland, C B Rohde, F Zeng, and M F Yanik, Microfluidic immobilization of physiologically active *Caenorhabditis elegans*. Nat. Protoc. 5: 1888-1902 (2010).

B [63] J Clausell-Tormos. D Lieber. J C Baret, et al., Droplet-based microfluidic platforms for the encapsulation and screening of mammalian cells and multicellular organisms, Chemistry & Biology 15: 427-437 (2008).

B [64] G Grossmann, W Guo, D W Ehrhardt, W B Frommer, R V Sit, S R Quake, and M Meier. The RootChip: an integrated microfluidic chip for plant science. Plant Cell 23: 4234-4240 (December 2011).

B [65] H W Jiang, Y. Jiao. M R Maneesha, and L Dong, Electrospun nanofibrous membranes for temperature regulation of microfluidic seed growth chips. Journal of Nanoscience and Nanotechnology 12: 6333-6339 (2012).

B [66] A Parashar and S Pandey, Plant-in-chip: Microfluidic system for studying root growth and pathogenic interactions in *Arabidopsis*, Appl. Phys. Lett. 98: 263703 (2011).

B [67] M Meier. E M Lucchetta, and R F Ismagilov, Chemical stimulation of the *Arabidopsis thaliana* root using multi-laminar flow on a microfluidic chip. Lab Chip 10: 2147-2153 (2010).

B [68] B Wolfgang, T M Brad, M Bradley, D L Mace. R W Twigg. J Jung. I Pruteanu-Malinici. S J Kennedy, G K Fricke, R L Clark, U Ohler, and P N Benfey, A microfluidic device and computational platform for high-throughput live imaging of gene expression, Nature Methods, 9, 1101-1106 (2012).

B [69] L Komitov, G Hegde and D Kolev, Fast liquid crystal light shutter, J. Phys. D: Appl. Phys. 44: 442002 (2011).

B [70] S K W Dertinger, D T Chiu, N L Jeon, and G M Whitesides, Generation of Gradients Having Complex Shapes Using Microfluidic Networks, Anal. Chem. 73: 1240-1246 (2001).

B [71] G M Whitesides, E Ostunil. S Takayama, X Jiang, and D E Ingber, Soft lithography in biology and biochemistry, Annual Review of Biomedical Engineering 3: 335-373 (2001).

B [72] http://www.strobotics.com/articulated-robot-arm.htm

B [73] http://www.leica-microsystems.com/products/stereo-microscopes-macroscopes/research-automatedidetails/product/leica-z6-apo-a/

B [74] http:i/spectraservices.com/OPTSCN.html

B [75] Z Xu, Y Jiao, and L Dong, Microfluidic humidity regulator (under preparation)

B [76] L Wang, L V Uilecan, A H Assadi, C A Kozmik, and E P Spalding, HYPOTrace: Image analysis software for measuring hypocotyl growth and shape demonstrated on *Arabidopsis* seedlings undergoing photomorphogenesis, Plant Physiology 149: 1632-1637 (2009).

B [77] X Qi, J Qi, and Y Wu, RootLM: a simple color image analysis program for length measurement of primary roots in *Arabidopsis*. Plant Root 1: 10-16 (2007).

B [78] C Qiu and N Vaswani, "Real-time robust principal components' pursuit," in Allerton Conf. on Communication, Control, and Computing (2010).

B [79] C Qiu and N Vaswani, "Reprocs: A missing link between recursive robust pca and recursive sparse recovery in large but correlated noise," arXiv: 1106.3286 (2011).

B [80] Y Li, L Xu, J Morphett, and R Jacobs, "An integrated algorithm of incremental and robust pca," in IEEE Intl. Conf. Image Proc. (ICIP) 245-248 (2003).

B [81] E Candes, X Li, Y Ma, and J Wright, "Robust principal component analysis?," Journal of the ACM (2011).

B [82] F. De La Torre and M. J. Black, "A framework for robust subspace learning," International Journal of Computer Vision, 54, 117-142 (2003).

B [83] N Vaswani and W Lu. "Modified-cs: Modifying compressive sensing for problems with partially known support," IEEE Trans. Sig. Proc., 58: 4595-4607 (2010).

B [84] C Qiu and N Vaswani, "Support-predicted modified-cs for principal components' pursuit," in IEEE Intl. Symp. Info. Th. (ISIT) (2011).

B [85] N Vaswani, "Particle Filtering Algorithms for Multimodal Observation Likelihoods and Large Dimensional State Spaces," IEEE Trans. Signal Proc., 56, 4583-4597 (2008).

B [86] N Vaswani. Y Rathi, A Yezzi, and A Tannenbaum. "Deform PF-MT: Particle Filter with Mode Tracker for Tracking Non-Affine Contour Deformations," IEEE Trans. Image Processing, 19: 841-857(2010).

B [87] A K Livingston, J A Cruz, K Kohzuma, A Dhingra, and D M Kramer, An *Arabidopsis* Mutant with High Cyclic Electron Flow around Photosystem I (hcef) Involving the NADPH Dehydrogenase Complex, The Plant Cell, 22: 221-233 (2010).

B [88] G J. Budziszewski, S P Lewis, L W Glover, et al., *Arabidopsis* Genes Essential for Seedling Viability: Isolation of Insertional Mutants and Molecular Cloning, Genetics. 159: 1765-1778 (2001).

B [89] C R Somerville, Analysis of photosynthesis with mutants of higher plants and algae, Annu. Rev. Plant. Physiol., 37: 467-507 (1986).

B [90] S Lefebvre, T Lawson, O V Zakhleniuk. J C Lloyd, and C A Raines. Increased Sedoheptulose-1,7-Bisphosphatase Activity in Transgenic Tobacco Plants Stimulates Photosynthesis and Growth from an Early Stage in Development, Plant Physiol., 138: 451-460 (2005).
B [91] X Yi, S Hargett, L Frankel, and T Bricker, The PSbQ protein is required in *Arabidopsis* for photosystem II assembly/stability and photoautotrophy under low light conditions. J. Biol. Chem. 281:26260-26267 (2006).
B [92] N Nelson and C Yocum, Structure and function of photosystem I and II. Annu. Rev. Plant. Physiol., 57:521-565 (2006).
B [93] H Scheller and A Haldrup, Photoinhibition of photosystem I. Planta, 221:5-8 (2005).
B [94] M R Aluru, H Bae, D Wu, and S R Rodermel, The *Arabidopsis* immutans mutation affects plastid differentiation and the morphogenesis of white and green sectors in variegated plants. Plant Physiology, 127:67-77 (2001).
B [95] C Cazonelli and B Pogson, Source to sink: regulation of carotenoid biosynthesis in plants. Trends in Plant Science, 15: 266-274 (2010).
B [96] A Biehl, E Richly, C Noutsos, F Salamini, and D Leister. Analysis of 101 nuclear transcriptomes reveals 23 distinct regulons and their relationship to metabolism, chromosomal gene distribution and co-ordination of nuclear and plastid gene expression. Gene, 344:33-41 (2005).
B [97] S Ficklin, F Luo, and F Feltus, The association of multiple interacting genes with specific phenotypes in rice using gene coexpression networks. Plant physiology 154: 113-124 (2010).
B [98] M R Aluru, J Zola. D Nettleton, and S Aluru. Reverse engineering and analysis of large genome-scale gene networks. Nucleic Acids Research (in press).
B [99] H Jiang, Z Xu, M R Aluru, and L Dong. Plant-chip for high-throughput phenotyping of *Arabidopsis*, Lab on a Chip, 14, 1281-1293 (2014)
B [100] D. Mao, M. Li. W. Y. Leung, K. M. Ho, and L. Dong. Photonic-plasmonic integration through the fusion of photonic crystal cavity and metallic structure. Journal of Nanophotonics, 5(1):059501-059501 (2011).
B [101] D. Mao, P. Liu, and L. Dong. All-optical programmable photonic integrated circuit: An optical analogy to electronic FPGA. 16th International Conference on Solid-State Sensors, Actuators and Microsystems, 2674-2677 (2011).
B [102] D. Mao, P. Liu. and L. Dong. Multichannel detection using transmissive diffraction grating sensor. Journal of Polymer Science Part B: Polymer Physics, 49(23):1645-1650 (2011).
B [103] D. Mao, P. Liu, K. M. Ho, and L. Dong. A theoretical study of a nano-opto-mechanical sensor using a photonic crystal-cantilever cavity. Journal of Optics, 14(7):075002 (2012).
B [104] H. Yang, X. Qiao, M. K. Bhattacharyya. and L. Dong. Microfluidic droplet encapsulation of highly motile single zoospores for phenotypic screening of an antioomycete chemical. Biomicrofluidics, 5(4):044103 (2011).
B [105] H. Yang and L. Dong. Selective nanofiber deposition using a microfluidic confinement approach. Langmuir. 26(3):1539-1543 (2009).
B [106] P. Liu, D. Mao, R. Martin, and L. Dong. An integrated fiber-optic microfluidic device for detection of muscular force generation of microscopic nematodes. Lab on a Chip, 12(18):3458-66 (2012).
B [107] H. Yang, X. Qiao, W. Hong, and L. Dong. Core-shell microcapsules with embedded microactuators for regulated release. IEEE Journal of Microelectromechanical systems. 22: 509-518 (2013).
B [108] H. Yang, M K Bhattacharyya. and L. Dong. Plant pathogen spores grow in microfluidic droplets: A high-throughput approach to antifungal drug screening. 16th International Conference on Solid-State Sensors, Actuators and Microsystems Conference, 2011, 2235-2238 (2011).
B [109] H. Yang and L. Dong. Smart drug delivery using electrospun hollow nanofibers. IEEE 23rd International Conference on Micro Electro Mechanical Systems (MEMS), 308-311(2010).
B [110] X. Yu, L. Li, J. Zola, M. Aluru. H. Ye. A. Foudree, H. Guo, S. Anderson, S. Aluru, P. Liu, S. Rodermel, Y. Yin. A brassinosteroid transcriptional network revealed by genome-wide identification of BES1 target genes in *Arabidopsis thaliana*. The Plant Journal, 65, 634 (2011)
B [111] A. Sarje, J. Zola and S. Aluru. Accelerating pairwise computations on Cell processors. IEEE Transactions on Parallel and Distributed Systems, 22, 69-77 (2011).
B [112] J. Zola, M. Aluru, A. Sarje and S. Aluru. Parallel information theory based construction of gene regulatory networks. IEEE Transactions on Parallel and Distributed Systems, 21, 1721-1733 (2010)
B [113] J. Zola, A. Sarje and S. Aluru. Constructing gene regulatory networks on clusters of Cell processors. Proc. 38th International Conference on Parallel Processing, 108-115 (2009)
B [114] O. Nikolova, J. Zola and S. Aluru. A parallel algorithm for exact Bayesian network inference. Proc. IEEE International Conference on High Performance Computing (HiPC), 342-349 (2009)
B [115] J. Zola, A. Sarje and S. Aluru. Constructing gene regulatory networks on clusters of Cell processors. Proc. International Conference on Parallel Processing (ICPP), 108-115 (2009)
B [116] J. Zola, M. Aluru and S. Aluru. Parallel information theory based construction of gene regulatory networks. Proc. IEEE International Conference on High Performance Computing (HiPC). Springer-Verlag Lecture Notes in Computer Science, 336-349 (2008)
B [117] C. Qiu and N. Vaswani. Support predicted modified-cs for recursive robust principal components' pursuit. In IEEE Intl. Symp. Info. Th. (ISIT) (2011).
B [118] R. Sarkar, S. Das, and N. Vaswani. Pafimocs: Particle filtered modified-cs and applications in visual tracking across illumination change. Submitted to IEEE Trans. Image Proc (2012).
B [119] W. Lu and N. Vaswani. Modified Compressive Sensing for Real-time Dynamic MR Imaging. In IEEE Intl. Conf. Image Proc. (ICIP) (2009).
B [120] W. Lu and N. Vaswani. Modified bpdn for noisy compressive sensing with partially known support. In IEEE Intl. Conf. Acoustics, Speech, Sig. Proc. (ICASSP) (2010).
B [121] N. Vaswani. Kalman filtered compressed sensing. In IEEE Intl. Conf. Image Proc. (ICIP) (2008).
B [122] N. Vaswani. Analyzing least squares and Kalman filtered compressed sensing. In IEEE Intl. Conf. Acoustics, Speech, Sig. Proc. (ICASSP) (2009).
B [123] N. Vaswani. LS-CS-residual (LS-CS): Compressive Sensing on Least Squares residual. IEEE Trans. Sig. Proc., 58(8):4108-4120 (2010).
B [124] N. Vaswani. Stability (over time) of Modified-CS and LS-CS for Recursive Causal Sparse Reconstruction. In ArXiv preprint arXiv:1006.4818 [cs.IT] (2010).

B [125] N. Vaswani. Stability (over time) of Modified-CS for Recursive Causal Sparse Reconstruction. In Allerton Conf. Communication, Control, and Computing (2010).

B [126] N. Vaswani and W. Lu. Modified-cs: Modifying compressive sensing for problems with partially known support. In IEEE Intl. Symp. Info. Th. (ISIT) (2009).

B [127] S. Das and N. Vaswani. Model-based Compression of Nonstationary Landmark Shape Sequences, Proceedings of IEEE International Conference on Image Processing (ICIP) (2008)

B [128] A. Kale and N. Vaswani. Generalized ELL for Detecting and Tracking Through Illumination Model Changes. Proceedings of IEEE International Conference on Image Processing (ICIP) (2008).

B [129] N. Vaswani and S Das. Particle Filter with Efficient Importance Sampling and Mode Tracking (PF-EIS-MT) and its Application to Landmark Shape Tracking, Proceedings of the Asilomar Conference on Signals. Systems and Computers (2007)

B [130] C. Qiu, W. Lu and N. Vaswani. Real-time Dynamic MR Image Reconstruction using Kalman Filtered Compressed Sensing, IEEE Intl. Conf. Acous. Speech. Sig. Proc. (ICASSP) (2009).

B [131] S. Das and N. Vaswani. Efficient importance sampling techniques for large dimensional and multimodal posterior computations. IEEE Digital Signal Processing/SPE Workshop, Miami Fla., January 2009 (invited).

B [132] W. Lu and N. Vaswani. Modified Basis Pursuit Denoising (Modified-BPDN) For Noisy Compressive Sensing With Partially Known Support", Proc. IEEE Intl. Conf. Acous. Speech. Sig. Proc. (ICASSP) (2010).

C. System (Supplemental Information)

One example of the instrument is in "Plant chip for high-throughput phenotyping of *Arabidopsis*," published online and in the Apr. 7, 2014 issue of the journal Lab on a Chip, see Jiang H, Xu Z, Aluru M R, Dong L, Lab Chip 2014 Apr. 7: 14(7): 1281-93, incorporated by reference herein in its entirety.

D. Specific Micro Seed Chip Example

As discussed above, one way to position seeds inside a miniature greenhouse (MGH) as well as facilitate germination and seedling growth is what is called a micro seed chip (MSC). A specific embodiment similar to and that can be used in the system described above will now be described. See also Huawei Jiang, Zhen Xu, Maneesha R Aluru and Liang Dong. "Plant chip for high-throughput phenotyping of *Arabidopsis*", Lab Chip, 2014, 14, 1281. FIGS. 16A-C through 28 correspond to the FIGS. 1-13 in that publication.

The vertical plant chip 13 in this example is developed for high-throughput and large-scale phenotyping of *Arabidopsis thaliana* plants. Multiple seeds can be germinated and grown hydroponically up to four weeks in the chip. The vertical arrangement of the chip makes it convenient to continuously monitor plant-pathogen interactions at different developmental stages, and phenotypic changes in plants at the whole organismal level, including seed germination and root and shoot growth, as well as at the cellular level.

We report below on the development of a vertical and transparent microfluidic chip for high-throughput phenotyping of *Arabidopsis thaliana* plants. Multiple *Arabidopsis* seeds can be germinated and grown hydroponically over more than two weeks in the chip, thus enabling large-scale and quantitative monitoring of plant phenotypes. The vertical arrangement of this microfluidic device not only allows for normal gravitropic growth of the plants but also, more importantly, makes it convenient to continuously monitor phenotypic changes in plants at the whole organismal level, including seed germination and root and shoot growth (hypocotyls, cotyledons, and leaves), as well as at the cellular level. We also developed a hydrodynamic trapping method to automatically place single seeds into seed holding sites of the device and to avoid potential damage to seeds that might occur during manual loading. We demonstrated general utility of this microfluidic device by showing clear visible phenotypes of the immutans mutant (im) of *Arabidopsis*, and we also showed changes occurring during plant-pathogen interactions at different developmental stages. *Arabidopsis* plants grown in the device maintained normal morphological and physiological behavior, and distinct phenotypic variations consistent with a priori data were observed via high-resolution images taken in real time. Moreover, the timeline for different developmental stages for plants grown in this device was highly comparable to growth using a conventional agar plate method. This prototype plant chip technology is expected to lead to the establishment of a powerful experimental and cost-effective framework for high-throughput and precise plant phenotyping.

Introduction

The recent completion of the genome sequencing projects, along with advances in high-throughput technologies (e.g., microarrays, next generation sequencing), have made it possible for a high-throughput "systems approach" to acquire a great wealth of information about the genotype, i.e., the genetic makeup of an organism. [see bibliography of Section D, infra., at D1-7] Much of the existing instrumentation and software have also been built with the key goal of identifying and analyzing various biomolecules (e.g., DNA, RNA, metabolites). But information about the genotype is only useful in so far as it allows us to make predictions about the phenotype, i.e., the observable traits and characteristics of an organism. Phenomics is an emerging area of science that links observations on genotypes with phenotypes. [D8, 9] However, characterization of the complete plant phenome poses a difficult challenge, as even plants with smaller genomes such as *Arabidopsis thaliana* contain tens of thousands of genes. [D10-12]

Previous plant phenotype analyses relied on culturing seeds and growing plants in soil pots and agarose plates using culture facilities (e.g., greenhouse, growth chamber) under controlled environments, and on using imaging technology to measure plant characteristics and phenotypic changes. [D13-19] Multi-well plates have also been utilized for chemical screening of a large number of seedling roots. [D20, 21] However, there are several concerns worth noting. First, screening of plant phenotypes using traditional greenhouses and growth chambers is costly and the number of experiments is limited. Flexibility and accuracy of changing plant growth environments are also relatively low. Second, due to the use of soil pots and agarose plates, a relatively large amount of chemicals and biological species is needed. Third, spatial resolution of morphological measurements for seed, root, and shoot phenotypes is often on the millimeter scale as soil pots and agarose plates are not optically transparent. Real-time observation of cellular behaviors (e.g., cell division, elongation, host-pathogen interactions) is also not easy. As a result, low temporal resolution may lead to missing information about progressive and subtle changes in phenotypes during plant growth. Therefore, while progress has been made in this area, the traditional plant phenotyping approaches suffer from expense, labor, and time involved in large-scale phenotypic analyses (especially under varying environmental conditions), low spatial and temporal resolution, low throughput for obtaining phenotype information, and frequent manual intervention during growth and imaging. [D22-24]

Microfluidic technology provides a powerful and flexible platform to interrogate cellular and multicellular organisms. The general advantages of microfluidics-based bioassays include high throughput and improved data statistic due to parallel processing, reduction of agent consumption, fast reaction, and avoidance of contamination. Prior developments in microfluidic devices have greatly advanced high throughput analyses of model organisms, such as *Drosophila melanogaster* and *Caenorhabditis elegans*. [D25-30] But microfluidic technology is still relatively underdeveloped and underutilized for applications in plant sciences, an area with huge social and economic impact.

Recently, *Arabidopsis* root development and *Camellia* pollen tube growth have been studied using microfluidic devices. [D31-36] A Root Chip was developed for high-throughput plant gene expression analysis, [D32] where *Arabidopsis* seeds germinated and grew initially in conventional pipettes for several days, and then, transferred into the chip for root gene expression studies. More recently, a Root Array was reported, where multiple *Arabidopsis thaliana* seedlings grew in the chip and their roots were imaged using confocal laser scanning microscopy over several days. [D35] Our group also developed a microfluidic device for in-chip seed germination and seedling growth at different growth temperatures over several days, thus expanding the utility of microfluidic technology for manipulating plant environmental conditions. [D33] Although these approaches have advanced the use of microfluidics in plant sciences, phenotypic measurements with these devices were restricted only to plant roots, [D32-36] and quantitative measurements of other organ phenotypes (e.g., seed germination, hypocotyl, cotyledon, leaf growth) were not feasible. Therefore, the existing microfluidic devices are of limited use for characterization of the complete plant phenome.

Here, we report on the development of a novel microfluidic device for high-throughput phenotyping of *Arabidopsis* plants. Unlike the previous microfluidic devices where the plant roots were grown horizontally in microchannels, specimen transfer was sometimes required after a certain period of growth, and phenotypic measurement was allowed only for root systems over a relatively short growth time, the present device consists of a transparent and vertical microfluidic chip where multiple *Arabidopsis* seeds can be germinated and grown vertically in the chip, not only allowing for normal gravitropic growth of the plants but also, more importantly, making it convenient for continuous and non-invasive monitoring of phenotypic changes of different plant organs, including both root and shoot systems, over various plant developmental stages. Also, in the present device, *Arabidopsis* plants can grow over a longer growth period than the existing devices (i.e., more than two weeks vs. several days).

Methods and Experimental Section
Overall Design of Device

FIG. 16A shows a schematic of the present microfluidic plant chip 13. The device allows multiple plants to simultaneously grow in vertical direction in multiple growth regions. Each growth region includes a funnel-shaped seed holding site 123 on the top and a tapered expanding micro channel 125 on the bottom. The seeds 29 are germinated inside the seed holding sites 123. The plant roots grow downward into the tapered channel 125. The main channel 126 above the seed holding sites 123 allows sufficient space for the plant shoots to grow upward (FIGS. 16A and 16B). To accommodate phenotyping of different plant species growing at different stages of interest, the number of the seed holding sites and the structure and geometry of the root and shoot growth regions can be flexibly changed during device design and fabrication. In the device presented here, 26 *Arabidopsis* plants are distributed on two connecting floors. To hold *Arabidopsis* seeds and provide enough room for seed germination, the lower and upper openings of the funnel are designed to be 350 µm and 725 µm wide, respectively. The root and shoot growth regions are designed to be 10 mm and 1.8 mm tall, respectively. All of the channels of the device are 400 µm deep. In the case that the main channel is closed (FIG. 16B), the plants can grow within the device for about eleven days, during which seed germination and emergence and growth of plant root, hypocotyl, cotyledon, and the first two true leaves can be clearly imaged. By opening up the main channel 126 of the device, the plants can grow over more than two weeks and the plant phenotypes through later growth stages can be observed and recorded (FIG. 16C). This transparent device, in conjunction with a conventional microscopic imaging system, can facilitate easy and high-quality observation of plant phenotypes at the whole organismal as well as at the cellular level.

FIG. 16A is a schematic of the plant chip for high-throughput plant phenotyping. FIG. 16B are images of in-chip seed germination and plant growth. Major plant organs and device structures are labelled and highlighted. In this top-closed design, the main channel is closed during the growth of the plants. FIG. 16C shows an image of a top-opened design for plant phenotyping over a longer growth period. The top part of the main channel is cut off. The shoot system of the plants is grown outside of the top-opened device.

Design for Hydrodynamic Trapping of Seeds

Generally, individual *Arabidopsis* seeds are handled by using sterilized tools such as toothpicks or forceps. Due to their small size, it would be difficult to manually pick and load seeds individually into multiple devices for large-scale analyses. The seeds may get contaminated or even destroyed during manual handling. To overcome this issue, we developed a hydrodynamic microfluidic trapping method to automatically load seeds into individual seed holding sites 123 of the chip 13. Each trapping site 123 was patterned like a funnel. The top opening of the funnel was large enough to allow a seed to come in, while the bottom opening was relatively smaller to prevent the seed from falling out of the funnel. Multiple seeds were infused into the main channel 126 by flowing a liquid medium through the inlet of the device (FIG. 16A). A sucking pressure was applied through the outlet by withdrawing the fluid out of the device, forcing the seeds to flow against the lower wall of the main channel 126. As the seed flowed by a funnel 123, the fluid streamlines would carry the seed into the funnel 123. Since each funnel is designed to allow hosting of only one seed, other seeds have to flow over this funnel to the following ones, allowing for a single seed to be trapped. FIG. 16A is a FEA model for simulating fluid dynamics during hydrodynamic trapping of a seed into a funnel-like trapping site.

To better understand the seed trapping mechanism and to study the influences of the seed and device geometries, and the infusion and withdrawal flow rates on the seed trapping, we conducted fluid dynamic simulations for the device by using finite element analysis (FEA) software COMSOL. A model was thus built for the simulation (FIG. 17A). The key structural and geometrical parameters include the widths of the top and bottom openings (Wt and Wb, respectively) and the depth of the funnel (L), the height or width of the main channel (H), the lengths of the semi-major and semi-minor axes of the seed (a and b, respectively), and the ratio of a to b or a/b. Because the present device was designed for phenotyping of *Arabidopsis* plants, based on the possible sizes and shapes of different types of *Arabidopsis* seeds, we set reasonable dimension ranges for the aforementioned parameters as follows: $1 \leq ha/b \leq 2.25$, $0.3\ mm \leq a \leq 0.6\ mm$, $1 \leq H \leq 3\ mm$, $2a<Wt<4a$. $Wb<2b$, and $2a<L<4a$.

All of the FEA simulations were conducted under a rotational equilibrium condition that a seed was assumed to move axially without rotation while moving in the main channel. Through extensive simulational trials, the rotational equilibrium of the seeds was achieved at an angle of about 30 degrees between the seed's semi-major axis and the longitudinal direction of the main channel. The criteria for successful seed trapping were that the volumetric center of the seed should be located above a critical streamline (highlighted by the white lines in FIGS. 17B-H) that starts at the input of the main channel and ends at the upper-right corner of the funnel.

FIGS. 16B-H have the following attributes. FIG. 16B: Distributions of fluid velocity when the seed is flowing at different distances from the lower sidewall of the main channel in the vertical direction. From left to right, h=0.3, 0.6, 0.75, and 0.9 mm, respectively. FIG. 16C: Distributions of fluid velocity when the seed is located at different distances from the upper left corner of the funnel in the longitudinal or horizontal direction. From left to right, x=1.5, 1, 0.5, and 0.1 mm, respectively. FIG. 16D: Distributions of fluid velocity under different pressure drops along the main channel over a single trapping site in the longitudinal direction. From left to right, AAP=0.5, 1, 1.5, and 2 Pa, respectively. FIG. 16E: Influence of the shape of a seed on the distribution of fluid velocity. From left to right, a/b=1, 1.67, 2, and 2.25, respectively, while a is fixed at 0.2 mm. FIG. 16F: Influence of the size of a seed on the distribution of fluid velocity. From left to right, a=0.3, 0.4, 0.5, and 0.6 mm, respectively, while a/b is fixed at 2. FIG. 16G: Influence of the width of the top opening of the funnel on the distribution of fluid velocity. From left to right, Wt=0.6, 0.8, 1 and 1.2 mm, respectively, while Wb is fixed at 0.3 mm. FIG. 16H: Influence of the height or width of the main channel on the distribution of fluid velocity. From left to right, H=1, 1.5, 2, and 3 mm, respectively. In FIGS. 16A-H, the color scale represents the fluid velocity, where red indicates high and blue indicates low. The white lines added to the distribution profiles of fluid velocity represent the critical streamlines.

We first studied how the pressure drop AP over a trapping site along the main channel impacted the seed trapping. FIG. 17B shows that when the volumetric center of the seed was located above one-third the height or width of the main channel from the lower horizontal sidewall of the main channel, the seed would pass by rather than flowing into the funnel under a low $\Delta P=0.5$ Pa. To simplify, all of the seeds in the following simulations were set to flow against the lower sidewall of the main channel. FIG. 17C indicates that regardless of the lateral distance x between the seed and the funnel, the seed could be trapped into the funnel as long as the seed was flowing against the sidewall under $\Delta P=0.5$ Pa. But as AP gradually increased to 2 Pa (FIG. 17D), the critical streamline moved closer to the sidewall and overlapped the volumetric center of the seed (see the first panel from the right in FIG. 17D). This indicates that by applying a higher AP, the seed would pass by the funnel.

Subsequently, the influence of the shape and size of a seed on the seed trapping was studied. The simulated results show that as the value of a/b increased from 1 to 2.25 while keeping $a=400\ \mu m$ (FIG. 17E) or as the seed was scaled up in all dimensions while keeping a/b=2 (FIG. 17F), the seed would be trapped under a low $\Delta P=0.5$ Pa as long as the volumetric center of the seed was located below the corresponding critical streamline.

In addition, the influence of the structure of the main channel and the funnel on the seed trapping was investigated. The simulated result shows that increasing the width of the top opening of the funnel caused the critical streamline to elevate, which, in turn, would make it easier to trap the seed (FIG. 17G). On the other hand, as the width of the main channel increased from 1 to 3 mm, the seed flowing along against the lower sidewall of the main channel would still be trapped (FIG. 17H).

It is worthwhile to point out that since dimensional variations among different types of *Arabidopsis* seeds are actually minor (at the size scale of several hundreds of micrometers), it should be relatively easy to tune the key structural parameters of the device to adapt to different seeds, without the need of establishing a new model for simulations.

Experimentally, in order for the seed to flow in the lower part of the main channel, a pulling pressure was applied at the outlet of the device (FIGS. 16A and 17A). Thus, two syringe pumps were simultaneously used during seed trapping, one for infusion and the other for withdrawal of fluid. We experimentally studied how the infusion/withdrawal flow rates affected the trapping rate of *Arabidopsis* seeds. Here, the trapping rate refers to the success rate of trapping one or two seeds in a funnel. It is noted that trapping two seeds in a single funnel was possible as the sizes and shapes of the seeds (of even the same type) were not uniform. FIG. 18A demonstrates that (i) as the withdrawal flow rate increased from 0 to 20 µL s−1, the trapping rate increased from 4.6±2.9% to 97±2.2%; (ii) the lower the infusion flow rate, the easier the seed trapping, and thus, the higher the trapping rate, which followed the trend seen in FIG. 17H; and (iii) the trapping rate decreased gradually and then relatively abruptly with increasing the infusion flow rate from 5 to 75 µL s−1.

FIG. 18B shows the experimental results of how the width of the main channel affected the trapping rate. As Wt increased from 1.4 to 3 mm, the seeds flowing in the lower part of the main channel relatively reduced in quantity, and thus, the trapping rate was observed to decrease from 97±2.2% to 16±6.5% at the infusion flow rate of 20 µL s−1 and the withdrawal flow rate of −20 µL s−1. It should be noted that by increasing the withdrawal flow rate, the trapping rate of the device having a wider channel could be increased to be nearly 100% as demonstrated in FIG. 18B.

FIGS. 18A and B have the following attributes. FIG. 18A: Experimental result of the seed trapping rate as a function of infusion flow rate for different withdrawal flow rates. *Arabidopsis* seeds used here has a/b=1.88±0.2. FIG. 18B: Experimental result of the trapping rate as a function of the width of the main channel at different infusion and withdrawal flow rates. The trapping sites used here are shown in FIG. 17B. Each measurement is the mean±standard deviation obtained from 10 measurements Device Fabrication The microfluidic devices were fabricated using a conventional soft lithography technique. [D37] Briefly, to make a master mould for the microchannels, a silicon wafer was first patterned with SU-8 photoresist (Microchem, Mass., USA). Then, a high resolution transparency film (10 160 dpi, Fineline Imaging, CO, USA) was used as a photo mask in photolithography. A prepolymer mixture of polydimethylsiloxane or PDMS (Sylgard 184, Dow Corning, Mich., USA) and its curing agent with a weight ratio of 10:1 was poured onto the master mould and then thermally cured on a hotplate at 90° C. for 1 hour. Subsequently, the hardened PDMS polymer was pealed from the mould and bonded to a microscope glass slide (75 mm×50 mm×0.9 mm) by using oxygen plasma treatment. Lastly, the inlet and outlet ports of the device were manually punched with a mechanical puncher.

It should be pointed out that the formation of the PDMS based structures on a glass slide is not expected to modify *Arabidopsis* growth patterns. PDMS-glass microfluidic devices have been widely used in characterization of both cellular and multicellular organisms. [D28, 38, 39] Moreover, *Arabidopsis* plants are routinely grown in glass flasks containing hydroponic growth media for biochemical and physiological studies. As discussed in Table 1 (below), our results show that the growth stages for *Arabidopsis* plants grown in the fabricated devices were comparable to those grown in conventional Petri dish. This further demonstrates that materials used for the fabrication of the devices had little or even no influence on the growth patterns of *Arabidopsis* plants.

Culture Media

Three different liquid culture media were prepared and used, including tap water, Murashige and Skoog (MS) medium, and standard medium. [D40] All of the chemicals used were of analytical reagent grade. Deionized water was used throughout to prepare the three nutrient media. MS salts were purchased from Sigma-Aldrich, Mo., USA. Culture media were sterilized in an autoclave at 15 psi at 121° C. for 30 min and stored at 4° C. in a refrigerator. They were loaded into the device using a 3 mL syringe (Becton Dickinson, N.J., USA) with a microbore tubing (Cole-Parmer, Ill., USA) before the seeds were transferred into the device.

Preparation of *Arabidopsis* Seeds

Wild-type (WT) *Arabidopsis thaliana* ecotype Columbia, the immutans mutant of *Arabidopsis*, and transgenic *Arabidopsis* seeds containing the IM promoter green fluorescent protein (GFP) reporter fusion construct were used in this study. GFP activity assays were performed using confocal laser scanning microscopy with seeds and seedlings grown within the device. The seeds were surface-sterilized by soaking in 70% ethanol (v/v) for 1 min, followed by 50% (v/v) Clorox and 0.02% (v/v) Triton for 15 min. They were then washed three times with autoclaved deionized (DI) water.

To trap and hold *Arabidopsis* seeds in the vertical device, the lower opening size of the seed holding site must be less than the small diameter of the oval shaped seed. But if the lower opening was made too small, the root growth of the seeds would be influenced due to the limited space. Therefore, *Arabidopsis* seeds were soaked in a Petri dish containing autoclaved DI water for 3-5 h and allowed to expand in size slightly prior to loading.

Trapping of *Arabidopsis* Seeds

Before seed trapping, all channels in the device were filled with one particular culture medium of interest by using a syringe via a tubing connection. Care was taken to avoid introducing air bubbles into the channels. Subsequently, the soaked seeds were sucked manually from the soaking Petri dish up into a 500 µm inner diameter microbore tubing using a syringe. The tubing was then connected to the inlet port of the device. After that, a syringe pump (KDS200, KDScientific, Mass., USA) was used to inject the seeds directly from the tubing into the device through the inlet port at an infusion flow rate of 20 µL s−1. The other syringe pump (same model) applied a sucking pressure through the outlet of the device at a withdrawal flow rate of −20 µL s−1, forcing the seeds to flow along the lower sidewall of the channel. It took 3-4 s to complete the seed trapping process.

*Arabidopsis* Plant Growth Conditions

After the seeds were trapped in the seed holding sites, the device was stored at 4° C. in a refrigerator for 40-48 h to stratify the seeds. Subsequently, the device was placed vertically under a plant growth light source (fluorescent daylight). The light intensity was set to ~100 µE m−2 s−1, and plants were grown at room temperature (21-22° C.). The environmental relative humidity was ~40%. For the top-closed device (FIGS. 16A and 16B), growth media were changed in the device on a daily basis using a syringe pump. In the case that the main channel was opened, the fluid level in the device was controlled by slowly flowing growth media (2-3 µL h−1) into the device using a syringe pump through the port where sucking force was applied during the seed trapping process (see FIG. 16B). The seeds germinated and the plants grew in the device, and their growth was monitored after exposure to light (or starting from the completion of stratification).

A microscope (MZ 205FA, Leica, Germany) with a video camera (QICAM, QImaging, Canada) was used to image plants growing in the device. The system was used to collect phenotypic data of interest, including seed phenotype (e.g., germination), root phenotype (e.g., length, diameter), shoot phenotype (e.g., hypocotyl, cotyledon and leaf emergence and dimensions), and cell phenotype (e.g., cell division and elongation). All data points reflect the average from five replicates performed on five chips, with each chip having 20-26 plants on a device. Error bars represent standard deviations.

Results and Discussion

Hydrodynamic Seed Trapping

FIGS. 19A-C show the results of the hydrodynamic seed trapping method (also see video clip in electronic supplementary information (ESI) to Lab Chip, 2014, 14, 1281-1293 at DOI: 10.1039/c31c51326b. Almost all of the seed holding sites in the device held seeds. 70-80% of these sites had a single seed while the rest of the sites trapped more than one seed. This is because the *Arabidopsis* seeds were not uniform in size and multiple smaller seeds could be trapped into one holding site. We observed that after a seed fell into a trapping site, other seeds were not trapped. The percentage of the trapped seeds with respect to the total input seeds was 30-40%. The untrapped seeds were flowed out of the device.

Specifically, FIG. 19A shows hydrodynamic trapping of *Arabidopsis* seeds. FIG. 19B shows the microfluidic plant chip after seed trapping process. FIG. 19C shows a magnified image showing individual seeds trapped in seed holding sites.

Seed Germination and Plant Growth

As a first step to optimize *Arabidopsis* growth within the device, we tested three different hydroponic media (tap water, MS (Murashige and Skoog) medium and standard medium) previously used in conventional tissue culture methods. FIGS. 20A-C show time-lapse images for the development of *Arabidopsis* plants inside the devices containing the three different growth media. Plant growth and development, including root and shoot systems, were continuously monitored up to 11 days, and images were taken at regular intervals while the plants were growing.

Seed germination and growth of WT *Arabidopsis thaliana* plants in the vertical microfluidic device in shown with MS medium (FIG. 20A), standard medium (FIG. 20B), and tap water (FIG. 20C).

TABLE 1

Comparison of growth stages for WT Arabidapsis plants growing in a microfluidic device and Petri dish inside the device. Plants grown in all three media appeared to maintain all of the morphological traits of plants grown in potting soil and on a Petri plate.

| Growth stage | Microfluidic device (days) | | | Plate (days) Agar + MS D45 |
|---|---|---|---|---|
| | Tap water | MS | Standard | |
| Seed coat breakage | 0.8 ± 0.2 | 1.2 ± 0.2 | 1.0 ± 0.2 | ND |
| Radicle emergence | 1.2 ± 0.2 | 1.7 ± 0.3 | 1.2 ± 0.2 | 1.3 ± 0.4 |
| Length of primary root (0.6 mm) | 2.2 ± 0.2 | 2.0 ± 0.2 | 2.2 ± 0.3 | ND |
| Cotyledon & hypocotyl emergence | 2.5 ± 0.2 | 2.2 ± 0.1 | 2.0 ± 0.2 | 2.5 ± 0.6 |
| Cotyledons fully opened | 3.0 ± 0.2 | 3.0 ± 0.1 | 3.0 ± 0.2 | 3.0 ± 0.5 |
| 2 rosette leaves | 9.0 ± 0.3 | 8.0 ± 0.2 | 8.0 ± 0.3 | 7.3 ± 0.5 | a Note:
all data exclude days of stratification.

*Arabidopsis* seeds generally follow a two-step germination process with rupture of the seed coat in 20-24 h and the emergence of the white radicle following endosperm rupture in 30-33 h. [D41]. As shown in FIGS. 20A-C, in-chip germination of *Arabidopsis* seeds was similarly comparable to the previously reported results with observation of a radicle after around 30 minutes light in all growth media. It should be noted that due to different orientation of the seeds in the holding sites, the radicles of many seeds were not oriented initially downward. But as the roots grew longer, they tended to grow along a side wall of the holding sites, and then, entered downward into the tapered growth region towards the bottom of the device. Quantitative analysis of root length as a function of growth time (FIG. 21A), where root length was measured as the distance from the root tip to the base of the hypocotyl, shows that the roots grew rapidly up to 5 days, but slowly thereafter. Furthermore, in agreement with previously reported literature, [D41-45] the roots growing in tap water were observed to be longer and thinner with sparser root hairs while those growing in MS media and standard media were shorter and wider with a greater number of root hairs. As expected, the green cotyledons were observed to grow up towards the light and in opposite direction to the roots (FIGS. 20A-C). The emergence and growth of the hypocotyl and cotyledon of *Arabidopsis* plants growing within the device could be conveniently imaged and quantitatively analyzed over 11 days without manual intervention. The growth of hypocotyl was similar for all plants in different growth media (FIG. 21B). However, the growth and size of the cotyledons were significantly influenced, with MS medium showing the greatest increase in the surface area (FIG. 21C). The time-frame for emergence of cotyledons was similar in all media with the two cotyledons emerging approximately 52-54 h after exposure to light, following which they grew rapidly for 11 days of plant growth.

In FIGS. 21A-C, major phenotypic parameters of WT *Arabidopsis thaliana* plants as a function of growth time, including root length (FIG. 21A), hypocotyl length (FIG. 21B), and cotyledon surface area (FIG. 21C). The data were obtained by using Matlab based on the images taken at different time points.

To assess whether WT *Arabidopsis* growth and development within the microfluidic device were similar to a prior data, we compared our results with the plants germinated and grown on conventional tissue culture plates. [D46] Table 1 shows that the timeline for many of the plant growth stages was highly comparable between the conventional plate method and the newly developed device. However, slight variations between these two methods were also observed. For example, the appearance of 2 rosette leaves is somewhat delayed (in hours) when compared to the Petri plate method. It should be noted that a Petri plate-based method generally uses gelling agar to prevent seeds from rolling, while plants in our device grew in hydroponic media and the seeds were held by microstructures. Thus, these discrepancies may be caused by differences in geometric structure of growth chambers (channels vs. plates) or the surrounding physical environment of seeds (liquid vs. agar gel). These discrepancies are negligibly small and would not interfere with high-throughput plant phenotyping as long as phenotypic comparisons between different genotypes and plant organs can be simultaneously observed.

Phenotyping of *Arabidopsis* Mutants

We used a well-characterized carotenoid-deficient mutant, the immutans (im) mutant of *Arabidopsis*, [D47, 48] as an example to demonstrate general utility of the present device for phenotyping *Arabidopsis* plants, at the whole organismal as well as at the cellular level. The immutans mutant of *Arabidopsis* has green-white leaves due to a mutation in the nuclear recessive gene, IMMUTANS (IM). The im seeds have been previously shown to germinate similar to WT *Arabidopsis* under various light conditions. Our results show that im seeds germinate and grow under normal light conditions also within the device (FIG. 22) (a time course study of growth and development of WT *Arabidopsis* and immutans plants growing in a standard medium in the vertical microfluidic device). However, we further show that seed germination and radicle protrusion occur much earlier (~12 h) in im when compared to WT *Arabidopsis* (~20 h). Although the exact reason for this phenomenon is not known, it is clear that the new device enables more in-depth exploration and quantitation of the seed germination process in a real-time manner.

Depending on the light intensity, germinated seedlings of im give rise to green, green-white and/or white cotyledons and leaves. An increase in light intensity increases white sector formation whereas low light conditions result in all-green plants. Consistent with previous reports, the cotyledons of im growing in-chip under normal light conditions are white and/or green with the green being somewhat lighter than WT. Seedlings with white cotyledons do not give rise to true leaves and are not viable after 11 days of growth in the hydroponic medium, whereas green colored seedlings grow true leaves after ~194 h of growth (FIG. 22). Under our growth conditions, immutans root and hypocotyl lengths are somewhat similar to WT (FIGS. 23A and B). But the growth of the cotyledons slow down significantly after ~8 days of growth (FIG. 23C). This is in agreement with the slower growth phenotype of im plants versus WT *Arabidopsis*.

FIGS. 23 A-C are major phenotypic parameters of WT *Arabidopsis* and immutans mutant as a function of growth time, including (a) root length, (b) hypocotyl length, and (c) cotyledon surface area, respectively.

To obtain a more detailed cellular description of the *Arabidopsis* im phenotype, we applied confocal laser scanning microscopy (CLSM) and fluorescence stereomicroscopy (LeicaM205FA), and performed in vivo im gene expression analyses using transgenic IM-GFP seeds/plants. The IM promoter3-glucuronidase (GUS) activity assays have previously shown that IM is expressed in all shoot and root tissues throughout the development of Arabidopsis plants. [D48] Similarly, in this study, we show an IM promoter-GFP activity in 1 day, 5 day and 7 day old seedlings, with green fluorescence observed in all tissues including root, hypocotyl, and cotyledons (FIGS. 24A-D and 25A-E). The 5 and 7 day old low resolution images were obtained with the fluorescence stereomicroscope equipped with a GFP filter set to image whole seedlings. This expression pattern was also maintained in developing leaves and roots, with increased expression observed in the root tips, as seen in the images in FIGS. 25A-E. Moreover, im expression was found to be restricted to the chloroplasts within individual cells in green tissues (FIG. 25E), which is consistent with the function of IM in plants. However, our results suggest that im is also expressed very early in the seed germination process. This is illustrated by the presence of green fluorescence first in regions around the embryo, even prior to seed coat breakage and radicle protrusion. Subsequently, the GFP fluorescence extends into the embryo and then into the protruding radicle as the seed germinates (FIG. 26A-C). These results could not be observed previously with GUS activity assays, perhaps due to the fact that the GFP reporter, unlike the GUS reporter, allows nondestructive monitoring of cellular and sub-cellular activities without the need for sample preparation or the uptake of exogenous substrate. No GFP fluorescence was observed in non-transgenic WT control seeds and seedlings (data not shown).

FIGS. 24A-D are growth of IM GFP plants in the vertical microfluidic device. Optical images (a, c) and fluorescence images (b, d) of 5 day and 7 day old seedlings, respectively.

FIGS. 25A-E are confocal laser scanning microscopy images for IM GFP seedlings growing in the device: (a) 1 day old seedlings at a magnification of 10×: (b) 5 day old leaves at 20×; (c) 5 day old root at 10×; (d) 5 day old root tip at 40×; and (e) 5 day old cotyledons at 80×, respectively.

FIGS. 16A-C are a time course study of the seed germination process of IM GFP seeds growing in the vertical device: (a) 0 h, (b) 12 h. and (c) 18 h, after 2 day stratification respectively.

Plant-Pathogen Interactions

Figure 27A:
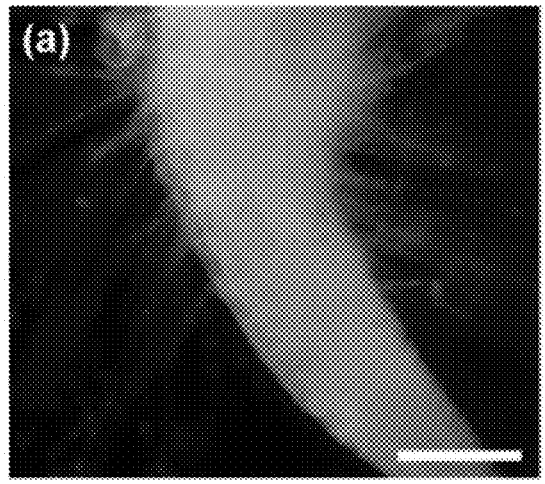
Figure 27B:
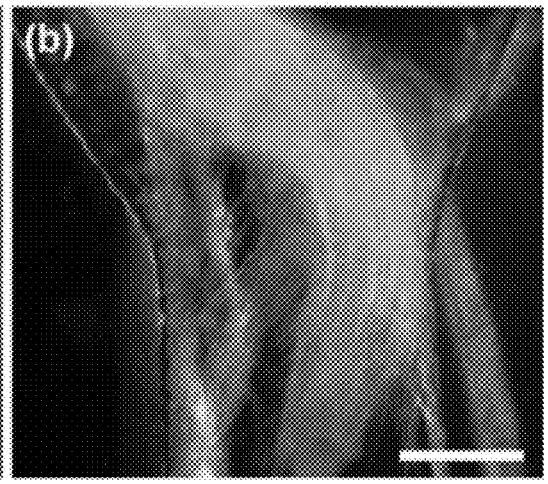

As another example of the utility of the present device for plant phenotyping, we show results from a study of plant-pathogen interactions. Specifically, we demonstrate early interactions of Phytophthora sojac zoospores with wild-type Arabidopsis plants on the vertical microfluidic device. Fungal and oomycete pathogens such as P. sojae cause many destructive diseases of plants and genetic approaches pose difficulty for observing early phenotypic interactions between pathogens and plant roots and shoots. [D49, 50] P. sojae zoospores were flowed into the vertical device with tap water at 24 h after the Arabidopsis seeds were trapped into the seed holding sites. The motile zoospores swam randomly until the root radicles emerged. High resolution images show that the zoospores accumulated down at the root tip and root hairs 5-10 h after their adhesion to the device (FIG. 27A), and then, they started invading the root and the shoot systems. At ~50 h, multiple dark brown spots were observed on the root, which are the symptoms of apoptosis and cell death (FIG. 27B). Several dark brown spots were also observed on the emerging cotyledons and hypocotyl at later stages of infection.

Figure 27C:
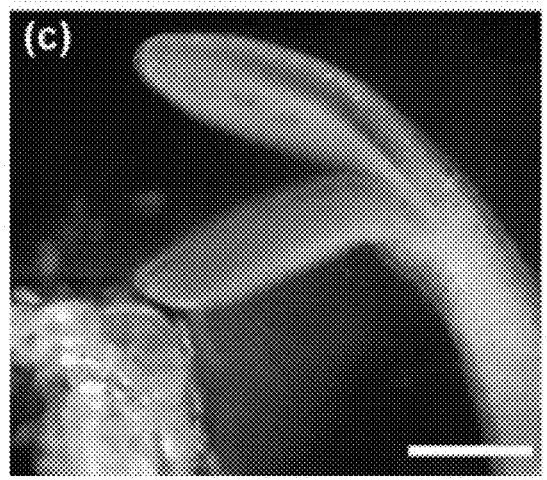
Figure 27D:
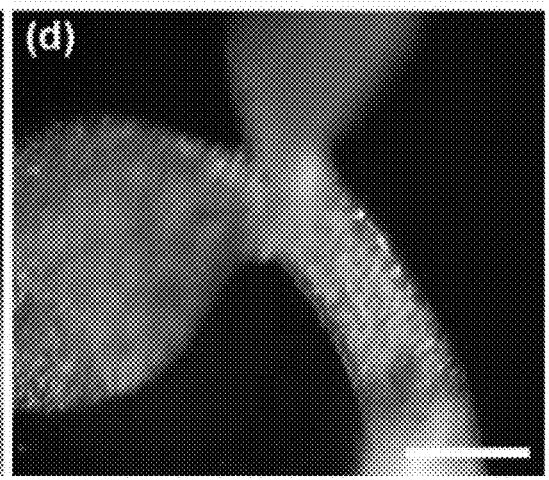

These spots were observed all the way toward the cotyledon, particularly at the intersection between the hypocotyl and root, indicating severe invasion and growth of zoospores inside these organs (FIGS. 27C and D).

FIGS. 27A-D are (a) formation of clusters of P. sojae zoospores on the root and root hairs of Arabidopsis plant, observed at 31 h; and dark brown spots on the root (b), cotyledon (c), and hypocotyl (d), observed at 50 h, 124 h, and 192 h, respectively. Scale bars are 100 µm.

Top-Opened Device for Phenotyping Arabidopsis Plants Over a Longer Period of Growth In general, growth and development of WT Arabidopsis did not appear to be affected during its 11 day growth in the microfluidic device; however, the device presented above used a closed-top design, which in turn limited the space of the channels above the seed holding site for shoot growth. Hence, the shoot phenotype could be monitored only through the stage of emergence of two rosette leaves on the plants. To accommodate developmental stages beyond the 2-leaf stage, we further created a top-open device in which the main channel above the seed holding site is open to air. This allowed for observing and recording cotyledon and leaf phenotypes over a longer period of growth. Specifically, after Arabidopsis seeds were trapped, the top part of the channel above the seed holding sites was manually cut off by a razor blade. The level of growth medium in the device was adjusted by slowly flowing a growth medium into the device as described earlier. FIG. 28 shows Arabidopsis plants grown for a longer period of 15 days in the top-opened device in a standard medium. The standard medium allowed similar and measurable growth of both shoot and root regions when compared to the other two media. Similar to observations made with the closed device, we observed radicle emergence at ~32 h. and the hypocotyl and cotyledon emergence at ~54 h. The two early rosette leaves were observed at ~192 h, and then, more leaves emerged in the following days. The leaves were growing upward outside the channel while the roots were still elongating inside the channel. At the end of 15 days, we observed 5 rosette leaves. This is consistent with previous reports of plants growing on MS agar plates where 5 rosette leaves developed at 14.7±1.8 days (excluding 3 days of stratification). [D46] Thus, by simply opening up the main channel above the seed holding sites, the issue of limited growth space inside the device could be largely eliminated, which would make it possible to observe and record plant phenotypes through later growth stages, thus further expanding the utility of the device for plant phenotyping.

FIG. 28 are images of growth of a WT Arabidopsis thaliana plant over 15 days in the top-open vertical microfluidic device. The inset in the bottom-left corner shows cotyledons and leaves growing out of the vertical device.

CONCLUSION

Systematic characterization of plant phenotypes remains a major challenge due to their large genome sizes and tens of thousands of genes which respond differentially to various external and internal stimuli. Because of this inherent complexity, analyzing plant phenotypes on a large and multi-scale level with sufficient throughput, resolution and precision has been difficult and expensive. Previous work has addressed this challenge to some extent, but these studies were mainly focused on phenotyping of roots. [D32-36] In this paper, we demonstrate the development of a new microfluidic device that is easy and cost-effective to use, and also enables seamless monitoring of both root and shoot phenotypes. We have provided a few examples and applications of the prototype device in this study. However, the device design can be flexibly changed to further enhance its application in the plant phenomics area. For example, with a top-open device (FIG. 28), plants can be grown over longer periods of time, allowing for different and multiple types of *Arabidopsis* genotypes to be simultaneously characterized at the physiological, biochemical and molecular level, and at various stages of growth. In fact, the vertical device was able to sustain plant growth for over 4 weeks (data not shown).

Further research and development remain to be done to realize an ultimate screening platform for high-throughput plant phenotyping. Other microfluidic and microsystem techniques can be developed and integrated into this present microfluidic device. Through microfluidic tuning, flexible control over chemical concentration and composition in each growth channel can provide a large number of different nutrimental, chemical and biological environments for the plants growing in the microfluidic device. Different means of generating concentration gradients have been demonstrated, [D51-54] such as using universal concentration generator and on-chip dilution approach. Also, to control plant growth temperature, a simple thin-film resistive heater and temperature sensor can be integrated on the plant chip. These types of modifications will further expand the utility of the present device as multiple plants can be analyzed under different environmental conditions in a single experiment. Furthermore, by employing an automated robotic imaging system, it is possible to take a large number of images for different plant growth regions in the devices. Therefore, we believe that the present vertical microfluidic plant chip technology can contribute towards establishing a powerful experimental framework for high-throughput and precise plant phenotyping, and it will create a paradigm-shift in the plant phenomics area.

NOTES AND REFERENCES FOR SECTION D

D1 T. Thorsen, S. J. Maerkl and S. R. Quake, Science. 2002, 298, 580-584.
D2 J. Melin and S. R. Quake, Annu. Rev. Biophys. Biomol. Struct., 2007, 36, 213-231.
D3 S. R. Quake and A. Scherer, Science, 2000, 290, 1536-1540.
D4 M. A. Unger, H. P. Chou, T. Thorsen, A. Scherer and S. R. Quake, Science, 2000, 288, 113-116.
D5 C. Bolle, A. Schneider and D. Leister, Curr. Genomics, 2011, 12, 1-14.
D6 T. Kuromori. T. Wada, A. Kamiya, M. Yuguchi, T. Yokouchi, Y. Imura, H. Takabe, T. Sakurai, K. Akiyama, T. Hirayama, K. Okada and K. Shinozaki, Plant J., 2006, 47, 640-651.
D7 T. Kuromori, S. Takahashi, Y. Kondou, K. Shonozaki and M. Matsui, Plant Cell Physiol., 2009, 50, 1215-1231.
D8 D. Houle, D. R. Govindaraju and S. Omholt, Nat. Rev. Genet., 2010, 11, 855-866.
D9 R. T. Furbank and M. Tester, Trends Plant Sci., 2011, 16, 635-644.
D10 P. K. Gupta, S. Rustgi and R. R. Mir, Heredity, 2008, 101, 5-18.
D11 J. D. Hoheise, Nat. Rev. Genet., 2006, 7, 200-210.
D12 P. Liu, N. Koizuka, T. M. Homrichhausen, J. R. Hewitt, R. C. Martin and H. Nonogaki, Plant J., 2005, 41, 936-944.
D13 D. C. Boyes, A. M. Zayed, R. Ascenzi, A. J. Mac-Caskill, N. E. Hoffman, K. R. Davis and J. Gorlach, Plant Cell, 2001, 13, 1499-1510.
D14 A. Sessions, E. Burke. G. Presting, G. Aux, J. McElver, D. Patton, B. Dietrich, P. Ho. J. Bacwaden, C. Ko, J. D. Clarke, D. Cotton, D. Bullis, J. Snell, T. Miguel, D. Hutchison, B. Kimmerly, T. Mitzel, F. Katagiri, J. Glazebrook, M. Law and S. A. Goff. Plant Cell, 2002, 14, 2985-2994.
D15 M. R. Poncl, P. Robles and J. L. Micol, Mol. Gen. Genet., 1999, 261, 408-415.
D16 J. M. Alonso, A. N. Stepanova, T. J. Leisse, C. J. Kim, H. M. Chen, P. Shinn, D. K. Stevenson, J. Zimmerman, P. Barajas, R. Cheuk, C. Gadrinab. C. Heller, A. Jeske, E. Koesema, C. C. Meyers, H. Parker, L. Prednis, Y. Ansari, N. Choy, H. Deen, M. Geralt, N. Hazari, E. Hom, M. Kames, C. Mulholland, R. Ndubaku, 1. Schmidt, P. Guzman, L. Aguilar-Henonin, M. Schmid, D. Weigel, D. E. Carter, T. Marchand, E. Risseeuw, D. Brogden, A. Zeko. W. L. Crosby. C. C. Berry and J. R. Ecker, Science, 2003, 301, 653-657.
D17 Q. Dong. S. D. Schlueter and V. Brendel, Nucleic Acids Res., 2004, 32(suppl. 1). D354-D359.
D18 R. Subramanian, E. P. Spalding and N. J. Ferrier, Mach. Vision Appl., 2013, 24, 619-636.
D19 P. Zimmermann, M. Hirsch-Hoffmann, L. Hennig and W. Gruissem. Plant Physiol., 2004, 136, 2621-2632.
D20 J. K. C. Rose, S. Bashir, J. J. Giovannoni. M. M. Jahn and R. S. Saravanan. Plant J., 2004, 39, 715-733.
D21 M. M. Bushey and J. W. Jorgenson, Anal. Chem., 1990, 62, 161-167.
D22 V. Zabrouskov, L. Giacomelli, K. J. van Wijk and F. W. McLafferty, Mol. Cell. Proteomics, 2003, 2, 1253-60.
D23 L. W. Sumner. P. Mendes and R. A. Dixon. Phytochemistry, 2003, 62, 817-36.
D24 A. S. Iyer-Pascuzzi, O. Symonova, Y. Mileyko, Y. Hao, H. Belcher, J. Harer, J. S. Weitz and P. N. Benfey, Plant Physiol., 2010, 152, 1148-1157.
D25 E. M. Lucchetta. J. H. Lee, L. A. Fu. N. H. Patel and R. F. Ismagilov. Nature, 2005, 434, 1134-1138.
D26 G. M. Whitesides, Nature, 2006, 442, 368-373.
D27 N. Chronis, M. Zimmer and C. I. Bargmann, Nat. Methods, 2007, 4, 727-731.
D28 K. Chung, M. M. Crane and H. Lu. Nat. Methods, 2008, 5, 637-643.
D29 P. Liu. R. J. Martin and L. Dong, Lab Chip, 2013, 13, 650-661.
D30 P. Liu, D. Mao, R. J. Martin and L. Dong, Lab Chip, 2012, 12, 3458-3466.
D31 c. G. Agudelo, A. S. Nezhad, M. Ghanbari, M. Naghavi, M. Packirisamy and A. Geitmann, Plant J., 2013, 73, 1057-1068.
D32 G. Grossmann, W. Guo, D. W. Ehrhardt, W. B. Frommer, R. V. Sit, S. R. Quake and M. Meier, Plant Cell, 2011, 23, 4234-4240.
D33 H. Jiang, Y. Jiao. M. R. Maneesha and L. Dong, J. Nanosci. Nanotechnol., 2012, 12, 6333-6339.
D34 M. Meier, E. M. Lucchetta and R. F. Ismagilov, Lab Chip, 2010, 10, 2147-2153.
D35 W. Busch, T. M. Brad, M. Bradley, D. L. Mace. R. W. Twigg, J. Jung. L Pruteanu-Malinici, S. J. Kennedy, G. K. Fricke, R. L. Clark, U. Ohler and P. N. Benfey, Nat. Methods, 2012, 9, 1101-1106.
D36 A. Parashar and S. Pandey, Appl. Phys. Lett. 2011, 98, 263703.
D37 D. B. Weibel, W. R. DiLuzio and G. M. Whitesides, Nat. Rev. Microbiol., 2007, 5, 209-218.
D38 A. S. Reyhani, J. Kaplinsky, E. Burgin, M. Novakova, A. J. deMello, R. H. Templer, P. Parker, M. A. Neil. O Ces, P. French. K. R. Willison and D. Klug, Lab Chip, 2011, 11, 1256-1261.

D39 D. D. Carlo, L. Y. Wu and L. P. Lee, Lab Chip, 2006, 6, 1445-1449.

D40 P. Berthomieu, G. Conéjéro, A. Nublat. W. J. Brackenbury. C. Lambert, C. Savio. N. Uozumi, S. Oiki, K. Yamada, F. Cellier. F. Gosti, T. Simonneau, P. A. Essah, M. Tester, A. A. Very, H. Sentenac and F. Casse, EMBO J., 2003, 22, 2004-2014.

D41 P. P. Liu, N. Koizuka, T. M. Homrichhausen, J. R. Hewitt, R. C. Martin and H. Nonogaki, Plant J., 2005, 41, 936-944.

D42 T. Ingestad and G. I. Agren, Ecol. Appl., 1991, 1, 168-174.

D43 H. Zhang, A. J. Jennings and B. G. Forde, J. Exp. Bot., 2000, 51, 51-59.

D44 H. Zhang and B. G. Forde, Science, 1998, 279, 407-409.

D45 H. Zhang, A. Jennings. P. W. Barlow and B. G. Forde, Proc. Natl. Acad. Sci. U.S.A, 1999, 96, 6529-6534.

D46 D. C. Boyes, A. M. Zayed and R. Ascenzi, Plant Cell, 2001, 13, 1499-1510.

D47 C. M. Wetzel, C. Z. Jiang, L. J. Meehan, D. F. Voytas and S. R. Rodermel, Plant J., 1994, 6, 161-175.

D48 M. Aluru, H. Bae, D. Wu and S. Rodermel, Plant Physiol., 2001, 127, 67-77.

D49 W. Grunewald, G. van Noorden, G. van Isterdael, T. Beeckman, G. Gheysen and U. Mathesius, Plant Cell, 2009, 21, 2553-2562.

D50 N. Wuyts, G. Lognay, R. Swennen and D. De Waele, J. Exp. Biol., 2006, 57, 2825-2835.

D51 C. Hao and M. J. Christian, Appl. Phys. Lett., 2004, 84, 2193-2195.

D52 N. L. Jeon, S. K. W. Dertinger, D. T. Chiu, I. S. Choi, A. D. Stroock and G. M. Whitesides, Langmuir, 2000, 16, 8311-8316.

D53 x. Jiang, Q. Xu, S. K. W Dertinger. A. D. Stroock, T. M. Fuand G. M. Whitesides, Anal. Chem., 2005, 77, 2338-2347.

D54 D. Irimia, D. D. A. Geba and M. Toner, Anal. Chem., 2006, 78, 3472-3477.

E. Specific Micro Seed Chip Example (Supplemental Information)

Additional information about a micro seed chip (MSC) the same or similar to that described above is as follows. See also H. Jiang. Z. Xu, M. R. Aluru and L. Dong, "A MICROFLUIDIC WHOLE-PLANT PHENOTYPING DEVICE", Solid-State Sensors, Actuators and Microsystems (Transducers & Eurosensors XXVII) 2013 Transducers & Eurosensors XXVII: The 17$^{th}$ International Conference on, Barcelona. SPAIN, 16-20 Jun. 2013, pages 1539-1542, which is incorporated by reference herein in its entirety. FIGS. 29 to 33A-C correspond to FIG. 1-5 in that publication.

The paper reports on development of a microfluidic device for facilitating phenotypic assays of plant *Arabidopsis thaliana* at the whole organismal level. The device allows for convenient and high-quality observation of various plant phenotypes, including seed germination, root growth, and shoot growth.

1. INTRODUCTION

Plant science is an area that has huge social and economic impact but under-researched in the field of microsystems. Particularly, altered plant phenotypes are central to discovery of gene functions and molecular relationships among genes, thus illustrating the close relationship between the genotype and the phenotype of a plant. However, systematic analysis of genotype-to-phenotype relationship relies on high-throughput, precise phenotyping of plants at the whole-plant level, but is still in its infancy. Recently, several root chips have been reported to characterize root growth of the model plant *Arabidopsis thaliana* in different chemical, climate, and biological environments [E1-3], showing initial promise of high-throughput phenotyping of the root growth. But, phenotypic measurements on these devices were restricted to roots only, while measurements at the whole-plant level were not achieved. To the best of our knowledge, measurements at the whole-plant level have not been achieved. Here, we report on the development of a vertical microfluidic device for facilitating phenotypic assays of multiple plants at the whole organismal level, including seed germination, plant root growth, and shoot growth.

2. METHODS AND EXPERIMENTS a) Design of Device

FIG. 29 shows the schematic for the microfluidic plant chip. The device allows multiple plants to simultaneously grow in vertical direction in multiple growth regions. Each growth region includes a funnel shaped seed holding site on the top and a tapered, expanding channel on the bottom. The plant roots grow downward into the tapered channel. The room of a horizontal channel above the seed holding sites allows the plant shoots to grow upward. To accommodate phenotyping different plant species growing to different stages of interest, the number of the seed holding sites and the structure and geometry of the root and shoot growth regions can be flexibly changed during device design and fabrication. Specifically, the present device hosted 26 plants (here, *Arabidopsis thaliana*) distributed on two connecting floors. To hold *Arabidopsis* seeds and have enough room for seed germination, the lower and upper opening of the funnel-shaped holding site was designed to be ~350 μm and ~725 μm wide, respectively. The root and shoot growth region was 5 mm and 1.5 mm, respectively. All channels of the device were ~400 μm deep. This allowed us to observe the plant phenotypes for about two weeks. It should be pointed out that the vertical arrangement of the device can emulate the normal gravitropic growth of the plants. More importantly, the device, in conjunction with a stereo microscopic imaging system, can facilitate easy and high-quality observation of plant phenotypes at the whole organismal level, including seed germination, root growth, and shoot growth.

b) Simulation for Seed Trapping Process

Generally, *Arabidopsis* seeds are handled by sterilized tools such as forceps. Due to their small size at 200-300 μm, it would be difficult to manually load many seeds individually into multiple devices. Also, the seeds may get contaminated or even destroyed during manual handling of the seeds. Thus, a hydrodynamic trapping method is developed to load the seeds into the individual seed holding sites with automation (FIGS. 30A-C). Multiple seeds are infused into a main channel by flowing liquid medium. A sucking pressure is applied to force the seeds to flow against the lower wall of the main channel. As a seed flows by a holding site, the fluid streamlines carries the seed entering there. Since the seed holding site is designed to allow hosting only one seed, other seeds have to flow over this seed site to successive ones. Thus, the seeds can be trapped.

Finite element analysis (FEA) software COMSOL was used to simulate the hydrodynamic trapping process performed on the device. Two-dimensional fluid flow fields of the device were modelled and the Navier-Stokes equations were used for the simulation. All interior side walls were set to no-slip boundary condition. FIGS. 30A and 30B respectively display the fluid velocity and pressure distribution inside the channel during the course of seed trapping. The result shows that as the seed is carried out near a seed holding site, the velocity around the holding site increases and the pressure difference between outside and inside of the holding site (FIG. 30C) can push the seed into this trap.

c) Device Fabrication

The device was fabricated using a conventional soft lithography technique. Briefly, a silicon wafer was patterned with SU-8 photoresist (Microchem. Mass., USA) to create a master mould for microfluidic channels. A prepolymer mixture of polydimethylsiloxane or PDMS (Sylgard 184, Dow Corning, USA) and its curing agent with a weight ratio of 10:1 was poured onto the master mould and then thermally cured. Then, the hardened PDMS polymer was pealed from the master mould and bonded to a microscope glass slide (75 mm×50 mm×0.9 mm) through oxygen plasma treatment. The inlet and outlet ports of the device were manually punched with a mechanical puncher.

3. CULTURE MEDIA

Three different liquid culture media were prepared and used, including tap water, Murashige and Skoog (MS) medium, and MS plus 1% (W/V) sucrose medium. All the chemicals used were of analytical reagent grade. Deionized water was used throughout to prepare the latter two media. MS salts and sucrose were purchased from Sigma-Aldrich, Mo., USA. The culture media were sterilized in an autoclave at 15 psi at 121° C. for 30 min and stored at 4° C. They were loaded into the device using a 3 mL syringe (Beckton Dickinson, N.J., USA) with a microbore tubing (Cole-Parmer, Ill., USA) before the seeds were transferred into the device.

a) Treatment of Arabidopsis Seeds

Wild-type (WT) *Arabidopsis* was used as a model plant to demonstrate the workability of the device. All seeds were sterilized by treating in a solution containing 70% (V/V) ethanol, 50% (V/V) Clorox, and 0.02% (V/V) Triton. Then, the seeds were washing three times with autoclaved deionized (DI) water.

To trap and hold the *Arabidopsis* seeds, the lower opening size of the seed holding site must be less than the small diameter of the oval shaped seed. But, if the lower opening is made too small, the root growth of the seeds will be influenced due to the limited space. Therefore, the seeds were soaked in a Petri dish containing autoclaved DI water for 5-6 hrs to expand by ~15% on the small diameter.

b) Trapping of Arabidopsis Seeds

Before seed trapping, all channels in the device were filled up with one particular culture medium of interest by using a syringe via a tubing connection. Cares were taken to avoid introducing air bubbles into the channels. Subsequently, the soaked seeds were sucked from the soaking Petri dish up into a microbore tubing manually by a syringe. The tubing was then connected to the inlet port of the device. After that, a syringe pump (KDS200, KD Scientific, Mass., USA) was used to inject the seeds directly from the tubing into the device through the inlet port at an infusion flow rate of 2 cm/s. The other syringe pump (the same model) applied a sucking pressure through the outlet of the device at a withdrawal flow rate of 2 cm/s, forcing the seeds to flow along the lower sidewall of the channel. It took 3-4 s to complete the trapping process.

4. PLANT GROWTH CONDITIONS

After the seeds were trapped in the seed holding sites, the device was stored at 4° C. The device was taken out of the refrigerator and vertically placed under a plant growth light source (fluorescent daylight). The light intensity was set to be 95 µE/m²s. The plants were grown at room temperature (~21° C.). The environmental relative humidity was ~40%. The growth medium of interest was replenished with new medium on a daily basis. The plants germinated and grew in the device for 14 days.

A stereo microscope (MZ205, Leica, Germany) with a video camera (QI Camera) was used to image plant growth in the device. The system will collect phenotypic data of interest, including seed phenotype (e.g., germination), root phenotype (e.g., length and diameter), and shoot phenotype (e.g., hypocotyl, cotyledon and leaf emergence and dimensions). All data points reflect the average of at least three replicates.

5. RESULTS AND DISCUSSION

FIG. 31 shows the typical experimental result of the hydrodynamic seed trapping. Almost all seed holding sites in the device held seeds. 70-80% of these sites had a single seed while the rest of the sites trapped more than one seed. This is because the *Arabidopsis* seeds were not uniform in size and multiple smaller seeds could be trapped into one holding site. It was found that after one seed fell into a holding site other seeds could be first pushed into then flushed out of this site. The percentage of the trapped seeds with respect to the total input seeds was 20-30%. The untapped seeds were carried out downstream by the flowing fluid to a waste reservoir.

FIGS. 32A-C show the time-lapse images for the development of the *Arabidopsis thaliana* WT plants inside the devices containing three different growth media, i.e., tap water, MS medium, and MS plus 1% (W/V) sucrose medium. Since the device was made of the transparent material PDMS, imaging different plant organs at high resolution was possible. These images show that growing multiple plants in the same vertical plane allowed us to easily observe not only seeds and roots, but also shoots and even leaves of the plants at high resolution over time, without losing important plant growth information.

FIGS. 33A-C are major phenotypic parameters as a function of growth time, including (a) root length, (b) hypocotyl length, and (c) cotyledon surface area, respectively. The data were obtained by using Matlab based on the images taken at different time points.

On-chip germination of *Arabidopsis* seeds started at ~30, ~40, and ~30 hr with tap water, MS medium, and MS plus 1% (W/V) sucrose medium, respectively. It should be pointed that due to different installed positions of the seeds in the holding sites, the radicals of many seeds were not oriented initially downward. But as the radicals grew longer into roots, they tended to grow along a sidewall of the holding sites, and then, entered downward into the tapered root growth region. This observation was most likely attributed to gravitropism benefited from the vertical arrangement of the device.

The roots of *Arabidopsis* plants in all three growth media could grow downward as expected. Specifically, the roots growing in tap water were longer and thinner with sparser root hairs than those growing in MS and MS plus 1% sucrose media. This is because the roots need to reach out farther in search of nutrients when growing in a poor-nutrient environment (e.g., MS media). Also, adding 1% sucrose to MS medium had a very limited influence on the root growth. FIG. 33A plots the root length as a function of growth time, where the root length data was measured as the distance from the root tip to the root apex. The result shows that the roots grew rapidly from 30 to 120 hrs, but afterwards the growth rate slowed down.

The emergence and growth of the hypocotyl and cotyledon of *Arabidopsis* plants were also imaged with great details in this device. It was found that using a different growth medium had little influence on the hypocotyl length but a significant effect on the cotyledon size. FIG. 33B displays that the hypocotyls grew almost the same in length with tap water and MS plus 1% sucrose medium and slightly faster than they did with MS medium. The cotyledons of the plants with the three different media emerged from their seed coat almost at the same time (approximately 54 hrs after planting in the device). Specifically, as shown in FIG. 33C, the cotyledons began opening at ~54 hrs and then grew fast until at ~244 hrs. But, using MS medium allowed cotyledon to be grown larger than using tap water and MS plus 1% sucrose medium.

The seed germination and plant growth were compared between *Arabidopsis* plants grown in the present microfluidic devices and conventional Petri dishes. Differences in root, hypocotyl, and cotyledon growth of the plants were observed. Generally, in the first two weeks after seeding, the measured development characteristics of the plants grown in the devices were similar to those grown in the dishes. But afterwards, the plants grew slower in the devices than they did in the dishes. These discrepancies of growth stages between the plants grown in the device and Petri dish might be caused by the restricted space inside the devices and/or the nonoptimized protocol for replenishment with fresh growth medium. This limitation can be alleviated by scaling up the dimensions of particular structures and ensuring a frequent replenishment. However, the slower growth of the plants actually should not be a problem for the purpose of screening plant mutants' phenotypes to illustrate the relationship between the genotype and the phenotype of different organs of plants, as long as there are differences in phenotypes between different mutants.

6. CONCLUSIONS

We have developed a vertical microfluidic device for facilitating phenotypic assays of plant *Arabidopsis thaliana* at the whole organismal level. The device allows for convenient and high-quality observation of various plant phenotypes, including seed germination, root growth, and shoot growth. Further research and development remain to be done to realize an ultimate screening platform for high-throughput and high resolution plant phenotyping. Other micro-techniques can be developed and integrated into this plant growth microfluidic device. For example, through microfluidic tuning, flexible control over chemical concentration and composition in each growth channel can provide a large number of different nutrimental, chemical and biological (e.g., pathogens) environments for the plants growing in the device. Different means of generating concentration gradients have been demonstrated, including by using universal concentration generator, by on chip dilution, and by using droplet microfluidics. Also, to control plant growth temperature, a simple thin-film resistive heater and temperature sensor can be integrated on the plant chip. Furthermore, by employing an automated robotic imaging system, it is possible for users to take a large number of pictures for different plant growth regions on the devices with different magnifications.

We believe that the present technology can contribute to establish a powerful experimental framework for high-throughput and precise plant phenotyping. This is essential for plant scientists to obtain rapid discovery of phenotypes and the underlying genes that control the phenotypes under different conditions, particularly as many microfluidic technologies are available to flexibly generate complex and precise chemical and biological environments.

REFERENCES FOR SECTION E

[E1] H. Jiang, Y. Jiao, M. R. Maneesha. and L. Dong, "Electrospun nanofibrous membranes for temperature regulation of microfluidic seed growth chips", *Journal of Nanoscience and Nanotechnology*, vol. 12, pp. 6333-6339, 2012.

[E2] G. Grossmann, W. Guo, et al., "The Root Chip: an integrated microfluidic chip for plant science", *Plant Cell* vol. 23, pp. 4234-4240, 2011.

[E3] A. Parashar and S. Pandey, "Plant-in-chip: Microfluidic system for studying root growth and pathogenic interactions in *Arabidopsis*", *Appl. Phys. Lett.* 98: 263703, 2011.

F. Options and Alternatives

It will be appreciated by those skilled in this technological art that the invention can take many forms and embodiments. The examples given above are but a few. Variations obvious to those skilled in the art will be included within the invention, which is not limited to the examples given.

For example, as mentioned, the overall system can be scaled up or down. One embodiment is micro-sized (micro seed chip and microfluidics). But it can be scaled up beyond on the order of micro-scale. For example, cm or inch scale (e.g. 3 in.×3 in.×4 in.) or bigger are possible.

Additionally, the specific ways of placing and holding the seeds, delivering substances to them (and removing substances), and controlling that movement can vary.

Furthermore, the specific ways of fabricating and assembling the system can likewise vary.

If used, the micro seed chips (MSCs) can also vary. As mentioned, not all the exemplary generators and regulators need to be used for each MSC, or any MSC. In some cases just one or a subset of relative humidity, temperature, CO2, light intensity, and pathogens can be used. In others, additional factors can be generated or regulated to or in the MSC. Also, variations of specific communication between components can vary according to design and need. One example is substitution of wireless electrical communication for some or all of an electrical communication path or signal.

And, as mentioned, the plant species mentioned are examples only. Other plants as well as other items can be investigated with the system.

What is claimed is:

1. A system for high-throughput, large-scale plant phenotyping for screening of plant/environment interactions comprising:
   a. a plant growth platform sub-system comprising
      i. a plurality of miniaturized structures each comprising a miniature greenhouse for enclosing a controlled environment, each said miniature greenhouse including at least one substantially transparent window;

ii. a plurality of independently controllable regulators for providing variable plant growing factors to each miniature greenhouse; and
iii. a control system to control the regulators, and sense and acquire data related to the regulated plant growing factors;
b. a plant imaging sub-system comprising
   i. a digital imager;
   ii. a robotic actuator to provide adjustable position and attitude of the imager relative each of the miniature greenhouse for automated image acquisition of plants within each miniature greenhouse at or over specific times through its said at least one window with resolution spatially and temporally; and
c. a processor programmed with software algorithms to operate the image acquisition of the plant imaging sub-system and automatically access and evaluate the stored acquired images and the acquired data related to regulated plant growing factors for any said miniature greenhouse for correlation of phenotype/environment interactions for such purposes as plant phenomics, functional genomics, and systems biology.

2. The system of claim 1 wherein the regulators can either be on the miniature greenhouse or off the miniature greenhouse, and regulate in the miniature greenhouse controllable:
   a. relative humidity;
   b. light intensity,
   c. $CO_2$ level;
   d. temperature; and
   e. growing medium, including one or more of;
      i. water,
      ii. chemicals;
      iii. hormones; and
      iv. pathogens.

3. The system of claim 2 further comprising sensors to sense the plant growing factor associated with a correlated regulator.

4. The system of claim 3 wherein the control system to control the regulators adjusts operation of the regulators according to the sensors.

5. The system of claim 1 wherein the miniature greenhouses are positioned in an array on a platform.

6. The system of claim 5 wherein each miniature greenhouse encloses one or more microfluidic seed chips (MSCs) positioned for imaging through the at least one window by the plant imaging subsystem.

7. The system of claim 1 wherein the plant imaging sub-system includes storage for still images at adjustable spaced apart times or video images correlated to each and any of the miniature greenhouse, and the images can be of whole plants or portions of plants including magnified or other than visible light images.

8. The system of claim 7 where the imager is a stereo microscope-imager.

9. The system of claim 7 wherein the other than visible light images comprise at least one of:
   a. limited spectrum images;
   b. hyper spectral images;
   c. multi-spectral images;
   d. fluorescence images;
   e. infrared images; and
   f. x-ray images.

* * * * *